US012725702B2

(12) United States Patent
Sloan et al.

(10) Patent No.: US 12,725,702 B2
(45) Date of Patent: Sep. 1, 2026

(54) METHOD AND SYSTEM FOR PROVIDING BASAL PROFILE MODIFICATION IN ANALYTE MONITORING AND MANAGEMENT SYSTEMS

(71) Applicant: ABBOTT DIABETES CARE INC., Alameda, CA (US)

(72) Inventors: Mark Kent Sloan, Redwood City, CA (US); Gary Alan Hayter, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 701 days.

(21) Appl. No.: 17/966,442

(22) Filed: Oct. 14, 2022

(65) Prior Publication Data

US 2023/0052316 A1 Feb. 16, 2023

Related U.S. Application Data

(63) Continuation of application No. 16/177,811, filed on Nov. 1, 2018, now abandoned, which is a
(Continued)

(51) Int. Cl.
*G16H 40/67* (2018.01)
*A61B 5/00* (2006.01)
(Continued)

(52) U.S. Cl.
CPC ......... *G16H 40/67* (2018.01); *A61B 5/14532* (2013.01); *A61B 5/4839* (2013.01);
(Continued)

(58) Field of Classification Search
CPC ........ A61M 5/1723; A61M 2205/3303; A61M 2205/52; A61M 2230/201; G16H 10/40;
(Continued)

(56) References Cited

U.S. PATENT DOCUMENTS 3,260,656 A 7/1966 Ross, Jr.
3,304,413 A 2/1967 Lehmann et al.
(Continued)

FOREIGN PATENT DOCUMENTS

DE 2903216 A1 8/1979
DE 227029 9/1985
(Continued)

OTHER PUBLICATIONS

U.S. Appl. No. 61/246,630, filed Sep. 29, 2009, Shadforth, et al.
(Continued)

*Primary Examiner* — Christian Jang
(74) *Attorney, Agent, or Firm* — Sterne, Kessler, Goldstein & Fox P.L.L.C.

(57) ABSTRACT

Method and system for providing basal profile modification in insulin therapy for use with infusion devices includes periodically monitoring the analyte levels of a patient for a predetermined period of time in order to determine, based on the monitored analyte levels, an appropriate modification factor to be incorporated into the underlying basal profile which was running at the time the periodic monitoring of the analyte levels were performed.

20 Claims, 4 Drawing Sheets

Related U.S. Application Data continuation of application No. 15/880,692, filed on Jan. 26, 2018, now Pat. No. 11,538,580, which is a continuation of application No. 15/613,713, filed on Jun. 5, 2017, now abandoned, which is a continuation of application No. 15/071,610, filed on Mar. 16, 2016, now Pat. No. 9,669,162, which is a continuation of application No. 14/081,737, filed on Nov. 15, 2013, now Pat. No. 9,323,898, which is a continuation of application No. 12/833,975, filed on Jul. 10, 2010, now Pat. No. 8,585,591, which is a continuation of application No. 11/267,724, filed on Nov. 4, 2005, now Pat. No. 7,766,829.

(51) Int. Cl.

*A61B 5/145* (2006.01)
*A61M 5/172* (2006.01)
*G16H 10/40* (2018.01)
*G16H 10/60* (2018.01)
*G16H 20/17* (2018.01)
*G16Z 99/00* (2019.01)

(52) U.S. Cl.

CPC .......... *A61M 5/1723* (2013.01); *G16H 10/40* (2018.01); *G16H 10/60* (2018.01); *G16H 20/17* (2018.01); *G16Z 99/00* (2019.02); *A61B 2560/0223* (2013.01); *A61M 2205/3303* (2013.01); *A61M 2205/52* (2013.01); *A61M 2230/201* (2013.01)

(58) Field of Classification Search

CPC ........ G16H 20/17; G16H 40/67; G06F 19/00; G06F 19/3468; A61B 5/14532; A61B 5/4839; A61B 2560/0223

See application file for complete search history.

(56) References Cited

U.S. PATENT DOCUMENTS 3,581,062 A 5/1971 Aston
3,651,318 A 3/1972 Czekajewski
3,653,841 A 4/1972 Klein
3,698,386 A 10/1972 Fried
3,719,564 A 3/1973 Lilly, Jr. et al.
3,768,014 A 10/1973 Smith et al.
3,776,832 A 12/1973 Oswin et al.
3,837,339 A 9/1974 Aisenberg et al.
3,919,051 A 11/1975 Koch et al.
3,926,760 A 12/1975 Allen et al.
3,949,388 A 4/1976 Fuller
3,972,320 A 8/1976 Kalman
3,979,274 A 9/1976 Newman
4,003,379 A 1/1977 Ellinwood, Jr.
4,008,717 A 2/1977 Kowarski
4,016,866 A 4/1977 Lawton
4,021,718 A 5/1977 Konrad
4,036,749 A 7/1977 Anderson
4,055,175 A 10/1977 Clemens et al.
4,059,406 A 11/1977 Fleet
4,076,596 A 2/1978 Connery et al.
4,098,574 A 7/1978 Dappen
4,100,048 A 7/1978 Pompei et al.
4,129,128 A 12/1978 McFarlane
4,151,845 A 5/1979 Clemens
4,154,231 A 5/1979 Russell
4,168,205 A 9/1979 Danniger et al.
4,172,770 A 10/1979 Semersky et al.
4,178,916 A 12/1979 McNamara
4,193,026 A 3/1980 Finger et al.
4,206,755 A 6/1980 Klein
4,224,125 A 9/1980 Nakamura et al.
4,240,438 A 12/1980 Updike et al.
4,240,889 A 12/1980 Yoda et al.
4,245,634 A 1/1981 Albisser et al.
4,247,297 A 1/1981 Berti et al.
4,271,449 A 6/1981 Grogan
4,293,396 A 10/1981 Allen et al.
4,318,784 A 3/1982 Higgins et al.
4,327,725 A 5/1982 Cortese et al.
4,331,869 A 5/1982 Rollo
4,340,458 A 7/1982 Lerner et al.
4,344,438 A 8/1982 Schultz
4,349,728 A 9/1982 Phillips et al.
4,352,960 A 10/1982 Dormer et al.
4,356,074 A 10/1982 Johnson
4,365,637 A 12/1982 Johnson
4,366,033 A 12/1982 Richter et al.
4,375,399 A 3/1983 Havas et al.
4,384,586 A 5/1983 Christiansen
4,390,621 A 6/1983 Bauer
4,392,933 A 7/1983 Nakamura et al.
4,401,122 A 8/1983 Clark, Jr.
4,404,066 A 9/1983 Johnson
4,407,959 A 10/1983 Tsuji et al.
4,417,588 A 11/1983 Houghton et al.
4,418,148 A 11/1983 Oberhardt
4,420,564 A 12/1983 Tsuji et al.
4,425,920 A 1/1984 Bourland et al.
4,427,004 A 1/1984 Miller et al.
4,427,770 A 1/1984 Chen et al.
4,431,004 A 2/1984 Bessman et al.
4,436,094 A 3/1984 Cerami
4,440,175 A 4/1984 Wilkins
4,441,968 A 4/1984 Emmer et al.
4,444,892 A 4/1984 Malmros
4,450,842 A 5/1984 Zick et al.
4,458,686 A 7/1984 Clark, Jr.
4,461,691 A 7/1984 Frank
4,464,170 A 8/1984 Clemens et al.
4,467,811 A 8/1984 Clark, Jr.
4,469,110 A 9/1984 Slama
4,475,901 A 10/1984 Kraegen et al.
4,477,314 A 10/1984 Richter et al.
4,478,976 A 10/1984 Goertz et al.
4,483,924 A 11/1984 Tsuji et al.
4,484,987 A 11/1984 Gough
4,494,950 A 1/1985 Fischell
4,509,531 A 4/1985 Ward
4,512,348 A 4/1985 Uchigaki et al.
4,522,690 A 6/1985 Venkatsetty
4,524,114 A 6/1985 Samuels et al.
4,526,661 A 7/1985 Steckhan et al.
4,527,240 A 7/1985 Kvitash
4,534,356 A 8/1985 Papadakis
4,538,161 A 8/1985 Reist
4,538,616 A 9/1985 Rogoff
4,543,326 A 9/1985 Miyashita et al.
4,543,955 A 10/1985 Schroeppel
4,545,382 A 10/1985 Higgins et al.
4,552,840 A 11/1985 Riffer
4,560,534 A 12/1985 Kung et al.
4,569,589 A 2/1986 Neufeld
4,571,292 A 2/1986 Liu et al.
4,573,994 A 3/1986 Fischell et al.
4,581,336 A 4/1986 Malloy et al.
4,595,011 A 6/1986 Phillips
4,595,479 A 6/1986 Kimura et al.
4,601,707 A 7/1986 Albisser et al.
4,619,754 A 10/1986 Niki et al.
4,619,793 A 10/1986 Lee
4,627,445 A 12/1986 Garcia et al.
4,627,908 A 12/1986 Miller
4,633,878 A 1/1987 Bombardien
4,633,881 A 1/1987 Moore et al.
4,637,403 A 1/1987 Garcia et al.
4,648,408 A 3/1987 Hutcheson et al.
4,650,547 A 3/1987 Gough
4,653,513 A 3/1987 Dombrowski
4,654,197 A 3/1987 Lilja et al.
4,655,880 A 4/1987 Liu
4,655,885 A 4/1987 Hill et al.

(56) References Cited

U.S. PATENT DOCUMENTS 4,658,463 A 4/1987 Sugita et al.
4,671,288 A 6/1987 Gough
4,674,652 A 6/1987 Aten et al.
4,679,562 A 7/1987 Luksha
4,680,268 A 7/1987 Clark, Jr.
4,682,602 A 7/1987 Prohaska
4,684,537 A 8/1987 Graetzel et al.
4,685,463 A 8/1987 Williams
4,685,903 A 8/1987 Cable et al.
4,686,624 A 8/1987 Blum et al.
4,703,324 A 10/1987 White
4,703,756 A 11/1987 Gough et al.
4,711,245 A 12/1987 Higgins et al.
4,717,673 A 1/1988 Wrighton et al.
4,721,601 A 1/1988 Wrighton et al.
4,721,677 A 1/1988 Clark, Jr.
4,726,378 A 2/1988 Kaplan
4,726,716 A 2/1988 McGuire
4,731,726 A 3/1988 Allen, III
4,749,985 A 6/1988 Corsberg
4,750,496 A 6/1988 Reinhardt
4,757,022 A 7/1988 Shults et al.
4,758,323 A 7/1988 Davis et al.
4,759,371 A 7/1988 Franetzki
4,759,828 A 7/1988 Young et al.
4,764,416 A 8/1988 Ueyama et al.
4,776,944 A 10/1988 Janata et al.
4,777,953 A 10/1988 Ash et al.
4,779,618 A 10/1988 Mund et al.
4,781,798 A 11/1988 Gough
4,784,736 A 11/1988 Lonsdale et al.
4,795,707 A 1/1989 Niiyama et al.
4,796,634 A 1/1989 Huntsman et al.
4,803,625 A 2/1989 Fu et al.
4,805,624 A 2/1989 Yao et al.
4,810,658 A 3/1989 Shanks et al.
4,813,424 A 3/1989 Wilkins
4,815,469 A 3/1989 Cohen et al.
4,820,399 A 4/1989 Senda et al.
4,822,337 A 4/1989 Newhouse et al.
4,830,959 A 5/1989 McNeil et al.
4,832,797 A 5/1989 Vadgama et al.
4,835,372 A 5/1989 Gombrich et al.
RE32,947 E 6/1989 Dormer et al.
4,837,049 A 6/1989 Byers et al.
4,840,893 A 6/1989 Hill et al.
RE32,974 E 7/1989 Porat et al.
4,844,076 A 7/1989 Lesho et al.
4,845,035 A 7/1989 Fanta et al.
4,847,785 A 7/1989 Stephens
4,848,351 A 7/1989 Finch
4,854,322 A 8/1989 Ash et al.
4,856,340 A 8/1989 Garrison
4,857,713 A 8/1989 Brown
4,858,617 A 8/1989 Sanders
4,870,561 A 9/1989 Love et al.
4,871,351 A 10/1989 Feingold
4,871,440 A 10/1989 Nagata et al.
4,874,499 A 10/1989 Smith et al.
4,874,500 A 10/1989 Madou et al.
4,884,750 A 12/1989 Werding
4,890,620 A 1/1990 Gough
4,890,621 A 1/1990 Hakky
4,894,137 A 1/1990 Takizawa et al.
4,897,162 A 1/1990 Lewandowski et al.
4,897,173 A 1/1990 Nankai et al.
4,899,839 A 2/1990 Dessertine et al.
4,909,908 A 3/1990 Ross et al.
4,911,794 A 3/1990 Parce et al.
4,917,800 A 4/1990 Lonsdale et al.
4,919,141 A 4/1990 Zier et al.
4,919,767 A 4/1990 Vadgama et al.
4,920,969 A 5/1990 Suzuki
4,920,977 A 5/1990 Haynes
4,923,586 A 5/1990 Katayama et al.
4,925,268 A 5/1990 Iyer et al.
4,927,516 A 5/1990 Yamaguchi et al.
4,931,795 A 6/1990 Gord
4,934,369 A 6/1990 Maxwell
4,935,105 A 6/1990 Churchouse
4,935,345 A 6/1990 Guibeau et al.
4,936,956 A 6/1990 Wrighton
4,938,860 A 7/1990 Wogoman
4,942,127 A 7/1990 Wada et al.
4,944,299 A 7/1990 Silvian
4,945,045 A 7/1990 Forrest et al.
4,950,378 A 8/1990 Nagata
4,953,552 A 9/1990 DeMarzo
4,954,129 A 9/1990 Giuliani et al.
4,957,115 A 9/1990 Selker
4,958,632 A 9/1990 Duggan
4,968,400 A 11/1990 Shimomura et al.
4,969,468 A 11/1990 Byers et al.
4,970,145 A 11/1990 Bennetto et al.
4,974,929 A 12/1990 Curry
4,979,509 A 12/1990 Hakky
4,986,271 A 1/1991 Wilkins
4,990,845 A 2/1991 Gord
4,991,582 A 2/1991 Byers et al.
4,994,068 A 2/1991 Hufnagie
4,994,167 A 2/1991 Shults et al.
4,995,402 A 2/1991 Smith et al.
5,000,180 A 3/1991 Kuypers et al.
5,001,054 A 3/1991 Wagner
5,002,054 A 3/1991 Ash et al.
5,007,427 A 4/1991 Suzuki et al.
5,016,172 A 5/1991 Dessertine
5,016,201 A 5/1991 Bryan et al.
5,019,974 A 5/1991 Beckers
5,034,192 A 7/1991 Wrighton et al.
5,035,860 A 7/1991 Kleingeld et al.
5,036,860 A 8/1991 Leigh et al.
5,036,861 A 8/1991 Sembrowich et al.
5,037,527 A 8/1991 Hayashi et al.
5,049,487 A 9/1991 Phillips et al.
5,050,612 A 9/1991 Matsumura
5,051,688 A 9/1991 Murase et al.
5,055,171 A 10/1991 Peck
5,058,592 A 10/1991 Whisler
5,061,941 A 10/1991 Lizzi et al.
5,063,081 A 11/1991 Cozzette et al.
5,068,536 A 11/1991 Rosenthal
5,070,535 A 12/1991 Hochmair et al.
5,073,500 A 12/1991 Saito et al.
5,077,476 A 12/1991 Rosenthal
5,078,854 A 1/1992 Burgess et al.
5,082,550 A 1/1992 Rishpon et al.
5,082,786 A 1/1992 Nakamoto
5,084,828 A 1/1992 Kaufman et al.
5,089,112 A 2/1992 Skotheim et al.
5,094,951 A 3/1992 Rosenberg
5,095,904 A 3/1992 Seligman et al.
5,096,560 A 3/1992 Takai et al.
5,096,836 A 3/1992 Macho et al.
5,097,834 A 3/1992 Skrabal
5,101,814 A 4/1992 Palti
5,104,814 A 4/1992 Chipkin et al.
5,106,365 A 4/1992 Hernandez
5,108,564 A 4/1992 Szuminsky et al.
5,109,850 A 5/1992 Blanco et al.
5,111,539 A 5/1992 Hiruta et al.
5,111,818 A 5/1992 Suzuji et al.
5,114,678 A 5/1992 Crawford et al.
5,120,420 A 6/1992 Nankai et al.
5,120,421 A 6/1992 Glass et al.
5,122,925 A 6/1992 Inpyn
5,124,661 A 6/1992 Zellin et al.
5,126,034 A 6/1992 Carter et al.
5,126,247 A 6/1992 Palmer et al.
5,128,015 A 7/1992 Szuminsky et al.
5,130,009 A 7/1992 Marsoner et al.
5,133,856 A 7/1992 Yamaguchi et al.
5,134,391 A 7/1992 Okada
5,135,003 A 8/1992 Souma

(56) References Cited

U.S. PATENT DOCUMENTS 5,135,004 A 8/1992 Adams et al.
5,139,023 A 8/1992 Stanley et al.
5,140,393 A 8/1992 Hijikihigawa et al.
5,141,868 A 8/1992 Shanks et al.
5,161,532 A 11/1992 Joseph
5,165,407 A 11/1992 Wilson et al.
5,168,046 A 12/1992 Hamamoto et al.
5,173,165 A 12/1992 Schmid et al.
5,174,291 A 12/1992 Schoonen et al.
5,176,644 A 1/1993 Srisathapat et al.
5,176,662 A 1/1993 Bartholomew et al.
5,182,707 A 1/1993 Cooper et al.
5,184,359 A 2/1993 Tsukamura et al.
5,185,256 A 2/1993 Nankai et al.
5,190,041 A 3/1993 Palti
5,192,415 A 3/1993 Yoshioka et al.
5,192,416 A 3/1993 Wang et al.
5,193,539 A 3/1993 Schulman et al.
5,193,540 A 3/1993 Schulman et al.
5,197,322 A 3/1993 Indravudh
5,198,367 A 3/1993 Aizawa et al.
5,200,051 A 4/1993 Cozzette et al.
5,202,261 A 4/1993 Musho et al.
5,205,920 A 4/1993 Oyama et al.
5,206,145 A 4/1993 Cattell
5,208,154 A 5/1993 Weaver et al.
5,209,229 A 5/1993 Gilli
5,215,887 A 6/1993 Saito
5,216,597 A 6/1993 Beckers
5,217,442 A 6/1993 Davis
5,217,595 A 6/1993 Smith et al.
5,227,042 A 7/1993 Zawodzinski et al.
5,229,282 A 7/1993 Yoshioka et al.
5,236,143 A 8/1993 Dragon
5,236,567 A 8/1993 Nanba et al.
5,237,993 A 8/1993 Skrabal
5,245,314 A 9/1993 Kah et al.
5,246,867 A 9/1993 Lakowicz et al.
5,250,439 A 10/1993 Musho et al.
5,251,126 A 10/1993 Kahn et al.
5,257,971 A 11/1993 Lord et al.
5,257,980 A 11/1993 Van Antwerp et al.
5,261,401 A 11/1993 Baker et al.
5,262,035 A 11/1993 Gregg et al.
5,262,305 A 11/1993 Heller et al.
5,264,103 A 11/1993 Yoshioka et al.
5,264,104 A 11/1993 Gregg et al.
5,264,105 A 11/1993 Gregg et al.
5,264,106 A 11/1993 McAleer et al.
5,265,888 A 11/1993 Yamamoto et al.
5,266,179 A 11/1993 Nankai et al.
5,269,212 A 12/1993 Peters et al.
5,271,815 A 12/1993 Wong
5,272,060 A 12/1993 Hamamoto et al.
5,275,159 A 1/1994 Griebel
5,278,079 A 1/1994 Gubinski et al.
5,279,294 A 1/1994 Anderson et al.
5,282,950 A 2/1994 Dietze et al.
5,284,156 A 2/1994 Schramm et al.
5,285,792 A 2/1994 Sjoquist et al.
5,286,362 A 2/1994 Hoenes et al.
5,286,364 A 2/1994 Yacynych et al.
5,288,636 A 2/1994 Pollmann et al.
5,289,497 A 2/1994 Jackobson et al.
5,291,887 A 3/1994 Stanley et al.
5,293,546 A 3/1994 Tadros et al.
5,293,877 A 3/1994 O'Hara et al.
5,299,571 A 4/1994 Mastrototaro
5,304,468 A 4/1994 Phillips et al.
5,307,263 A 4/1994 Brown
5,309,919 A 5/1994 Snell et al.
5,310,885 A 5/1994 Maier et al.
5,320,098 A 6/1994 Davidson
5,320,725 A 6/1994 Gregg et al.
5,322,063 A 6/1994 Allen et al.
5,324,303 A 6/1994 Strong et al.
5,324,316 A 6/1994 Schulman et al.
5,326,449 A 7/1994 Cunningham
5,333,615 A 8/1994 Craelius et al.
5,337,258 A 8/1994 Dennis
5,337,747 A 8/1994 Neftei
5,340,722 A 8/1994 Wolfbeis et al.
5,342,408 A 8/1994 deCoriolis et al.
5,342,789 A 8/1994 Chick et al.
5,352,348 A 10/1994 Young et al.
5,356,348 A 10/1994 Bellio et al.
5,356,786 A 10/1994 Heller et al.
5,358,135 A 10/1994 Robbins et al.
5,358,514 A 10/1994 Schulman et al.
5,360,404 A 11/1994 Novacek et al.
5,364,797 A 11/1994 Olson et al.
5,366,609 A 11/1994 White et al.
5,368,028 A 11/1994 Palti
5,370,622 A 12/1994 Livingston et al.
5,371,687 A 12/1994 Holmes, II et al.
5,371,734 A 12/1994 Fischer
5,371,787 A 12/1994 Hamilton
5,372,133 A 12/1994 Hogen Esch
5,372,427 A 12/1994 Padovani et al.
5,376,070 A 12/1994 Purvis et al.
5,376,244 A 12/1994 Preidel
5,376,251 A 12/1994 Kaneko et al.
5,377,258 A 12/1994 Bro
5,378,628 A 1/1995 Gratzel et al.
5,379,238 A 1/1995 Stark
5,379,764 A 1/1995 Barnes et al.
5,380,422 A 1/1995 Negishi et al.
5,382,346 A 1/1995 Uenoyama et al.
5,387,327 A 2/1995 Khan
5,390,671 A 2/1995 Lord et al.
5,391,250 A 2/1995 Cheney, II et al.
5,393,903 A 2/1995 Gratzel et al.
5,395,504 A 3/1995 Saurer et al.
5,399,823 A 3/1995 McCusker
5,400,782 A 3/1995 Beaubiah
5,400,794 A 3/1995 Gorman
5,408,999 A 4/1995 Singh et al.
5,410,326 A 4/1995 Goldstein
5,410,471 A 4/1995 Alyfuku et al.
5,410,474 A 4/1995 Fox
5,411,647 A 5/1995 Johnson et al.
5,413,690 A 5/1995 Kost et al.
5,422,246 A 6/1995 Koopal et al.
5,425,868 A 6/1995 Pedersen
5,429,602 A 7/1995 Hauser
5,431,160 A 7/1995 Wilkins
5,431,691 A 7/1995 Snell et al.
5,431,921 A 7/1995 Thombre
5,433,710 A 7/1995 Van Antwerp et al.
5,437,973 A 8/1995 Vadgama et al.
5,437,999 A 8/1995 Dieboid et al.
5,438,271 A 8/1995 White et al.
5,445,611 A 8/1995 Eppstein et al.
5,445,920 A 8/1995 Saito
5,456,692 A 10/1995 Smith, Jr. et al.
5,456,940 A 10/1995 Funderburk
5,458,140 A 10/1995 Eppstein et al.
5,460,618 A 10/1995 Harreld
5,462,051 A 10/1995 Oka et al.
5,462,525 A 10/1995 Srisathapat et al.
5,462,645 A 10/1995 Albery et al.
5,466,218 A 11/1995 Srisathapat et al.
5,467,778 A 11/1995 Catt et al.
5,469,846 A 11/1995 Khan
5,472,317 A 12/1995 Field et al.
5,476,460 A 12/1995 Montalvo
5,477,855 A 12/1995 Schindler et al.
5,482,473 A 1/1996 Lord et al.
5,484,404 A 1/1996 Schulman et al.
5,487,751 A 1/1996 Radons et al.
5,491,474 A 2/1996 Suni et al.
5,494,562 A 2/1996 Maley et al.
5,496,453 A 3/1996 Uenoyama et al.
5,497,772 A 3/1996 Schulman et al.

(56) References Cited

U.S. PATENT DOCUMENTS 5,499,243 A 3/1996 Hall
5,501,956 A 3/1996 Wada et al.
5,505,709 A 4/1996 Funderburk
5,505,713 A 4/1996 Van Antwerp et al.
5,507,288 A 4/1996 Bocker et al.
5,508,171 A 4/1996 Walling et al.
5,509,410 A 4/1996 Hill et al.
5,514,103 A 5/1996 Srisathapat et al.
5,514,253 A 5/1996 Davis et al.
5,514,718 A 5/1996 Lewis et al.
5,518,006 A 5/1996 Mawhirt et al.
5,520,787 A 5/1996 Hanagan et al.
5,522,865 A 6/1996 Schulman et al.
5,525,511 A 6/1996 D'Costa
5,526,120 A 6/1996 Jina et al.
5,527,307 A 6/1996 Srisathapat et al.
5,529,676 A 6/1996 Maley et al.
5,531,878 A 7/1996 Vadgama et al.
5,538,511 A 7/1996 Van Antwerp et al.
5,544,196 A 8/1996 Tiedmann, Jr. et al.
5,545,152 A 8/1996 Funderburk et al.
5,545,191 A 8/1996 Mann et al.
5,549,113 A 8/1996 Halleck et al.
5,549,115 A 8/1996 Morgan et al.
5,552,027 A 9/1996 Birkle et al.
5,554,166 A 9/1996 Lange et al.
5,556,524 A 9/1996 Albers
5,560,357 A 10/1996 Faupei et al.
5,562,713 A 10/1996 Silvian
5,565,085 A 10/1996 Ikeda et al.
5,567,302 A 10/1996 Song et al.
5,568,806 A 10/1996 Cheney, II et al.
5,569,186 A 10/1996 Lord et al.
5,569,212 A 10/1996 Brown
5,573,647 A 11/1996 Maley et al.
5,575,895 A 11/1996 Ikeda et al.
5,580,527 A 12/1996 Bell et al.
5,580,794 A 12/1996 Allen
5,581,206 A 12/1996 Chevallier et al.
5,582,184 A 12/1996 Erickson et al.
5,582,697 A 12/1996 Ikeda et al.
5,582,698 A 12/1996 Flaherty et al.
5,584,813 A 12/1996 Livingston et al.
5,586,553 A 12/1996 Halili et al.
5,589,326 A 12/1996 Deng et al.
5,593,852 A 1/1997 Heller et al.
5,594,906 A 1/1997 Holmes, II et al.
5,596,150 A 1/1997 Arndy et al.
5,596,994 A 1/1997 Bro
5,600,301 A 2/1997 Robinson, III
5,601,435 A 2/1997 Quy
5,601,694 A 2/1997 Maley et al.
5,605,152 A 2/1997 Slate et al.
5,609,575 A 3/1997 Larson et al.
5,611,900 A 3/1997 Worden et al.
5,615,135 A 3/1997 Waclawsky et al.
5,615,671 A 4/1997 Schoonen et al.
5,616,222 A 4/1997 Maley et al.
5,617,851 A 4/1997 Lipkovker
5,623,925 A 4/1997 Swenson et al.
5,623,933 A 4/1997 Amano et al.
5,628,309 A 5/1997 Brown
5,628,310 A 5/1997 Rao et al.
5,628,324 A 5/1997 Sarbach
5,628,890 A 5/1997 Carter et al.
5,629,981 A 5/1997 Nerlikar
5,637,095 A 6/1997 Nason et al.
5,640,764 A 6/1997 Strojnik
5,640,954 A 6/1997 Pfeiffer et al.
5,643,212 A 7/1997 Coutre et al.
5,647,853 A 7/1997 Feldmann et al.
5,650,062 A 7/1997 Ikeda et al.
5,651,767 A 7/1997 Schulman et al.
5,651,869 A 7/1997 Yoshioka et al.
5,653,239 A 8/1997 Pompei et al.
5,658,444 A 8/1997 Black et al.
5,659,454 A 8/1997 Vermesse
5,660,163 A 8/1997 Schulman et al.
5,665,065 A 9/1997 Colman et al.
5,665,222 A 9/1997 Heller et al.
5,667,983 A 9/1997 Abel et al.
5,670,031 A 9/1997 Hintsche et al.
5,678,571 A 10/1997 Brown
5,679,690 A 10/1997 Andre et al.
5,680,858 A 10/1997 Hansen et al.
5,682,233 A 10/1997 Brinda
5,686,717 A 11/1997 Knowles et al.
5,695,623 A 12/1997 Michel et al.
5,695,949 A 12/1997 Galen et al.
5,701,894 A 12/1997 Cherry et al.
5,704,922 A 1/1998 Brown
5,707,502 A 1/1998 McCaffrey et al.
5,708,247 A 1/1998 McAleer et al.
5,710,630 A 1/1998 Essenpreis et al.
5,711,001 A 1/1998 Bussan et al.
5,711,297 A 1/1998 Iliff et al.
5,711,861 A 1/1998 Ward et al.
5,711,862 A 1/1998 Sakoda et al.
5,711,868 A 1/1998 Maley et al.
5,718,234 A 2/1998 Warden et al.
5,720,733 A 2/1998 Brown
5,720,862 A 2/1998 Hamamoto et al.
5,721,783 A 2/1998 Anderson
5,722,397 A 3/1998 Eppstein
5,726,646 A 3/1998 Bane et al.
5,727,548 A 3/1998 Hill et al.
5,730,124 A 3/1998 Yamauchi
5,730,654 A 3/1998 Brown
5,735,273 A 4/1998 Kurnik et al.
5,735,285 A 4/1998 Albert et al.
5,741,211 A 4/1998 Renirie et al.
5,741,688 A 4/1998 Oxenboll et al.
5,746,217 A 5/1998 Erickson et al.
5,748,103 A 5/1998 Flach et al.
5,750,926 A 5/1998 Schulman et al.
5,753,452 A 5/1998 Smith
5,758,290 A 5/1998 Nealon et al.
5,770,028 A 6/1998 Maley et al.
5,771,001 A 6/1998 Cobb
5,771,890 A 6/1998 Tamada
5,771,891 A 6/1998 Gozani
5,772,586 A 6/1998 Heinonen et al.
5,777,060 A 7/1998 Van Antwerp
5,779,665 A 7/1998 Mastrototaro et al.
5,780,304 A 7/1998 Matzinger et al.
5,781,024 A 7/1998 Blomberg et al.
5,782,814 A 7/1998 Brown et al.
5,785,681 A 7/1998 Indravudh
5,786,439 A 7/1998 Van Antwerp et al.
5,786,584 A 7/1998 Button et al.
5,788,678 A 8/1998 Van Antwerp
5,791,344 A 8/1998 Schulman et al.
5,792,117 A 8/1998 Brown
5,793,292 A 8/1998 Ivey
5,800,420 A 9/1998 Gross et al.
5,804,048 A 9/1998 Wong et al.
5,807,315 A 9/1998 Van Antwerp et al.
5,807,375 A 9/1998 Gross et al.
5,814,599 A 9/1998 Mitragotri et al.
5,820,551 A 10/1998 Hill et al.
5,820,570 A 10/1998 Erickson et al.
5,820,622 A 10/1998 Gross et al.
5,822,715 A 10/1998 Worthington et al.
5,825,488 A 10/1998 Kohl et al.
5,827,179 A 10/1998 Lichter et al.
5,827,183 A 10/1998 Kurnik et al.
5,827,184 A 10/1998 Netherly et al.
5,828,943 A 10/1998 Brown
5,830,064 A 11/1998 Bradish et al.
5,830,341 A 11/1998 Gilmartin
5,832,448 A 11/1998 Brown
5,834,224 A 11/1998 Ruger et al.
5,837,454 A 11/1998 Cozzette et al.
5,837,546 A 11/1998 Allen et al.

(56) References Cited

U.S. PATENT DOCUMENTS 5,840,020 A 11/1998 Heinonen et al.
5,842,983 A 12/1998 Abel et al.
5,843,140 A 12/1998 Strojnik
5,846,702 A 12/1998 Deng et al.
5,846,744 A 12/1998 Athey et al.
5,851,197 A 12/1998 Marano et al.
5,854,078 A 12/1998 Asher et al.
5,854,189 A 12/1998 Kruse et al.
5,856,758 A 1/1999 Joffe et al.
5,857,967 A 1/1999 Frid et al.
5,857,983 A 1/1999 Douglas et al.
5,860,917 A 1/1999 Comanor et al.
5,872,713 A 2/1999 Douglas et al.
5,876,484 A 3/1999 Raskin et al.
5,879,163 A 3/1999 Brown et al.
5,879,311 A 3/1999 Duchon et al.
5,880,829 A 3/1999 Kauhaniemi et al.
5,882,494 A 3/1999 Van Antwerp
5,885,211 A 3/1999 Eppstein et al.
5,887,133 A 3/1999 Brown et al.
5,897,493 A 4/1999 Brown
5,898,025 A 4/1999 Burg et al.
5,899,855 A 5/1999 Brown
5,913,310 A 6/1999 Brown
5,917,346 A 6/1999 Gord
5,918,603 A 7/1999 Brown
5,925,021 A 7/1999 Castellano et al.
5,931,791 A 8/1999 Saltzstein et al.
5,933,136 A 8/1999 Brown
5,935,099 A 8/1999 Petterson
5,935,224 A 8/1999 Svancarek et al.
5,939,609 A 8/1999 Knapp et al.
5,940,801 A 8/1999 Brown
5,942,979 A 8/1999 Luppino
5,945,345 A 8/1999 Blatt et al.
5,947,921 A 9/1999 Johnson et al.
5,948,512 A 9/1999 Kubota et al.
5,950,632 A 9/1999 Reber et al.
5,951,300 A 9/1999 Brown
5,951,492 A 9/1999 Douglas et al.
5,951,521 A 9/1999 Mastrototaro et al.
5,951,836 A 9/1999 McAleer et al.
5,954,643 A 9/1999 Van Antwerp
5,954,685 A 9/1999 Tierny
5,954,700 A 9/1999 Kovelman
5,956,501 A 9/1999 Brown
5,957,854 A 9/1999 Besson et al.
5,957,890 A 9/1999 Mann et al.
5,957,958 A 9/1999 Schulman et al.
5,960,403 A 9/1999 Brown
5,961,451 A 10/1999 Reber et al.
5,964,993 A 10/1999 Blubaugh, Jr. et al.
5,965,380 A 10/1999 Heller et al.
5,968,839 A 10/1999 Blatt et al.
5,971,922 A 10/1999 Arita et al.
5,971,941 A 10/1999 Simons et al.
5,974,124 A 10/1999 Schlueter, Jr. et al.
5,977,476 A 11/1999 Guha et al.
5,981,294 A 11/1999 Blatt et al.
5,989,409 A 11/1999 Kurnik et al.
5,994,476 A 11/1999 Shin et al.
5,995,860 A 11/1999 Sun et al.
5,997,476 A 12/1999 Brown
5,999,848 A 12/1999 Gord et al.
5,999,849 A 12/1999 Gord et al.
6,001,067 A 12/1999 Shults et al.
6,002,954 A 12/1999 Van Antwerp et al.
6,002,961 A 12/1999 Mitragotri et al.
6,004,441 A 12/1999 Fujiwara et al.
6,011,984 A 1/2000 Van Antwerp et al.
6,014,577 A 1/2000 Henning et al.
6,018,678 A 1/2000 Mitragotri et al.
6,023,629 A 2/2000 Tamada
6,024,699 A 2/2000 Surwit et al.
6,026,320 A 2/2000 Carlson et al.
6,027,459 A 2/2000 Shain et al.
6,027,692 A 2/2000 Galen et al.
6,028,413 A 2/2000 Brockmann
6,032,059 A 2/2000 Henning et al.
6,032,199 A 2/2000 Lim et al.
6,033,866 A 3/2000 Guo et al.
6,035,237 A 3/2000 Schulman et al.
6,040,194 A 3/2000 Chick et al.
6,041,253 A 3/2000 Kost et al.
6,043,437 A 3/2000 Schulman et al.
6,049,727 A 4/2000 Crothall
6,052,565 A 4/2000 Ishikura et al.
6,056,718 A 5/2000 Funderburk et al.
6,063,459 A 5/2000 Vette
6,066,243 A 5/2000 Anderson et al.
6,067,474 A 5/2000 Schulman et al.
6,068,615 A 5/2000 Brown et al.
6,071,249 A 6/2000 Cunningham et al.
6,071,251 A 6/2000 Cunningham et al.
6,071,294 A 6/2000 Simons et al.
6,071,391 A 6/2000 Gotoh et al.
6,073,031 A 6/2000 Helstab et al.
6,081,736 A 6/2000 Colvin et al.
6,083,710 A 7/2000 Heller et al.
6,088,608 A 7/2000 Schulman et al.
6,091,975 A 7/2000 Daddona et al.
6,091,976 A 7/2000 Pfeiffer et al.
6,093,156 A 7/2000 Cunningham et al.
6,093,167 A 7/2000 Houben et al.
6,093,172 A 7/2000 Funderburk et al.
6,096,364 A 8/2000 Bok et al.
6,097,480 A 8/2000 Kaplan
6,097,831 A 8/2000 Wieck et al.
6,099,484 A 8/2000 Douglas et al.
6,101,478 A 8/2000 Brown
6,103,033 A 8/2000 Say et al.
6,106,780 A 8/2000 Douglas et al.
6,110,148 A 8/2000 Brown et al.
6,110,152 A 8/2000 Kovelman
6,113,578 A 9/2000 Brown
6,117,290 A 9/2000 Say et al.
6,119,028 A 9/2000 Schulman et al.
6,120,676 A 9/2000 Heller et al.
6,121,009 A 9/2000 Heller et al.
6,121,611 A 9/2000 Lindsay et al.
6,122,351 A 9/2000 Schlueter, Jr. et al.
6,125,978 A 10/2000 Ando et al.
6,134,461 A 10/2000 Say et al.
6,134,504 A 10/2000 Douglas et al.
6,139,718 A 10/2000 Kurnik et al.
6,141,573 A 10/2000 Kurnik et al.
6,142,939 A 11/2000 Eppstein et al.
6,143,164 A 11/2000 Heller et al.
6,144,837 A 11/2000 Quy
6,144,869 A 11/2000 Berner et al.
6,144,922 A 11/2000 Douglas et al.
6,148,094 A 11/2000 Kinsella
6,150,128 A 11/2000 Uretsky
6,151,586 A 11/2000 Brown
6,153,062 A 11/2000 Saito et al.
6,153,069 A 11/2000 Pottgen et al.
6,159,147 A 12/2000 Lichter et al.
6,161,095 A 12/2000 Brown
6,162,611 A 12/2000 Heller et al.
6,162,639 A 12/2000 Douglas
6,164,284 A 12/2000 Schulman et al.
6,167,362 A 12/2000 Brown et al.
6,168,563 B1 1/2001 Brown
6,170,318 B1 1/2001 Lewis
6,175,752 B1 1/2001 Say et al.
6,180,416 B1 1/2001 Kurnik et al.
6,186,145 B1 2/2001 Brown
6,192,891 B1 2/2001 Gravel et al.
6,193,873 B1 2/2001 Ohara et al.
6,196,970 B1 3/2001 Brown
6,198,957 B1 3/2001 Green
6,200,265 B1 3/2001 Walsh et al.
6,201,979 B1 3/2001 Kurnik et al.
6,201,980 B1 3/2001 Darrow et al.

(56) References Cited

U.S. PATENT DOCUMENTS

| | | | |
|---|---|---|---|
| 6,203,495 | B1 | 3/2001 | Bardy et al. |
| 6,206,841 | B1 | 3/2001 | Cunningham et al. |
| 6,207,400 | B1 | 3/2001 | Kwon |
| 6,208,894 | B1 | 3/2001 | Schulman et al. |
| 6,210,272 | B1 | 4/2001 | Brown |
| 6,210,976 | B1 | 4/2001 | Sabbadini |
| 6,212,416 | B1 | 4/2001 | Ward et al. |
| 6,219,565 | B1 | 4/2001 | Cupp et al. |
| 6,219,574 | B1 | 4/2001 | Cormier et al. |
| 6,224,745 | B1 | 5/2001 | Baltruschat |
| 6,232,130 | B1 | 5/2001 | Wolf |
| 6,232,370 | B1 | 5/2001 | Kubota et al. |
| 6,233,471 | B1 | 5/2001 | Berner et al. |
| 6,233,539 | B1 | 5/2001 | Brown |
| 6,239,925 | B1 | 5/2001 | Ardrey et al. |
| 6,241,862 | B1 | 6/2001 | McAleer et al. |
| 6,246,330 | B1 | 6/2001 | Nielsen |
| 6,246,992 | B1 | 6/2001 | Brown |
| 6,248,065 | B1 | 6/2001 | Brown |
| 6,248,067 | B1 | 6/2001 | Causey, III et al. |
| 6,248,093 | B1 | 6/2001 | Moberg |
| 6,251,260 | B1 | 6/2001 | Heller et al. |
| 6,252,032 | B1 | 6/2001 | Van Antwerp et al. |
| 6,253,804 | B1 | 7/2001 | Safabash |
| 6,254,586 | B1 | 7/2001 | Mann et al. |
| 6,256,643 | B1 | 7/2001 | Cork et al. |
| 6,259,587 | B1 | 7/2001 | Sheldon et al. |
| 6,259,937 | B1 | 7/2001 | Schulman et al. |
| 6,260,022 | B1 | 7/2001 | Brown |
| 6,266,645 | B1 | 7/2001 | Simpson |
| 6,267,724 | B1 | 7/2001 | Taylor |
| 6,268,161 | B1 | 7/2001 | Han et al. |
| 6,270,445 | B1 | 8/2001 | Dean, Jr. et al. |
| 6,270,455 | B1 | 8/2001 | Brown |
| 6,272,364 | B1 | 8/2001 | Kurnik |
| 6,275,717 | B1 | 8/2001 | Gross et al. |
| 6,280,416 | B1 | 8/2001 | Van Antwerp et al. |
| 6,280,587 | B1 | 8/2001 | Matsumoto |
| 6,281,006 | B1 | 8/2001 | Heller et al. |
| 6,283,943 | B1 | 9/2001 | Dy et al. |
| 6,284,126 | B1 | 9/2001 | Kurnik et al. |
| 6,284,478 | B1 | 9/2001 | Heller et al. |
| 6,293,925 | B1 | 9/2001 | Safabash et al. |
| 6,294,281 | B1 | 9/2001 | Heller |
| 6,295,463 | B1 | 9/2001 | Stenzler |
| 6,295,506 | B1 | 9/2001 | Heinonen et al. |
| 6,298,254 | B2 | 10/2001 | Tamada |
| 6,299,347 | B1 | 10/2001 | Pompei |
| 6,299,578 | B1 | 10/2001 | Kurnik et al. |
| 6,299,757 | B1 | 10/2001 | Feldman et al. |
| 6,301,499 | B1 | 10/2001 | Carlson et al. |
| 6,304,766 | B1 | 10/2001 | Colvin, Jr. et al. |
| 6,306,104 | B1 | 10/2001 | Cunningham et al. |
| 6,307,867 | B1 | 10/2001 | Roobol et al. |
| 6,309,351 | B1 | 10/2001 | Kurnik et al. |
| 6,309,884 | B1 | 10/2001 | Cooper et al. |
| 6,313,749 | B1 | 11/2001 | Horne et al. |
| 6,314,317 | B1 | 11/2001 | Willis |
| 6,315,721 | B2 | 11/2001 | Schulman et al. |
| 6,319,540 | B1 | 11/2001 | Van Antwerp et al. |
| 6,326,160 | B1 | 12/2001 | Dunn et al. |
| 6,329,161 | B1 | 12/2001 | Heller et al. |
| 6,329,929 | B1 | 12/2001 | Weijand et al. |
| 6,330,426 | B2 | 12/2001 | Brown et al. |
| 6,330,464 | B1 | 12/2001 | Colvin, Jr. et al. |
| 6,331,518 | B2 | 12/2001 | Hemm et al. |
| 6,334,778 | B1 | 1/2002 | Brown |
| 6,336,900 | B1 | 1/2002 | Alleckson et al. |
| 6,338,790 | B1 | 1/2002 | Feldman et al. |
| 6,340,421 | B1 | 1/2002 | Vachon et al. |
| 6,341,232 | B1 | 1/2002 | Conn et al. |
| 6,356,776 | B1 | 3/2002 | Berner et al. |
| 6,359,270 | B1 | 3/2002 | Bridson |
| 6,359,594 | B1 | 3/2002 | Junod |
| 6,360,888 | B1 | 3/2002 | Mclvor et al. |
| 6,366,793 | B1 | 4/2002 | Bell et al. |
| 6,366,794 | B1 | 4/2002 | Moussy et al. |
| 6,368,141 | B1 | 4/2002 | Van et al. |
| 6,368,274 | B1 | 4/2002 | Van Antwerp et al. |
| 6,370,410 | B2 | 4/2002 | Kurnik et al. |
| 6,377,828 | B1 | 4/2002 | Chaiken et al. |
| 6,379,301 | B1 | 4/2002 | Worthington et al. |
| 6,383,767 | B1 | 5/2002 | Polak |
| 6,385,473 | B1 | 5/2002 | Haines et al. |
| 6,387,048 | B1 | 5/2002 | Schulman et al. |
| 6,391,643 | B1 | 5/2002 | Chen et al. |
| 6,393,318 | B1 | 5/2002 | Conn et al. |
| 6,398,562 | B1 | 6/2002 | Butler et al. |
| 6,405,066 | B1 | 6/2002 | Essenpreis et al. |
| 6,413,393 | B1 | 7/2002 | Van Antwerp et al. |
| 6,416,471 | B1 | 7/2002 | Kumar et al. |
| 6,418,332 | B1 | 7/2002 | Mastrototaro et al. |
| 6,424,847 | B1 | 7/2002 | Mastrototaro et al. |
| 6,427,088 | B1 | 7/2002 | Bowman, IV et al. |
| 6,434,409 | B1 | 8/2002 | Pfeiffer et al. |
| 6,438,414 | B1 | 8/2002 | Conn et al. |
| 6,440,068 | B1 | 8/2002 | Brown et al. |
| 6,441,747 | B1 | 8/2002 | Khair et al. |
| 6,442,637 | B1 | 8/2002 | Hawkins et al. |
| 6,442,672 | B1 | 8/2002 | Ganapathy |
| 6,443,942 | B2 | 9/2002 | Van Antwerp et al. |
| 6,449,255 | B1 | 9/2002 | Waclawsky et al. |
| 6,454,710 | B1 | 9/2002 | Ballerstadt et al. |
| 6,462,162 | B2 | 10/2002 | Van Antwerp et al. |
| 6,464,848 | B1 | 10/2002 | Matsumoto |
| 6,466,810 | B1 | 10/2002 | Ward et al. |
| 6,468,222 | B1 | 10/2002 | Mault et al. |
| 6,471,689 | B1 | 10/2002 | Joseph et al. |
| 6,472,122 | B1 | 10/2002 | Schulman et al. |
| 6,475,750 | B1 | 11/2002 | Han et al. |
| 6,477,395 | B2 | 11/2002 | Schulman et al. |
| 6,478,736 | B1 | 11/2002 | Mault |
| 6,480,730 | B2 | 11/2002 | Darrow et al. |
| 6,480,744 | B2 | 11/2002 | Ferek-Petric |
| 6,482,156 | B2 | 11/2002 | Iliff |
| 6,482,158 | B2 | 11/2002 | Mault |
| 6,482,604 | B2 | 11/2002 | Kwon |
| 6,484,045 | B1 | 11/2002 | Holker et al. |
| 6,484,046 | B1 | 11/2002 | Say et al. |
| 6,485,138 | B1 | 11/2002 | Kubota et al. |
| 6,493,069 | B1 | 12/2002 | Nagashimada et al. |
| 6,494,830 | B1 | 12/2002 | Wessel |
| 6,496,728 | B2 | 12/2002 | Li et al. |
| 6,505,059 | B1 | 1/2003 | Kollias et al. |
| 6,505,121 | B1 | 1/2003 | Russel |
| 6,512,939 | B1 | 1/2003 | Colvin et al. |
| 6,513,532 | B2 | 2/2003 | Mault et al. |
| 6,514,718 | B2 | 2/2003 | Heller et al. |
| 6,515,593 | B1 | 2/2003 | Stark et al. |
| 6,520,326 | B2 | 2/2003 | Mclvor et al. |
| 6,529,755 | B2 | 3/2003 | Kurnik et al. |
| 6,529,772 | B2 | 3/2003 | Carlson et al. |
| 6,530,915 | B1 | 3/2003 | Eppstein et al. |
| 6,534,322 | B1 | 3/2003 | Sabbadini |
| 6,534,323 | B1 | 3/2003 | Sabbadini |
| 6,535,753 | B1 | 3/2003 | Raskas |
| 6,537,243 | B1 | 3/2003 | Henning et al. |
| 6,540,675 | B2 | 4/2003 | Aceti et al. |
| 6,541,266 | B2 | 4/2003 | Modzelweskei et al. |
| 6,544,212 | B2 | 4/2003 | Galley et al. |
| 6,546,268 | B1 | 4/2003 | Ishikawa et al. |
| 6,546,269 | B1 | 4/2003 | Kurnik |
| 6,549,796 | B2 | 4/2003 | Sohrab |
| 6,551,276 | B1 | 4/2003 | Mann et al. |
| 6,551,494 | B1 | 4/2003 | Heller et al. |
| 6,553,244 | B2 | 4/2003 | Lesho et al. |
| 6,554,798 | B1 | 4/2003 | Mann et al. |
| 6,558,320 | B1 | 5/2003 | Causey, III et al. |
| 6,558,321 | B1 | 5/2003 | Burd et al. |
| 6,558,351 | B1 | 5/2003 | Steil et al. |
| 6,560,471 | B1 | 5/2003 | Heller et al. |
| 6,561,978 | B1 | 5/2003 | Conn et al. |
| 6,562,001 | B2 | 5/2003 | Lebel et al. |
| 6,564,105 | B2 | 5/2003 | Starkweather et al. |

(56) References Cited

U.S. PATENT DOCUMENTS 6,564,807 B1 5/2003 Schulman et al.
6,565,509 B1 5/2003 Say et al.
6,571,128 B2 5/2003 Lebel et al.
6,571,200 B1 5/2003 Mault
6,572,545 B2 6/2003 Knobbe et al.
6,576,101 B1 6/2003 Heller et al.
6,576,117 B1 6/2003 Iketaki et al.
6,577,899 B2 6/2003 Lebel et al.
6,579,498 B1 6/2003 Eglise
6,579,690 B1 6/2003 Bonnecaze et al.
6,584,335 B1 6/2003 Haar et al.
6,585,644 B2 7/2003 Lebel et al.
6,587,705 B1 7/2003 Kim et al.
6,591,125 B1 7/2003 Buse et al.
6,591,126 B2 7/2003 Roeper et al.
6,594,514 B2 7/2003 Berner et al.
6,595,919 B2 7/2003 Berner et al.
6,595,929 B2 7/2003 Stivoric et al.
6,602,678 B2 8/2003 Kwon et al.
6,602,909 B1 8/2003 Jarowski
6,605,200 B1 8/2003 Mao et al.
6,605,201 B1 8/2003 Mao et al.
6,607,509 B2 8/2003 Bobroff et al.
6,608,562 B1 8/2003 Kimura et al.
6,610,012 B2 8/2003 Mault
6,611,206 B2 8/2003 Eshelman et al.
6,612,306 B1 9/2003 Mault
6,615,078 B1 9/2003 Burson et al.
6,616,613 B1 9/2003 Goodman
6,618,603 B2 9/2003 Varalli et al.
6,620,106 B2 9/2003 Mault
6,627,058 B1 9/2003 Chan
6,627,154 B1 9/2003 Goodman et al.
6,629,934 B2 10/2003 Mault et al.
6,633,772 B2 10/2003 Ford et al.
6,635,014 B2 10/2003 Starkweather et al.
6,641,533 B2 11/2003 Causey, III et al.
6,642,015 B2 11/2003 Vachon et al.
6,645,142 B2 11/2003 Braig et al.
6,645,368 B1 11/2003 Beaty et al.
6,648,821 B2 11/2003 Lebel et al.
6,653,091 B1 11/2003 Dunn et al.
6,654,625 B1 11/2003 Say et al.
6,656,114 B1 12/2003 Poulson et al.
6,658,396 B1 12/2003 Tang et al.
6,659,948 B2 12/2003 Lebel et al.
6,668,196 B1 12/2003 Villegas et al.
6,671,554 B2 12/2003 Gibson et al.
6,673,625 B2 1/2004 Satcher, Jr. et al.
6,675,030 B2 1/2004 Ciurczak et al.
6,682,938 B1 1/2004 Satcher, Jr. et al.
6,683,040 B2 1/2004 Bragulla et al.
6,687,522 B2 2/2004 Tamada
6,687,546 B2 2/2004 Lebel et al.
6,689,056 B1 2/2004 Kilcoyne et al.
6,690,276 B1 2/2004 Marino
6,692,446 B2 2/2004 Hoek
6,693,069 B2 2/2004 Korber et al.
6,694,158 B2 2/2004 Polak
6,694,191 B2 2/2004 Starkweather et al.
6,695,860 B1 2/2004 Ward et al.
6,698,269 B2 3/2004 Baber et al.
6,701,270 B1 3/2004 Miller et al.
6,702,857 B2 3/2004 Brauker et al.
6,704,587 B1 3/2004 Kumar et al.
6,708,057 B2 3/2004 Marganroth
6,711,423 B2 3/2004 Colvin, Jr.
6,723,046 B2 4/2004 Lichtenstein et al.
6,728,560 B2 4/2004 Kollias et al.
6,731,976 B2 5/2004 Penn et al.
6,733,446 B2 5/2004 Lebel et al.
6,734,162 B2 5/2004 Van Antwerp et al.
6,735,479 B2 5/2004 Fabian et al.
6,736,777 B2 5/2004 Kim et al.
6,736,797 B1 5/2004 Larsen et al.
6,737,401 B2 5/2004 Kim et al.
6,738,654 B2 5/2004 Sohrab
6,740,075 B2 5/2004 Lebel et al.
6,741,163 B1 5/2004 Roberts
6,741,876 B1 5/2004 Scecina et al.
6,741,877 B1 5/2004 Shults et al.
6,746,582 B2 6/2004 Heller et al.
6,748,445 B1 6/2004 Darcey et al.
6,749,587 B2 6/2004 Flaherty
6,750,311 B1 6/2004 Van Antwerp et al.
6,758,810 B2 7/2004 Lebel et al.
6,766,183 B2 7/2004 Walsh et al.
6,766,201 B2 7/2004 Von Arx et al.
6,768,425 B2 7/2004 Flaherty et al.
6,770,030 B1 8/2004 Schaupp et al.
6,770,729 B2 8/2004 Van Antwerp et al.
6,771,995 B2 8/2004 Kurnik et al.
6,773,563 B2 8/2004 Matsumoto
6,780,156 B2 8/2004 Haueter et al.
6,780,297 B2 8/2004 Matsumoto et al.
6,780,871 B2 8/2004 Glick et al.
6,784,274 B2 8/2004 Van Antwerp et al.
6,790,178 B1 9/2004 Mault et al.
6,794,195 B2 9/2004 Colvin, Jr.
6,800,451 B2 10/2004 Daniloff et al.
6,804,544 B2 10/2004 Van Antwerp et al.
6,809,507 B2 10/2004 Morgan et al.
6,809,653 B1 10/2004 Mann et al.
6,810,290 B2 10/2004 Lebel et al.
6,810,309 B2 10/2004 Sadler et al.
6,811,533 B2 11/2004 Lebel et al.
6,811,534 B2 11/2004 Bowman, IV et al.
6,811,659 B2 11/2004 Vachon
6,812,031 B1 11/2004 Carlsson
6,813,519 B2 11/2004 Lebel et al.
6,816,742 B2 11/2004 Kim et al.
6,835,553 B2 12/2004 Han et al.
RE38,681 E 1/2005 Kurnik et al.
6,840,912 B2 1/2005 Kloepfer et al.
6,844,023 B2 1/2005 Schulman et al.
6,849,237 B2 2/2005 Housefield et al.
6,850,790 B2 2/2005 Berner et al.
6,852,104 B2 2/2005 Blomquist
6,852,500 B1 2/2005 Hoss et al.
6,852,694 B2 2/2005 Van Antwerp et al.
6,853,854 B1 2/2005 Proniewicz et al.
6,856,928 B2 2/2005 Harmon
6,858,403 B2 2/2005 Han et al.
6,862,465 B2 3/2005 Shults et al.
6,862,466 B2 3/2005 Ackerman
6,872,200 B2 3/2005 Mann et al.
6,873,268 B2 3/2005 Lebel et al.
6,881,551 B2 4/2005 Heller et al.
6,882,940 B2 4/2005 Potts et al.
6,885,883 B2 4/2005 Parris et al.
6,889,331 B2 5/2005 Soerensen et al.
6,892,085 B2 5/2005 Mclvor et al.
6,895,263 B2 5/2005 Shin et al.
6,895,265 B2 5/2005 Silver
6,899,683 B2 5/2005 Mault et al.
6,899,684 B2 5/2005 Mault et al.
6,902,207 B2 6/2005 Lickliter
6,902,905 B2 6/2005 Burson et al.
6,904,301 B2 6/2005 Raskas
6,907,127 B1 6/2005 Kravitz et al.
6,915,147 B2 7/2005 Lebel et al.
6,918,874 B1 7/2005 Hatch et al.
6,922,578 B2 7/2005 Eppstein et al.
RE38,775 E 8/2005 Kurnik et al.
6,923,763 B1 8/2005 Kovatchev et al.
6,923,764 B2 8/2005 Aceti et al.
6,923,936 B2 8/2005 Swanson et al.
6,927,246 B2 8/2005 Noronha et al.
6,931,327 B2 8/2005 Goode, Jr. et al.
6,932,894 B2 8/2005 Mao et al.
6,936,006 B2 8/2005 Sabra
6,936,029 B2 8/2005 Mann et al.
6,937,222 B2 8/2005 Numao
6,940,590 B2 9/2005 Colvin, Jr. et al.

(56) References Cited

U.S. PATENT DOCUMENTS 6,941,163 B2 9/2005 Ford et al.
6,950,708 B2 9/2005 Bowman IV et al.
6,952,603 B2 10/2005 Gelber et al.
6,954,673 B2 10/2005 Von Arx et al.
6,955,650 B2 10/2005 Mault et al.
6,957,102 B2 10/2005 Silver et al.
6,957,107 B2 10/2005 Rogers et al.
6,958,705 B2 10/2005 Lebel et al.
6,968,294 B2 11/2005 Gutta et al.
6,968,375 B1 11/2005 Brown
6,971,274 B2 12/2005 Olin
6,974,437 B2 12/2005 Lebel et al.
6,978,182 B2 12/2005 Mazar et al.
6,979,326 B2 12/2005 Mann et al.
6,983,176 B2 1/2006 Gardner et al.
6,985,870 B2 1/2006 Martucci et al.
6,990,366 B2 1/2006 Say et al.
6,991,096 B2 1/2006 Gottlieb et al.
6,997,907 B2 2/2006 Safabash et al.
6,997,920 B2 2/2006 Mann et al.
6,998,247 B2 2/2006 Monfre et al.
6,999,810 B2 2/2006 Berner et al.
7,003,336 B2 2/2006 Holker et al.
7,003,340 B2 2/2006 Say et al.
7,003,341 B2 2/2006 Say et al.
7,004,901 B2 2/2006 Fish
7,005,857 B2 2/2006 Stiene et al.
7,011,630 B2 3/2006 Desai et al.
7,018,366 B2 3/2006 Easter
7,018,568 B2 3/2006 Tierney
7,022,072 B2 4/2006 Fox et al.
7,024,236 B2 4/2006 Ford et al.
7,024,245 B2 4/2006 Lebel et al.
7,025,743 B2 4/2006 Mann et al.
7,027,931 B1 4/2006 Jones et al.
7,029,444 B2 4/2006 Shin et al.
7,039,810 B1 5/2006 Nichols
7,041,068 B2 5/2006 Freeman et al.
7,041,468 B2 5/2006 Drucker et al.
7,049,277 B2 5/2006 Bagulla et al.
7,052,251 B2 5/2006 Nason et al.
7,052,472 B1 5/2006 Miller et al.
7,052,483 B2 5/2006 Wojcik
7,056,302 B2 6/2006 Douglas
7,060,030 B2 6/2006 Von Arx et al.
7,074,307 B2 7/2006 Simpson et al.
7,081,195 B2 7/2006 Simpson et al.
7,089,780 B2 8/2006 Sunshine et al.
7,098,803 B2 8/2006 Mann et al.
7,108,778 B2 9/2006 Simpson et al.
7,110,803 B2 9/2006 Shults et al.
7,113,821 B1 9/2006 Sun et al.
7,114,502 B2 10/2006 Schulman et al.
7,124,027 B1 10/2006 Ernst et al.
7,125,382 B2 10/2006 Zhou et al.
7,133,710 B2 11/2006 Acosta et al.
7,134,999 B2 11/2006 Brauker et al.
7,136,689 B2 11/2006 Shults et al.
7,150,975 B2 12/2006 Tamada et al.
7,154,398 B2 12/2006 Chen et al.
7,155,112 B2 12/2006 Uno et al.
7,155,290 B2 12/2006 Von Arx et al.
7,163,511 B2 1/2007 Conn et al.
7,167,818 B2 1/2007 Brown
7,171,274 B2 1/2007 Starkweather et al.
7,174,199 B2 2/2007 Berner et al.
7,183,068 B2 2/2007 Burson et al.
7,183,102 B2 2/2007 Monfre et al.
7,189,341 B2 3/2007 Li et al.
7,190,988 B2 3/2007 Say et al.
7,192,450 B2 3/2007 Brauker et al.
7,198,606 B2 4/2007 Boecker et al.
7,221,977 B1 5/2007 Weaver et al.
7,225,535 B2 6/2007 Feldman et al.
7,226,442 B2 6/2007 Sheppard et al.
7,226,978 B2 6/2007 Tapsak et al.
7,228,162 B2 6/2007 Ward et al.
7,228,163 B2 6/2007 Ackerman
7,233,817 B2 6/2007 Yen
7,241,266 B2 7/2007 Zhou et al.
7,261,691 B1 8/2007 Asomani
7,267,665 B2 9/2007 Steil et al.
7,276,029 B2 10/2007 Goode, Jr. et al.
7,278,983 B2 10/2007 Ireland et al.
7,286,894 B1 10/2007 Grant et al.
7,291,107 B2 11/2007 Hellwig et al.
7,295,867 B2 11/2007 Berner et al.
7,297,112 B2 11/2007 Zhou et al.
7,299,082 B2 11/2007 Feldman et al.
7,310,544 B2 12/2007 Brister et al.
7,324,012 B2 1/2008 Mann et al.
7,354,420 B2 4/2008 Steil et al.
7,364,592 B2 4/2008 Carr-Brendel et al.
7,366,556 B2 4/2008 Brister et al.
7,379,765 B2 5/2008 Petisce et al.
7,398,183 B2 7/2008 Holland et al.
7,402,153 B2 7/2008 Steil et al.
7,404,796 B2 7/2008 Ginsberg
7,408,132 B2 8/2008 Wambsganss et al.
7,424,318 B2 9/2008 Brister et al.
7,460,898 B2 12/2008 Brister et al.
7,467,003 B2 12/2008 Brister et al.
7,471,972 B2 12/2008 Rhodes et al.
7,492,461 B2 2/2009 Hebert et al.
7,494,465 B2 2/2009 Brister et al.
7,497,827 B2 3/2009 Brister et al.
7,498,132 B2 3/2009 Yu et al.
7,519,408 B2 4/2009 Rasdal et al.
7,547,281 B2 6/2009 Hayes et al.
7,569,030 B2 8/2009 Lebel et al.
7,583,990 B2 9/2009 Goode, Jr. et al.
7,591,801 B2 9/2009 Brauker et al.
7,599,726 B2 10/2009 Goode, Jr. et al.
7,613,491 B2 11/2009 Boock et al.
7,615,007 B2 11/2009 Shults et al.
7,632,228 B2 12/2009 Brauker et al.
7,637,868 B2 12/2009 Saint et al.
7,640,048 B2 12/2009 Dobbles et al.
7,651,596 B2 1/2010 Petisce et al.
7,653,425 B2 1/2010 Hayter et al.
7,654,956 B2 2/2010 Brister et al.
7,657,297 B2 2/2010 Simpson et al.
7,699,775 B2 4/2010 Desai et al.
7,701,052 B2 4/2010 Borland et al.
7,711,402 B2 5/2010 Shults et al.
7,713,574 B2 5/2010 Brister et al.
7,715,893 B2 5/2010 Kamath et al.
7,766,829 B2 8/2010 Sloan et al.
7,766,831 B2 8/2010 Essenpreis et al.
7,775,444 B2 8/2010 DeRocco et al.
7,811,231 B2 10/2010 Jin et al.
7,813,809 B2 10/2010 Strother et al.
7,833,151 B2 11/2010 Khait et al.
7,889,069 B2 2/2011 Fifolt et al.
7,941,200 B2 5/2011 Weinert et al.
7,946,985 B2 5/2011 Mastrototaro et al.
7,978,063 B2 7/2011 Baldus et al.
8,000,918 B2 8/2011 Fjield et al.
8,010,174 B2 8/2011 Goode et al.
8,010,256 B2 8/2011 Oowada
8,282,549 B2 10/2012 Brauker et al.
8,500,054 B2 8/2013 Grant et al.
8,512,243 B2 8/2013 Stafford
9,827,372 B2 11/2017 Dobbles et al.
10,980,461 B2 4/2021 Simpson et al.
11,538,580 B2 * 12/2022 Sloan ................. A61M 5/1723
2001/0011224 A1 8/2001 Brown
2001/0011795 A1 8/2001 Ohtsuka et al.
2001/0016310 A1 8/2001 Brown et al.
2001/0016682 A1 8/2001 Berner et al.
2001/0016683 A1 8/2001 Darrow et al.
2001/0020124 A1 9/2001 Tamada
2001/0029340 A1 10/2001 Mault et al.
2001/0032278 A1 10/2001 Brown et al.

(56) References Cited

U.S. PATENT DOCUMENTS

2001/0037060 A1 11/2001 Thompson et al.
2001/0037069 A1 11/2001 Carlson et al.
2001/0037366 A1 11/2001 Webb et al.
2001/0039504 A1 11/2001 Linberg et al.
2001/0041830 A1 11/2001 Varalli et al.
2001/0041831 A1 11/2001 Starkweather et al.
2001/0044581 A1 11/2001 Mault
2001/0044588 A1 11/2001 Mault
2001/0047125 A1 11/2001 Quy
2001/0047127 A1 11/2001 New et al.
2001/0049096 A1 12/2001 Brown
2001/0049470 A1 12/2001 Mault et al.
2002/0002326 A1 1/2002 Causey, III et al.
2002/0002328 A1 1/2002 Tamada
2002/0004640 A1 1/2002 Conn et al.
2002/0010414 A1 1/2002 Coston et al.
2002/0013522 A1 1/2002 Lay et al.
2002/0013538 A1 1/2002 Teller
2002/0016530 A1 2/2002 Brown
2002/0016719 A1 2/2002 Nemeth et al.
2002/0019022 A1 2/2002 Dunn et al.
2002/0019584 A1 2/2002 Schulze et al.
2002/0019586 A1 2/2002 Teller et al.
2002/0019748 A1 2/2002 Brown
2002/0023852 A1 2/2002 McIyor et al.
2002/0026937 A1 3/2002 Mault
2002/0027164 A1 3/2002 Mault et al.
2002/0028995 A1 3/2002 Mault
2002/0040208 A1 4/2002 Flaherty et al.
2002/0042090 A1 4/2002 Heller et al.
2002/0045808 A1 4/2002 Ford et al.
2002/0047867 A1 4/2002 Mault et al.
2002/0049482 A1 4/2002 Fabian et al.
2002/0053637 A1 5/2002 Conn et al.
2002/0062069 A1 5/2002 Mault
2002/0063060 A1 5/2002 Gascoyne et al.
2002/0065454 A1 5/2002 Lebel et al.
2002/0068858 A1 6/2002 Braig et al.
2002/0072784 A1 6/2002 Sheppard et al.
2002/0072858 A1 6/2002 Cheng
2002/0074162 A1 6/2002 Su et al.
2002/0077765 A1 6/2002 Mault
2002/0077766 A1 6/2002 Mault
2002/0081559 A1 6/2002 Brown et al.
2002/0083461 A1 6/2002 Hutcheson et al.
2002/0084196 A1 7/2002 Liamos et al.
2002/0087056 A1 7/2002 Aceti et al.
2002/0091312 A1 7/2002 Berner et al.
2002/0091796 A1 7/2002 Higginson et al.
2002/0093969 A1 7/2002 Lin et al.
2002/0103425 A1 8/2002 Mault
2002/0103499 A1 8/2002 Perez et al.
2002/0106709 A1 8/2002 Potts et al.
2002/0107433 A1 8/2002 Mault
2002/0107476 A1 8/2002 Mann et al.
2002/0109600 A1 8/2002 Mault et al.
2002/0118528 A1 8/2002 Su et al.
2002/0119711 A1 8/2002 Van et al.
2002/0124017 A1 9/2002 Mault
2002/0126036 A1 9/2002 Flaherty et al.
2002/0128594 A1 9/2002 Das et al.
2002/0130042 A1 9/2002 Moerman et al.
2002/0133378 A1 9/2002 Mault et al.
2002/0147135 A1 10/2002 Schnell
2002/0161286 A1 10/2002 Gelber et al.
2002/0161288 A1 10/2002 Shin et al.
2002/0169394 A1 11/2002 Eppstein et al.
2002/0169635 A1 11/2002 Shillingburg
2002/0177764 A1 11/2002 Sohrab
2002/0185130 A1 12/2002 Wright et al.
2002/0193679 A1 12/2002 Malave et al.
2003/0004403 A1 1/2003 Drinan et al.
2003/0023182 A1 1/2003 Mault et al.
2003/0023317 A1 1/2003 Brauker et al.
2003/0028089 A1* 2/2003 Galley .............. A61B 5/14532 128/920
2003/0028120 A1 2/2003 Mault et al.
2003/0032077 A1 2/2003 Itoh et al.
2003/0032867 A1 2/2003 Crothall et al.
2003/0032868 A1 2/2003 Graskov et al.
2003/0032874 A1 2/2003 Rhodes et al.
2003/0039298 A1 2/2003 Eriksson et al.
2003/0040683 A1 2/2003 Rule et al.
2003/0042137 A1 3/2003 Mao et al.
2003/0050537 A1 3/2003 Wessel
2003/0050546 A1 3/2003 Desai et al.
2003/0060692 A1 3/2003 Ruchti et al.
2003/0060753 A1 3/2003 Starkweather et al.
2003/0065257 A1 4/2003 Mault et al.
2003/0065273 A1 4/2003 Mault et al.
2003/0065274 A1 4/2003 Mault et al.
2003/0065275 A1 4/2003 Mault et al.
2003/0065308 A1 4/2003 Lebel et al.
2003/0076792 A1 4/2003 Theimer
2003/0081370 A1 5/2003 Haskell et al.
2003/0100040 A1 5/2003 Bonnecaze et al.
2003/0100821 A1 5/2003 Heller et al.
2003/0105407 A1 6/2003 Pearce et al.
2003/0108976 A1 6/2003 Braig et al.
2003/0114836 A1 6/2003 Estes et al.
2003/0114897 A1 6/2003 Von Arx et al.
2003/0119457 A1 6/2003 Standke
2003/0122021 A1 7/2003 McConnell et al.
2003/0125612 A1 7/2003 Fox et al.
2003/0130616 A1 7/2003 Steil et al.
2003/0134347 A1 7/2003 Heller et al.
2003/0135100 A1 7/2003 Kim et al.
2003/0135333 A1 7/2003 Aceti et al.
2003/0144579 A1 7/2003 Buss
2003/0146841 A1 8/2003 Koenig
2003/0153820 A1 8/2003 Berner et al.
2003/0153821 A1 8/2003 Berner et al.
2003/0158472 A1 8/2003 Sohrab
2003/0158707 A1 8/2003 Doi
2003/0168338 A1 9/2003 Gao et al.
2003/0175806 A1 9/2003 Rule et al.
2003/0175992 A1 9/2003 Toranto et al.
2003/0176183 A1 9/2003 Drucker et al.
2003/0176933 A1 9/2003 Lebel et al.
2003/0181851 A1 9/2003 Mann et al.
2003/0181852 A1 9/2003 Mann et al.
2003/0187338 A1 10/2003 Say et al.
2003/0187525 A1 10/2003 Mann et al.
2003/0191376 A1 10/2003 Samuels et al.
2003/0191431 A1 10/2003 Mann et al.
2003/0195403 A1 10/2003 Berner et al.
2003/0195462 A1 10/2003 Mann et al.
2003/0199790 A1 10/2003 Boecker et al.
2003/0199791 A1 10/2003 Boecker et al.
2003/0199903 A1 10/2003 Boecker et al.
2003/0203498 A1 10/2003 Neel et al.
2003/0204290 A1 10/2003 Sadler et al.
2003/0208110 A1 11/2003 Mault et al.
2003/0208113 A1 11/2003 Mault et al.
2003/0208114 A1 11/2003 Ackerman
2003/0208133 A1 11/2003 Mault
2003/0208409 A1 11/2003 Mault
2003/0212317 A1 11/2003 Kovatchev et al.
2003/0212364 A1 11/2003 Mann et al.
2003/0212379 A1 11/2003 Bylund et al.
2003/0212579 A1 11/2003 Brown et al.
2003/0216628 A1* 11/2003 Bortz .................... G16H 50/20 702/22
2003/0216630 A1 11/2003 Jersey-Willuhn et al.
2003/0217966 A1 11/2003 Tapsak et al.
2003/0226695 A1 12/2003 Mault
2003/0229514 A2 12/2003 Brown
2003/0232370 A1 12/2003 Trifiro
2003/0235817 A1 12/2003 Bartkowiak et al.
2004/0010207 A1 1/2004 Flaherty et al.
2004/0011671 A1 1/2004 Shults et al.
2004/0017300 A1 1/2004 Kotzin et al.
2004/0018486 A1 1/2004 Dunn et al.

(56) References Cited

U.S. PATENT DOCUMENTS

2004/0030226 A1 2/2004 Quy
2004/0030531 A1 2/2004 Miller et al.
2004/0030581 A1 2/2004 Levin et al.
2004/0034289 A1 2/2004 Teller et al.
2004/0039255 A1 2/2004 Simonsen et al.
2004/0039256 A1 2/2004 Kawatahara et al.
2004/0039298 A1 2/2004 Abreu et al.
2004/0040840 A1 3/2004 Mao et al.
2004/0044272 A1* 3/2004 Moerman ................ A61P 7/04 600/300
2004/0045879 A1 3/2004 Shults et al.
2004/0054263 A1 3/2004 Moerman et al.
2004/0059201 A1 3/2004 Ginsberg
2004/0063435 A1 4/2004 Sakamoto et al.
2004/0064068 A1 4/2004 DeNuzzio et al.
2004/0069164 A1 4/2004 Nakamura et al.
2004/0072357 A1 4/2004 Stiene et al.
2004/0073095 A1 4/2004 Causey, III et al.
2004/0096959 A1 5/2004 Stiene et al.
2004/0100376 A1 5/2004 Lye et al.
2004/0105411 A1 6/2004 Boatwright et al.
2004/0106858 A1 6/2004 Say et al.
2004/0106859 A1 6/2004 Say et al.
2004/0108226 A1 6/2004 Polychronakos et al.
2004/0116786 A1 6/2004 Iijima et al.
2004/0122353 A1 6/2004 Shahmirian et al.
2004/0122489 A1 6/2004 Mazar et al.
2004/0122530 A1 6/2004 Hansen et al.
2004/0133164 A1 7/2004 Funderburk et al.
2004/0133390 A1 7/2004 Osorio et al.
2004/0138588 A1 7/2004 Saikley et al.
2004/0146909 A1 7/2004 Duong et al.
2004/0147872 A1 7/2004 Thompson
2004/0152622 A1 8/2004 Keith et al.
2004/0152961 A1 8/2004 Carlson et al.
2004/0153585 A1 8/2004 Kawatahara et al.
2004/0162473 A1 8/2004 Sohrab
2004/0164961 A1 8/2004 Bal et al.
2004/0167383 A1 8/2004 Kim et al.
2004/0167464 A1 8/2004 Ireland et al.
2004/0167801 A1 8/2004 Say et al.
2004/0171921 A1 9/2004 Say et al.
2004/0172284 A1 9/2004 Sullivan et al.
2004/0176672 A1 9/2004 Silver et al.
2004/0176913 A1 9/2004 Kawatahara et al.
2004/0186362 A1 9/2004 Brauker et al.
2004/0186365 A1 9/2004 Jin et al.
2004/0193025 A1 9/2004 Steil et al.
2004/0193090 A1 9/2004 Lebel et al.
2004/0197846 A1 10/2004 Hockersmith et al.
2004/0199056 A1 10/2004 Husemann et al.
2004/0199059 A1 10/2004 Brauker et al.
2004/0202576 A1 10/2004 Aceti et al.
2004/0204687 A1 10/2004 Mogensen et al.
2004/0204868 A1 10/2004 Maynard et al.
2004/0206916 A1 10/2004 Colvin, Jr. et al.
2004/0208780 A1 10/2004 Faries, Jr. et al.
2004/0212536 A1 10/2004 Mori et al.
2004/0216740 A1 11/2004 Remmers et al.
2004/0221057 A1 11/2004 Darcey et al.
2004/0225338 A1 11/2004 Lebel et al.
2004/0235446 A1 11/2004 Flaherty et al.
2004/0236200 A1 11/2004 Say et al.
2004/0248204 A1 12/2004 Moerman
2004/0249250 A1 12/2004 McGee et al.
2004/0249253 A1 12/2004 Racchini et al.
2004/0249254 A1 12/2004 Racchini et al.
2004/0249999 A1 12/2004 Connolly et al.
2004/0253736 A1 12/2004 Stout et al.
2004/0254429 A1 12/2004 Yang
2004/0254433 A1 12/2004 Bandis et al.
2004/0254434 A1 12/2004 Goodnow et al.
2004/0260363 A1 12/2004 Arx et al.
2004/0260478 A1 12/2004 Schwamm
2004/0263354 A1 12/2004 Mann et al.
2004/0267300 A1 12/2004 Mace
2005/0001024 A1 1/2005 Kusaka et al.
2005/0003470 A1 1/2005 Nelson et al.
2005/0004439 A1 1/2005 Shin et al.
2005/0004494 A1 1/2005 Perez et al.
2005/0010087 A1 1/2005 Banet et al.
2005/0010269 A1 1/2005 Lebel et al.
2005/0016276 A1 1/2005 Guan et al.
2005/0017864 A1 1/2005 Tsoukalis
2005/0027177 A1 2/2005 Shin et al.
2005/0027179 A1 2/2005 Berner et al.
2005/0027180 A1 2/2005 Goode, Jr. et al.
2005/0027181 A1 2/2005 Goode, Jr. et al.
2005/0027462 A1 2/2005 Goode, Jr. et al.
2005/0027463 A1 2/2005 Goode, Jr. et al.
2005/0031689 A1 2/2005 Shults et al.
2005/0033132 A1 2/2005 Shults et al.
2005/0038332 A1 2/2005 Saidara et al.
2005/0038680 A1 2/2005 McMahon
2005/0043598 A1 2/2005 Goode, Jr. et al.
2005/0043894 A1 2/2005 Fernandez
2005/0049179 A1 3/2005 Davidson et al.
2005/0049473 A1 3/2005 Desai et al.
2005/0054909 A1 3/2005 Petisce et al.
2005/0059372 A1 3/2005 Arayashiki et al.
2005/0065464 A1 3/2005 Talbot et al.
2005/0070777 A1 3/2005 Cho et al.
2005/0075822 A1 4/2005 Shimizu
2005/0090607 A1 4/2005 Tapsak et al.
2005/0096511 A1 5/2005 Fox et al.
2005/0096512 A1 5/2005 Fox et al.
2005/0096516 A1 5/2005 Soykan et al.
2005/0112169 A1 5/2005 Brauker et al.
2005/0112544 A1 5/2005 Xu et al.
2005/0113653 A1 5/2005 Fox et al.
2005/0113657 A1 5/2005 Alarcon et al.
2005/0113658 A1 5/2005 Jacobson et al.
2005/0113886 A1 5/2005 Fischell et al.
2005/0114068 A1 5/2005 Chey et al.
2005/0116683 A1 6/2005 Cheng et al.
2005/0118726 A1 6/2005 Schultz et al.
2005/0121322 A1 6/2005 Say et al.
2005/0124873 A1 6/2005 Shults et al.
2005/0131346 A1 6/2005 Douglas
2005/0137471 A1 6/2005 Haar et al.
2005/0137530 A1 6/2005 Campbell et al.
2005/0143635 A1 6/2005 Kamath et al.
2005/0143636 A1 6/2005 Zhang et al.
2005/0148003 A1 7/2005 Kieth et al.
2005/0154271 A1 7/2005 Rasdal et al.
2005/0161346 A1 7/2005 Simpson et al.
2005/0171503 A1 8/2005 Van Den Berghe et al.
2005/0171513 A1 8/2005 Mann et al.
2005/0173245 A1 8/2005 Feldman et al.
2005/0176136 A1 8/2005 Burd et al.
2005/0177036 A1 8/2005 Shults et al.
2005/0177398 A1 8/2005 Watanabe et al.
2005/0181012 A1 8/2005 Saint et al.
2005/0182306 A1 8/2005 Sloan
2005/0182358 A1 8/2005 Veit et al.
2005/0182451 A1 8/2005 Griffin et al.
2005/0187442 A1 8/2005 Cho et al.
2005/0187720 A1 8/2005 Goode et al.
2005/0192494 A1 9/2005 Ginsberg
2005/0192557 A1* 9/2005 Brauker .............. A61B 5/4839 604/503
2005/0195930 A1 9/2005 Spital et al.
2005/0199494 A1 9/2005 Say et al.
2005/0203360 A1 9/2005 Brauker et al.
2005/0203707 A1 9/2005 Tsutsui et al.
2005/0204134 A1 9/2005 Von Arx et al.
2005/0214892 A1 9/2005 Kovatchev et al.
2005/0215871 A1 9/2005 Feldman et al.
2005/0215872 A1 9/2005 Berner et al.
2005/0221504 A1 10/2005 Petruno et al.
2005/0236361 A1 10/2005 Ufer et al.
2005/0239154 A1 10/2005 Feldman et al.
2005/0239156 A1 10/2005 Drucker et al.
2005/0241957 A1 11/2005 Mao et al.

(56) References Cited

U.S. PATENT DOCUMENTS

2005/0245795 A1 11/2005 Goode, Jr. et al.
2005/0245799 A1 11/2005 Brauker et al.
2005/0245839 A1 11/2005 Stivoric et al.
2005/0245904 A1 11/2005 Estes et al.
2005/0251033 A1 11/2005 Scarantino et al.
2005/0251083 A1 11/2005 Carr-Brendel et al.
2005/0261660 A1 11/2005 Choi
2005/0267780 A1 12/2005 Ray et al.
2005/0271546 A1 12/2005 Gelber et al.
2005/0271547 A1 12/2005 Gelber et al.
2005/0272640 A1 12/2005 Doyle, III et al.
2005/0272985 A1 12/2005 Kotulla et al.
2005/0277164 A1 12/2005 Drucker et al.
2005/0277912 A1 12/2005 John
2005/0287620 A1 12/2005 Heller et al.
2006/0001538 A1 1/2006 Kraft et al.
2006/0001550 A1 1/2006 Mann et al.
2006/0001551 A1 1/2006 Kraft et al.
2006/0003398 A1 1/2006 Heller et al.
2006/0004270 A1 1/2006 Bedard et al.
2006/0004271 A1 1/2006 Peyser et al.
2006/0007017 A1 1/2006 Mann et al.
2006/0015020 A1 1/2006 Neale et al.
2006/0015024 A1 1/2006 Brister et al.
2006/0016700 A1 1/2006 Brister et al.
2006/0019327 A1 1/2006 Brister et al.
2006/0020186 A1 1/2006 Brister et al.
2006/0020187 A1 1/2006 Brister et al.
2006/0020188 A1 1/2006 Kamath et al.
2006/0020189 A1 1/2006 Brister et al.
2006/0020190 A1 1/2006 Kamath et al.
2006/0020191 A1 1/2006 Brister et al.
2006/0020192 A1 1/2006 Brister et al.
2006/0020300 A1 1/2006 Nghiem et al.
2006/0025663 A1 2/2006 Talbot et al.
2006/0029177 A1 2/2006 Cranford et al.
2006/0031094 A1 2/2006 Cohen et al.
2006/0031440 A1 2/2006 Ashley
2006/0036139 A1 2/2006 Brister et al.
2006/0036140 A1 2/2006 Brister et al.
2006/0036141 A1 2/2006 Kamath et al.
2006/0036142 A1 2/2006 Brister et al.
2006/0036143 A1 2/2006 Brister et al.
2006/0036144 A1 2/2006 Brister et al.
2006/0036145 A1 2/2006 Brister et al.
2006/0036187 A1 2/2006 Vos et al.
2006/0040402 A1 2/2006 Brauker et al.
2006/0052679 A1 3/2006 Kotulla et al.
2006/0058588 A1 3/2006 Zdeblick
2006/0058602 A1 3/2006 Kwiatkowski et al.
2006/0063218 A1 3/2006 Bartkowiak et al.
2006/0074564 A1 4/2006 Bartowiak et al.
2006/0129733 A1 6/2006 Solbelman
2006/0142651 A1 6/2006 Brister et al.
2006/0154642 A1 7/2006 Scannell
2006/0155180 A1 7/2006 Brister et al.
2006/0166629 A1 7/2006 Reggiardo
2006/0173260 A1 8/2006 Gaoni et al.
2006/0173406 A1 8/2006 Hayes et al.
2006/0173444 A1 8/2006 Choy et al.
2006/0183985 A1 8/2006 Brister et al.
2006/0189863 A1 8/2006 Peyser et al.
2006/0193375 A1 8/2006 Lee et al.
2006/0195029 A1 8/2006 Shults et al.
2006/0200112 A1 9/2006 Paul
2006/0202859 A1 9/2006 Mastrototaro et al.
2006/0222566 A1 10/2006 Brauker et al.
2006/0224109 A1 10/2006 Steil et al.
2006/0224141 A1 10/2006 Rush et al.
2006/0226985 A1 10/2006 Goodnow et al.
2006/0229512 A1 10/2006 Petisce et al.
2006/0247508 A1 11/2006 Fennell
2006/0247985 A1 11/2006 Liamos et al.
2006/0253296 A1 11/2006 Liisberg et al.
2006/0258918 A1 11/2006 Burd et al.
2006/0258929 A1 11/2006 Goode et al.
2006/0263763 A1 11/2006 Simpson et al.
2006/0264785 A1 11/2006 Dring et al.
2006/0264888 A1 11/2006 Moberg et al.
2006/0270922 A1 11/2006 Brauker et al.
2006/0272652 A1 12/2006 Stocker et al.
2006/0276771 A1 12/2006 Galley et al.
2006/0290496 A1 12/2006 Peeters et al.
2006/0293607 A1 12/2006 Alt et al.
2007/0007133 A1 1/2007 Mang et al.
2007/0016381 A1 1/2007 Kamath et al.
2007/0017983 A1 1/2007 Frank et al.
2007/0026440 A1 2/2007 Broderick et al.
2007/0027381 A1 2/2007 Stafford
2007/0032706 A1 2/2007 Kamath et al.
2007/0033074 A1 2/2007 Nitzan et al.
2007/0038044 A1 2/2007 Dobbles et al.
2007/0045759 A1 3/2007 Chung et al.
2007/0060802 A1 3/2007 Ghevondian et al.
2007/0060814 A1 3/2007 Stafford
2007/0060869 A1 3/2007 Tolle et al.
2007/0066873 A1 3/2007 Kamath et al.
2007/0071681 A1 3/2007 Gadkar et al.
2007/0073129 A1 3/2007 Shah et al.
2007/0078320 A1 4/2007 Stafford
2007/0078321 A1 4/2007 Mazza et al.
2007/0078322 A1 4/2007 Stafford
2007/0078323 A1 4/2007 Reggiardo et al.
2007/0090511 A1 4/2007 Borland et al.
2007/0093786 A1 4/2007 Goldsmith et al.
2007/0100222 A1 5/2007 Mastrototaro et al.
2007/0106135 A1 5/2007 Sloan et al.
2007/0124002 A1 5/2007 Estes et al.
2007/0149873 A1 6/2007 Say et al.
2007/0149874 A1 6/2007 Say et al.
2007/0151869 A1 7/2007 Heller et al.
2007/0153705 A1 7/2007 Rosar et al.
2007/0156094 A1 7/2007 Safabash et al.
2007/0161879 A1 7/2007 Say et al.
2007/0161880 A1 7/2007 Say et al.
2007/0163880 A1 7/2007 Woo et al.
2007/0168224 A1 7/2007 Letzt et al.
2007/0173706 A1 7/2007 Neinast et al.
2007/0173712 A1 7/2007 Shah et al.
2007/0173761 A1 7/2007 Kanderian et al.
2007/0179349 A1 8/2007 Hoyme et al.
2007/0179352 A1 8/2007 Randlov et al.
2007/0179370 A1 8/2007 Say et al.
2007/0179372 A1 8/2007 Say et al.
2007/0191699 A1 8/2007 Say et al.
2007/0191700 A1 8/2007 Say et al.
2007/0191702 A1 8/2007 Yodfat et al.
2007/0203408 A1 8/2007 Say et al.
2007/0203410 A1 8/2007 Say et al.
2007/0203411 A1 8/2007 Say et al.
2007/0203966 A1 8/2007 Brauker et al.
2007/0208244 A1 9/2007 Brauker et al.
2007/0208247 A1 9/2007 Say et al.
2007/0213610 A1 9/2007 Say et al.
2007/0213657 A1 9/2007 Jennewine et al.
2007/0215491 A1 9/2007 Heller et al.
2007/0218097 A1 9/2007 Heller et al.
2007/0219496 A1 9/2007 Kamen et al.
2007/0222609 A1 9/2007 Duron et al.
2007/0235331 A1 10/2007 Simpson et al.
2007/0244380 A1 10/2007 Say et al.
2007/0249919 A1 10/2007 Say et al.
2007/0249920 A1 10/2007 Say et al.
2007/0249922 A1 10/2007 Peyser et al.
2007/0255321 A1 11/2007 Gelber et al.
2007/0255348 A1 11/2007 Holtzclaw
2007/0271285 A1 11/2007 Eichorn et al.
2007/0282299 A1 12/2007 Hellwig
2007/0299617 A1 12/2007 Willis
2008/0009304 A1 1/2008 Fry
2008/0009692 A1 1/2008 Stafford
2008/0021666 A1 1/2008 Goode et al.
2008/0027586 A1 1/2008 Hem et al.
2008/0033254 A1 2/2008 Kamath et al.

(56) References Cited

U.S. PATENT DOCUMENTS

2008/0039702 A1 2/2008 Hayter et al.
2008/0045824 A1 2/2008 Tapsak et al.
2008/0055070 A1 3/2008 Bange et al.
2008/0057484 A1 3/2008 Miyata et al.
2008/0058626 A1 3/2008 Miyata et al.
2008/0058678 A1 3/2008 Miyata et al.
2008/0060955 A1 3/2008 Goodnow
2008/0062055 A1 3/2008 Cunningham et al.
2008/0067627 A1 3/2008 Boeck et al.
2008/0071156 A1 3/2008 Brister et al.
2008/0083617 A1 4/2008 Simpson et al.
2008/0086042 A1 4/2008 Brister et al.
2008/0086044 A1 4/2008 Brister et al.
2008/0086273 A1 4/2008 Shults et al.
2008/0092638 A1 4/2008 Brenneman et al.
2008/0097289 A1 4/2008 Steil et al.
2008/0108942 A1 5/2008 Brister et al.
2008/0119710 A1 5/2008 Reggiardo et al.
2008/0154513 A1 6/2008 Kovatchev et al.
2008/0167543 A1 7/2008 Say et al.
2008/0172205 A1 7/2008 Breton et al.
2008/0183060 A1 7/2008 Steil et al.
2008/0183061 A1 7/2008 Goode et al.
2008/0183399 A1 7/2008 Goode et al.
2008/0188731 A1 8/2008 Brister et al.
2008/0188796 A1 8/2008 Steil et al.
2008/0189051 A1 8/2008 Goode et al.
2008/0194934 A1 8/2008 Ray et al.
2008/0194935 A1 8/2008 Brister et al.
2008/0194936 A1 8/2008 Goode et al.
2008/0194937 A1 8/2008 Goode et al.
2008/0194938 A1 8/2008 Brister et al.
2008/0195232 A1 8/2008 Carr-Brendel et al.
2008/0195967 A1 8/2008 Goode et al.
2008/0197024 A1 8/2008 Simpson et al.
2008/0200788 A1 8/2008 Brister et al.
2008/0200789 A1 8/2008 Brister et al.
2008/0200791 A1 8/2008 Simpson et al.
2008/0208025 A1 8/2008 Shults et al.
2008/0208113 A1 8/2008 Damian et al.
2008/0214915 A1 9/2008 Brister et al.
2008/0214918 A1 9/2008 Brister et al.
2008/0228051 A1 9/2008 Shults et al.
2008/0228054 A1 9/2008 Shults et al.
2008/0234943 A1 9/2008 Ray et al.
2008/0235053 A1 9/2008 Ray et al.
2008/0242961 A1 10/2008 Brister et al.
2008/0254544 A1 10/2008 Modzelewski et al.
2008/0262469 A1 10/2008 Brister et al.
2008/0267823 A1 10/2008 Wang et al.
2008/0275313 A1 11/2008 Brister et al.
2008/0287764 A1 11/2008 Rasdal et al.
2008/0287765 A1 11/2008 Rasdal et al.
2008/0287766 A1 11/2008 Rasdal et al.
2008/0296155 A1 12/2008 Shults et al.
2008/0300572 A1 12/2008 Rankers et al.
2008/0300919 A1 12/2008 Charlton et al.
2008/0300920 A1 12/2008 Brown et al.
2008/0301158 A1 12/2008 Brown et al.
2008/0301665 A1 12/2008 Charlton et al.
2008/0306368 A1 12/2008 Goode et al.
2008/0306434 A1 12/2008 Dobbles et al.
2008/0306435 A1 12/2008 Kamath et al.
2008/0306444 A1 12/2008 Brister et al.
2008/0312859 A1 12/2008 Skyggebjerg et al.
2009/0006133 A1 1/2009 Weinert et al.
2009/0012379 A1 1/2009 Goode et al.
2009/0018424 A1 1/2009 Kamath et al.
2009/0030294 A1 1/2009 Petisce et al.
2009/0036758 A1 2/2009 Brauker et al.
2009/0036763 A1 2/2009 Brauker et al.
2009/0040022 A1 2/2009 Finkenzeller
2009/0043181 A1 2/2009 Brauker et al.
2009/0043182 A1 2/2009 Brauker et al.
2009/0043525 A1 2/2009 Brauker et al.
2009/0043541 A1 2/2009 Brauker et al.
2009/0043542 A1 2/2009 Brauker et al.
2009/0045055 A1 2/2009 Rhodes et al.
2009/0048503 A1 2/2009 Dalal et al.
2009/0054747 A1 2/2009 Fennell
2009/0055149 A1 2/2009 Hayter et al.
2009/0062633 A1 3/2009 Brauker et al.
2009/0062635 A1 3/2009 Brauker et al.
2009/0062767 A1 3/2009 VanAntwerp et al.
2009/0076356 A1 3/2009 Simpson et al.
2009/0076360 A1 3/2009 Brister et al.
2009/0076361 A1 3/2009 Kamath et al.
2009/0085873 A1 4/2009 Betts et al.
2009/0099436 A1 4/2009 Brister et al.
2009/0105560 A1 4/2009 Solomon
2009/0124877 A1 5/2009 Goode et al.
2009/0124878 A1 5/2009 Goode et al.
2009/0124879 A1 5/2009 Brister et al.
2009/0124964 A1 5/2009 Leach et al.
2009/0131768 A1 5/2009 Simpson et al.
2009/0131769 A1 5/2009 Leach et al.
2009/0131776 A1 5/2009 Simpson et al.
2009/0131777 A1 5/2009 Simpson et al.
2009/0137886 A1 5/2009 Shariati et al.
2009/0137887 A1 5/2009 Shariati et al.
2009/0143659 A1 6/2009 Li et al.
2009/0143660 A1 6/2009 Brister et al.
2009/0149717 A1 6/2009 Brauer et al.
2009/0156919 A1 6/2009 Brister et al.
2009/0156924 A1 6/2009 Shariati et al.
2009/0163790 A1 6/2009 Brister et al.
2009/0163791 A1 6/2009 Brister et al.
2009/0178459 A1 7/2009 Li et al.
2009/0182217 A1 7/2009 Li et al.
2009/0192366 A1 7/2009 Mensinger et al.
2009/0192380 A1 7/2009 Shariati et al.
2009/0192722 A1 7/2009 Shariati et al.
2009/0192724 A1 7/2009 Brauker et al.
2009/0192745 A1 7/2009 Kamath et al.
2009/0192751 A1 7/2009 Kamath et al.
2009/0203981 A1 8/2009 Brauker et al.
2009/0204340 A1 8/2009 Feldman et al.
2009/0204341 A1 8/2009 Brauker et al.
2009/0216100 A1 8/2009 Ebner et al.
2009/0216102 A1 8/2009 Say et al.
2009/0216103 A1 8/2009 Brister et al.
2009/0221890 A1 9/2009 Saffer et al.
2009/0240120 A1 9/2009 Mensinger et al.
2009/0240128 A1 9/2009 Mensinger et al.
2009/0240193 A1 9/2009 Mensinger et al.
2009/0242399 A1 10/2009 Kamath et al.
2009/0242425 A1 10/2009 Kamath et al.
2009/0247855 A1 10/2009 Boock et al.
2009/0247856 A1 10/2009 Boock et al.
2009/0253973 A1 10/2009 Bashan et al.
2009/0287073 A1 11/2009 Boock et al.
2009/0287074 A1 11/2009 Shults et al.
2009/0298182 A1 12/2009 Schulat et al.
2009/0299155 A1 12/2009 Yang et al.
2009/0299156 A1 12/2009 Simpson et al.
2009/0299162 A1 12/2009 Brauker et al.
2009/0299276 A1 12/2009 Brauker et al.
2010/0010324 A1 1/2010 Brauker et al.
2010/0010329 A1 1/2010 Taub et al.
2010/0010331 A1 1/2010 Brauker et al.
2010/0010332 A1 1/2010 Brauker et al.
2010/0016687 A1 1/2010 Brauker et al.
2010/0016698 A1 1/2010 Rasdal et al.
2010/0022855 A1 1/2010 Brauker et al.
2010/0025238 A1 2/2010 Gottlieb et al.
2010/0030038 A1 2/2010 Brauker et al.
2010/0030053 A1 2/2010 Goode, Jr. et al.
2010/0030484 A1 2/2010 Brauker et al.
2010/0030485 A1 2/2010 Brauker et al.
2010/0036215 A1 2/2010 Goode, Jr. et al.
2010/0036216 A1 2/2010 Goode, Jr. et al.
2010/0036222 A1 2/2010 Goode, Jr. et al.
2010/0036223 A1 2/2010 Goode, Jr. et al.
2010/0036225 A1 2/2010 Goode, Jr. et al.

(56) References Cited

U.S. PATENT DOCUMENTS

| | | | |
|---|---|---|---|
| 2010/0041971 | A1 | 2/2010 | Goode, Jr. et al. |
| 2010/0045465 | A1 | 2/2010 | Brauker et al. |
| 2010/0049024 | A1 | 2/2010 | Saint et al. |
| 2010/0063373 | A1 | 3/2010 | Kamath et al. |
| 2010/0076283 | A1 | 3/2010 | Simpson et al. |
| 2010/0081908 | A1 | 4/2010 | Dobbles et al. |
| 2010/0081910 | A1 | 4/2010 | Brister et al. |
| 2010/0087724 | A1 | 4/2010 | Brauker et al. |
| 2010/0096259 | A1 | 4/2010 | Zhang et al. |
| 2010/0099970 | A1 | 4/2010 | Shults et al. |
| 2010/0099971 | A1 | 4/2010 | Shults et al. |
| 2010/0105999 | A1 | 4/2010 | Dixon et al. |
| 2010/0119693 | A1 | 5/2010 | Tapsak et al. |
| 2010/0119881 | A1 | 5/2010 | Patel et al. |
| 2010/0121169 | A1 | 5/2010 | Petisce et al. |
| 2010/0152554 | A1 | 6/2010 | Steine et al. |
| 2010/0160759 | A1 | 6/2010 | Celentano et al. |
| 2010/0161236 | A1 | 6/2010 | Cohen et al. |
| 2010/0168538 | A1 | 7/2010 | Keenan et al. |
| 2010/0174266 | A1 | 7/2010 | Estes |
| 2010/0185175 | A1 | 7/2010 | Kamen et al. |
| 2010/0191472 | A1 | 7/2010 | Doniger et al. |
| 2010/0198142 | A1 | 8/2010 | Sloan et al. |
| 2010/0198314 | A1 | 8/2010 | Wei |
| 2010/0213080 | A1 | 8/2010 | Celentano et al. |
| 2010/0235439 | A1 | 9/2010 | Goodnow et al. |
| 2010/0267161 | A1 | 10/2010 | Wu et al. |
| 2010/0312176 | A1 | 12/2010 | Lauer et al. |
| 2010/0313105 | A1 | 12/2010 | Nekoomaram et al. |
| 2010/0324403 | A1 | 12/2010 | Brister et al. |
| 2011/0031986 | A1 | 2/2011 | Bhat et al. |
| 2011/0077494 | A1 | 3/2011 | Doniger et al. |
| 2011/0124996 | A1 | 5/2011 | Reinke et al. |
| 2011/0125040 | A1 | 5/2011 | Crawford et al. |
| 2011/0148905 | A1 | 6/2011 | Simmons et al. |
| 2011/0208027 | A1 | 8/2011 | Wagner et al. |
| 2011/0230741 | A1 | 9/2011 | Liang et al. |
| 2011/0251472 | A1 | 10/2011 | Weinert et al. |
| 2011/0257895 | A1 | 10/2011 | Brauker et al. |
| 2011/0287528 | A1 | 11/2011 | Fern et al. |
| 2012/0190989 | A1 | 7/2012 | Kaiser et al. |
| 2013/0035575 | A1 | 2/2013 | Mayou et al. |
| 2013/0235166 | A1 | 9/2013 | Jones et al. |

FOREIGN PATENT DOCUMENTS

| | | | |
|---|---|---|---|
| DE | 3934299 | C1 | 10/1990 |
| DE | 4234553 | | 1/1995 |
| DE | 4401400 | A1 | 7/1995 |
| EP | 0010375 | | 4/1980 |
| EP | 0026995 | A1 | 4/1981 |
| EP | 0048090 | A2 | 3/1982 |
| EP | 0078636 | A1 | 5/1983 |
| EP | 0080304 | A1 | 6/1983 |
| EP | 0096228 | A2 | 12/1983 |
| EP | 0096288 | A1 | 12/1983 |
| EP | 0098592 | | 1/1984 |
| EP | 0125139 | | 11/1984 |
| EP | 0127958 | | 12/1984 |
| EP | 0136362 | | 4/1985 |
| EP | 0170375 | A2 | 2/1986 |
| EP | 0177743 | A2 | 4/1986 |
| EP | 0184909 | | 6/1986 |
| EP | 0206218 | A2 | 12/1986 |
| EP | 0230472 | A1 | 8/1987 |
| EP | 0241309 | | 10/1987 |
| EP | 0245073 | A2 | 11/1987 |
| EP | 0255291 | | 2/1988 |
| EP | 0278647 | | 8/1988 |
| EP | 0286118 | A2 | 10/1988 |
| EP | 0320109 | | 6/1989 |
| EP | 0353328 | A1 | 2/1990 |
| EP | 0359831 | A1 | 3/1990 |
| EP | 0368209 | | 5/1990 |
| EP | 0368290 | | 5/1990 |
| EP | 0390390 | | 10/1990 |
| EP | 0396788 | | 11/1990 |
| EP | 0400918 | A1 | 12/1990 |
| EP | 0453283 | A1 | 10/1991 |
| EP | 0470290 | | 2/1992 |
| EP | 0504835 | | 9/1992 |
| EP | 0286118 | B1 | 1/1995 |
| EP | 0653718 | | 5/1995 |
| EP | 0680727 | | 11/1995 |
| EP | 0800082 | A2 | 10/1997 |
| EP | 0880936 | | 12/1998 |
| EP | 0970655 | | 1/2000 |
| EP | 1034734 | | 9/2000 |
| EP | 1048264 | A1 | 11/2000 |
| EP | 1281351 | | 2/2003 |
| EP | 1445746 | A1 | 8/2004 |
| EP | 1568309 | | 8/2005 |
| EP | 1579690 | A1 | 9/2005 |
| EP | 1956371 | | 8/2008 |
| EP | 2260757 | | 12/2010 |
| EP | 1413245 | | 6/2011 |
| GB | 1394171 | | 5/1975 |
| GB | 1579690 | | 11/1980 |
| GB | 1599241 | A | 9/1981 |
| GB | 2073891 | | 10/1981 |
| GB | 2154003 | | 8/1985 |
| GB | 2194892 | | 3/1988 |
| GB | 2204408 | | 11/1988 |
| GB | 2225637 | | 6/1990 |
| GB | 2254436 | | 10/1992 |
| JP | 54-041191 | | 4/1979 |
| JP | 55-012406 | | 1/1980 |
| JP | 56-163447 | | 12/1981 |
| JP | 57-070448 | | 4/1982 |
| JP | 60-173457 | | 9/1985 |
| JP | 60-173458 | | 9/1985 |
| JP | 60-173459 | | 9/1985 |
| JP | 60-210243 | | 10/1985 |
| JP | 61-090050 | | 5/1986 |
| JP | 62-085855 | | 4/1987 |
| JP | 62-114747 | | 5/1987 |
| JP | 63-058149 | | 3/1988 |
| JP | 63-128252 | | 5/1988 |
| JP | 63-139246 | | 6/1988 |
| JP | 63-294799 | | 12/1988 |
| JP | 63-317757 | | 12/1988 |
| JP | 63-317758 | | 12/1988 |
| JP | 1-114746 | | 5/1989 |
| JP | 1-114747 | | 5/1989 |
| JP | 1-124060 | | 5/1989 |
| JP | 1-134244 | | 5/1989 |
| JP | 1-156658 | | 6/1989 |
| JP | 2-062958 | | 3/1990 |
| JP | 2-120655 | | 5/1990 |
| JP | 2-287145 | | 11/1990 |
| JP | 2-310457 | | 12/1990 |
| JP | 3-026956 | | 2/1991 |
| JP | 3-028752 | | 2/1991 |
| JP | 3-202764 | | 9/1991 |
| JP | 5-072171 | | 3/1993 |
| JP | 5-196595 | | 8/1993 |
| JP | 6-190050 | | 7/1994 |
| JP | 7-055757 | | 3/1995 |
| JP | 7-072585 | | 3/1995 |
| JP | 8-154903 | | 6/1996 |
| JP | 8-285814 | | 11/1996 |
| JP | 8-285815 | | 11/1996 |
| JP | 9-021778 | | 1/1997 |
| JP | 9-101280 | | 4/1997 |
| JP | 9-285459 | | 11/1997 |
| JP | 10-170471 | | 6/1998 |
| JP | 2000-000231 | | 1/2000 |
| JP | 2000-116628 | | 4/2000 |
| SU | 1281988 | | 1/1987 |
| WO | WO-8505119 | A1 | 11/1985 |
| WO | WO-1986/000513 | | 1/1986 |
| WO | WO-8700513 | A1 | 1/1987 |
| WO | WO-1987/006040 | | 10/1987 |
| WO | WO-8902246 | A1 | 3/1989 |

(56) References Cited

FOREIGN PATENT DOCUMENTS

WO WO-1989/005119 6/1989
WO WO-8908713 A1 9/1989
WO WO-1990/000367 1/1990
WO WO-1990/005300 5/1990
WO WO-9005910 A1 5/1990
WO WO-9101680 A1 2/1991
WO WO-9104704 A1 4/1991
WO WO-9115993 A1 10/1991
WO WO-1992/001947 2/1992
WO WO-1992/013271 8/1992
WO WO-1994/020602 9/1994
WO WO-9427140 A1 11/1994
WO WO-1995/028878 2/1995
WO WO-9506240 A1 3/1995
WO WO-9607908 A1 3/1996
WO WO-9625089 A1 8/1996
WO WO-9630431 A1 10/1996
WO WO-9635370 A1 11/1996
WO WO-1997/002847 1/1997
WO WO-9719344 A1 5/1997
WO WO-9720207 A1 6/1997
WO WO-1997/042882 11/1997
WO WO-1997/042886 11/1997
WO WO-1997/042888 11/1997
WO WO-1997/043962 11/1997
WO WO-9741421 A1 11/1997
WO WO-9742883 A1 11/1997
WO WO-9746868 A1 12/1997
WO WO-9809167 A1 3/1998
WO WO-9824366 A2 6/1998
WO WO-1998/035053 8/1998
WO WO-1998/052045 11/1998
WO WO-1998/052293 11/1998
WO WO-1999/005966 2/1999
WO WO-9932883 A2 7/1999
WO WO 99/56613 11/1999
WO WO-2000/013580 3/2000
WO WO-2000/018294 4/2000
WO WO-0019887 A1 4/2000
WO WO-0020626 A1 4/2000
WO WO-2000/033065 6/2000
WO WO-0049940 A2 8/2000
WO WO-2000/059370 10/2000
WO WO-2000/060350 10/2000
WO WO-0062664 A1 10/2000
WO WO-0062665 A1 10/2000
WO WO-2000/074753 12/2000
WO WO-2000/078210 12/2000
WO WO-0078992 A2 12/2000
WO WO-2001/024038 4/2001
WO WO-0133216 A1 5/2001
WO WO-2001/052935 7/2001
WO WO-0152727 A1 7/2001
WO WO-2001/054753 8/2001
WO WO-0157238 A2 8/2001
WO WO-0157239 A2 8/2001
WO WO-2001/067009 9/2001
WO WO-0213686 A1 2/2002
WO WO-0216905 A2 2/2002
WO WO-0217210 A2 2/2002
WO WO-02058537 A2 8/2002
WO WO-02078512 A2 10/2002
WO WO-03036583 A1 5/2003
WO WO-03076893 A2 9/2003
WO WO-2003/080157 10/2003
WO WO-2003/082091 10/2003
WO WO-2003/085372 10/2003
WO WO 2004/009161 1/2004
WO WO-2004/015539 2/2004
WO WO-2004/047445 6/2004
WO WO-2004061420 A2 7/2004
WO WO-2004/098405 11/2004
WO WO-2005089103 A2 9/2005
WO WO-2006/024671 3/2006
WO WO-2006/037109 4/2006
WO WO 2006/064397 6/2006
WO WO 2006/079867 8/2006
WO WO-2006119084 A2 11/2006
WO WO-2007/007459 1/2007
WO WO-2007002189 A2 1/2007
WO WO-2007016399 A2 2/2007
WO WO-2007027381 A1 3/2007
WO WO-2007027788 A2 3/2007
WO WO-2007041069 A2 4/2007
WO WO-2007041070 A2 4/2007
WO WO-2007041248 A2 4/2007
WO WO-2007053832 A2 5/2007
WO WO-2007056638 A2 5/2007
WO WO-2007/065285 6/2007
WO WO-2007120363 A2 10/2007
WO WO-2007/149319 12/2007
WO WO-2007143225 A2 12/2007
WO WO-2008/001366 1/2008
WO WO 2008/030347 3/2008
WO WO-2008/086541 7/2008
WO WO-2008/150428 12/2008
WO WO 2008/151452 12/2008
WO WO-2008/153825 12/2008
WO WO 2009/049252 4/2009
WO WO-2009/075697 6/2009
WO WO 2009/146119 12/2009
WO WO-2010/077329 7/2010
WO WO 2011/041007 4/2011
WO WO 2011/060923 5/2011
WO WO-2011/104616 9/2011

OTHER PUBLICATIONS

"Getting Started with Carelink™ Personal Software for Continuous Glucose Monitoring", User Guide, Medtronic Diabetes, 28 pages (2009).

"In Vivo Glucose Sensing", Chemical Analysis, A Series of Monographs on Analytical Chemistry and its Applications, vol. 174, 466 pages (2010).

"PMA Approvals" retrieved from "https://www.fda.gov/medical-devices/device-approvals-denials-and-clearances/pma-approvals#monthly" on Sep. 14, 2022, 3 pages.

"Premarket Approval (PMA)" retrieved from "https://www.accessdata.fda.gov/scripts/cdrh/cfdocs/cfpma/pma.cfm?ID=P050020" on Sep. 14, 2022, 6 pages.

FreeStyle Navigator Continuous Glucose Monitoring System, User Guide, Abbott Diabetes Care Inc., 195 pages (2008).

Sandham, et al., "Blood Glucose Prediction for Diabetes Therapy Using a Recurrent Artificial Neural Network", 9th European Signal Processing Conference (EUSIPCO 1998), 4 pages (1998).

Sparacino, et al., "Glucose concentration can be predicted ahead in time from continuous glucose monitoring sensor time-series", IEEE Transactions on Biomedical Engineering, 54(5):931-937 (2007).

U.S. Appl. No. 11/267,724 (U.S. Pat. No. 7,766,829), filed Nov. 4, 2005 (Aug. 3, 2010).

U.S. Appl. No. 12/833,975 (U.S. Pat. No. 8,585,591), filed Jul. 10, 2010 (Nov. 19, 2013).

U.S. Appl. No. 14/081,737 (U.S. Pat. No. 9,323,898), filed Nov. 15, 2013 (Apr. 26, 2016).

U.S. Appl. No. 15/071,610 (U.S. Pat. No. 9,669,162), filed Mar. 16, 2016 (Jun. 6, 2017).

U.S. Appl. No. 15/613,713 (Abandoned), filed Jun. 5, 2017.

U.S. Appl. No. 15/880,692 (U.S. Pat. No. 11,538,580), filed Jan. 26, 2018 (Dec. 27, 2022).

U.S. Appl. No. 16/177,811 (Abandoned), filed Nov. 1, 2018.

U.S. Appl. No. 16/177,811, Dec. 22, 2022 Notice of Abandonment.

U.S. Appl. No. 16/177,811, Apr. 14, 2022 Non-Final Office Action.

U.S. Appl. No. 15/880,692, Nov. 10, 2022 Issue Fee Payment.

U.S. Appl. No. 15/880,692, Aug. 11, 2022 Notice of Allowance.

U.S. Appl. No. 15/880,692, Jul. 25, 2022 Amendment and Request for Continued Examination (RCE).

U.S. Appl. No. 15/880,692, Apr. 26, 2022 Notice of Allowance.

U.S. Appl. No. 15/880,692, Apr. 13, 2022 Response to Non-Final Office Action.

(56) References Cited

OTHER PUBLICATIONS

U.S. Appl. No. 15/880,692, Jan. 13, 2022 Non-Final Office Action.
U.S. Appl. No. 15/880,692, Sep. 15, 2021 Request for Continued Examination (RCE).
U.S. Appl. No. 15/880,692, Aug. 23, 2021 Advisory Action.
U.S. Appl. No. 15/880,692, Aug. 23, 2021 After Final Consideration Program Decision.
U.S. Appl. No. 15/880,692, Aug. 16, 2021 Response After Final Action.
U.S. Appl. No. 15/880,692, Aug. 16, 2021 After Final Consideration Program Request.
U.S. Appl. No. 15/880,692, Apr. 15, 2021 Final Office Action.
U.S. Appl. No. 15/880,692, Jan. 5, 2021 Response to Non-Final Office Action.
U.S. Appl. No. 15/880,692, Oct. 1, 2020 Response to Non-Final Office Action.
U.S. Appl. No. 15/613,713, Feb. 6, 2018 Notice of Abandonment.
U.S. Appl. No. 15/613,713, Jul. 28, 2017 Non-Final Office Action.
U.S. Appl. No. 15/071,610, May 1, 2017 Issue Fee Payment.
U.S. Appl. No. 15/071,610, Jan. 30, 2017 Notice of Allowance.
U.S. Appl. No. 15/071,610, filed Jan. 16, 2017 Response After Final Action.
U.S. Appl. No. 15/071,610, Oct. 6, 2016 Final Office Action.
U.S. Appl. No. 15/071,610, Sep. 2, 2016 Response to Non-Final Office Action.
U.S. Appl. No. 15/071,610, Jul. 25, 2016 Applicant Initiated Interview Summary.
U.S. Appl. No. 15/071,610, Jun. 3, 2016 Non-Final Office Action.
U.S. Appl. No. 14/081,737, Mar. 16, 2016 Issue Fee Payment.
U.S. Appl. No. 14/081,737, Dec. 18, 2015 Notice of Allowance.
U.S. Appl. No. 14/081,737, Oct. 30, 2015 Response to Non-Final Office Action.
U.S. Appl. No. 14/081,737, Oct. 22, 2015 Applicant Initiated Interview Summary.
U.S. Appl. No. 14/081,737, May 7, 2015 Non-Final Office Action.
U.S. Appl. No. 12/833,975, Sep. 20, 2013 Issue Fee Payment.
U.S. Appl. No. 12/833,975, Jul. 19, 2013 Notice of Allowance.
U.S. Appl. No. 12/833,975, Jun. 27, 2013 Response to Non-Final Office Action.
U.S. Appl. No. 12/833,975, Apr. 2, 2013 Non-Final Rejection.
U.S. Appl. No. 11/267,724, filed Jun. 15, 2010 Issue Fee Payment.
U.S. Appl. No. 11/267,724, May 13, 2010 Notice of Allowance.
U.S. Appl. No. 11/267,724, Jan. 12, 2010 Request for Continued Examination (RCE).
U.S. Appl. No. 11/267,724, Jan. 5, 2010 Advisory Action.
U.S. Appl. No. 11/267,724, Dec. 14, 2009 Response After Final Action.
U.S. Appl. No. 11/267,724, Oct. 14, 2009 Final Office Action.
U.S. Appl. No. 11/267,724, Jun. 9, 2009 Response to Non-Final Office Action.
U.S. Appl. No. 11/267,724, Jan. 9, 2009 Non-Final Office Action.
U.S. Appl. No. 11/267,724, Sep. 30, 2008 Response to Non-Final Office.
U.S. Appl. No. 11/267,724, Jun. 25, 2008 Response to Non-Final Office Action.
U.S. Appl. No. 11/267,724, Jan. 28, 2008 Non-Final Office Action
U.S. Appl. No. 15/880,692, Oct. 1, 2020 Non-Final Office Action.
U.S. Appl. No. 15/071,610, Jan. 16, 2017 Response After Final Action.
U.S. Appl. No. 11/267,724, Jun. 15, 2010 Issue Fee Payment.
U.S. Appl. No. 11/267,724, Sep. 30, 2008 Response to Non-Final Office Action.
Abruna, H. D., et al., "Rectifying Interfaces Using Two-Layer Films of Electrochemically Polymerized Vinylpyridine and Vinylbipyridine Complexes of Ruthenium and Iron on Electrodes", Journal of the American Chemical Society, vol. 103, No. 1, 1981, pp. 1-5.
Albery, W. J., et al., "Amperometric Enzyme Electrodes Part II: Conducting Salts as Electrode Materials for the Oxidation of Glucose Oxidase", Journal of ElectroAnalytical Chemistry, vol. 194, 1985, pp. 223-235.
Albery, W. J., et al., "Amperometric Enzyme Electrodes", Philosophical Transactions of The Royal Society of London, vol. 316, 1987, pp. 107-119.
Alcock, S. J., et al., "Continuous Analyte Monitoring to Aid Clinical Practice", IEEE Engineering in Medicine and Biology Magazine, 1994, pp. 319-325.
Anderson, L. B., et al., "Thin-Layer Electrochemistry: Steady-State Methods of Studying Rate Processes", Journal of ElectroAnalytical Chemistry, vol. 10, 1965, pp. 295-305.
Armour, J. C., et al., "Application of Chronic Intravascular Blood Glucose Sensor in Dogs", Diabetes, vol. 39, 1990, pp. 1519-1526.
Bartlett, p. N., et al., "Covalent Binding of Electron Relays to Glucose Oxidase", Journal of the Chemical Society, Chemical Communications, 1987, pp. 1603-1604.
Bartlett, P. N., et al., "Modification of Glucose Oxidase by Tetrathiafulvalene", Journal of the Chemical Society, Chemical Communications, 1990, pp. 1135-1136.
Bartlett, P. N., et al., "Strategies for the Development of Amperometric Enzyme Electrodes", Biosensors, vol. 3, 1987/88, pp. 359-379.
Bennion, N., et al., "Alternate Site Glucose Testing: A Crossover Design", Diabetes Technology & Therapeutics, vol. 4, No. 1, 2002, pp. 25-33.
Bergman, R., et al., "Physiological Evaluation of Factors Controlling Glucose Tolerance in Man: Measurement of Insulin Sensitivity and Beta-cell Glucose Sensitivity From the Response to Intravenous Glucose", J. Clin. Invest., The American Society for Clinical Investigation, Inc., vol. 68, 1981, pp. 1456-1467.
Bindra, D. S., et al., "Design and in Vitro Studies of a Needle-Type Glucose Sensor for Subcutaneous Monitoring", Analytical Chemistry. Vol. 63 No. 17, 1991, pp. 1692-1696.
Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.
Bobbioni-Harsch, E., et al., "Lifespan of Subcutaneous Glucose Sensors and Their Performances During Dynamic Glycaemia Changes in Rats", Journal of Biomedical Engineering, vol. 15, 1993, pp. 457-463.
Boedeker Plastics, Inc., "Polyethylene Specifications", Web Page of Boedeker.com, 2007, pp. 1-3.
Brandt, J., et al., "Covalent Attachment of Proteins to Polysaccharide Carriers by Means of Benzoquinone", Biochimica et Biophysica Acta, vol. 386, 1975, pp. 196-202.
Brooks, S. L., et al., "Development of an On-Line Glucose Sensor for Fermentation Monitoring", Biosensors, vol. 3, 1987/88, pp. 45-56.
Brownlee, M., et al., "A Glucose-Controlled Insulin-Delivery System: Semisynthetic Insulin Bound to Lectin", Science, vol. 206, 1979, 1190-1191.
Cass, A. E., et al., "Ferricinum Ion as an Electron Acceptor for Oxido-Reductases", Journal of ElectroAnalytical Chemistry, vol. 190, 1985, pp. 117-127.
Cass, A. E., et al., "Ferrocene-Medicated Enzyme Electrode for Amperometric Determination of Glucose", Analytical Chemistry, vol. 56, No. 4, 1984, 667-671.
Castner, J. F., et al., "Mass Transport and Reaction Kinetic Parameters Determined Electrochemically for Immobilized Glucose Oxidase", Biochemistry, vol. 23 No. 10, 1984, 2203- 2210.
Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.
Claremont, D. J., et al., "Biosensors for Continuous In Vivo Glucose Monitoring", Proceedings of the Annual International Conference of the IEEE Engineering in Medicine and Biology Society, vol. 10, 1988.
Clark Jr., L. C., et al., "Differential Anodic Enzyme Polarography for the Measurement of Glucose", Oxygen Transport to Tissue: Instrumentation, Methods, and Physiology, 1973, pp. 127-133.
Clark Jr., L. C., et al., "Electrode Systems for Continuous Monitoring in Cardiovascular Surgery", Annals New York Academy of Sciences, 1962, pp. 29-45.

(56) References Cited

OTHER PUBLICATIONS

Clark Jr., L. C., et al., "Long-term Stability of Electroenzymatic Glucose Sensors Implanted in Mice", American Society of Artificial Internal Organs Transactions, vol. XXXIV, 1988, pp. 259-265.
Clarke, W. L., et al., "Evaluating Clinical Accuracy of Systems for Self-Monitoring of Blood Glucose", Diabetes Care, vol. 10, No. 5, 1987, pp. 622-628.
Complaint, "*Abbott Diabetes Care, Inc.* v. *Dexcom, Inc.*", filed Aug. 11, 2005.
Complaint, Amended, "*Abbott Diabetes Care, Inc.* v. *Dexcom, Inc.*", filed Jun. 27, 2006.
Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.
Csoregi, E., et al., "Design, Characterization, and One-Point in Vivo Calibration of a Subcutaneously Implanted Glucose Electrode", Analytical Chemistry, vol. 66 No. 19, 1994, pp. 3131-3138.
Csoregi, E., et al., "On-Line Glucose Monitoring by Using Microdialysis Sampling and Amperometric Detection Based on 'Wired' Glucose Oxidase in Carbon Paste", Mikrochimica Acta, vol. 121, 1995, pp. 31-40.
Dai, W. S., et al., "Hydrogel Membranes with Mesh Size Asymmetry Based on the Gradient Crosslinking of Poly(vinyl alcohol)," Journal of Membrane Science, vol. 156, 1999, pp. 67-79.
Davis, G., "Electrochemical Techniques for the Development of Amperometric Biosensors", Biosensors, vol. 1, 1985, pp. 161-178.
Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", The Journal of Physical Chemistry, vol. 91, No. 6, 1987, pp. 1285-1289.
Degani, Y., et al., Direct Electrical Communication Between Chemically Modified Enzymes.
And Metal Electrodes. 2. Methods for Bonding Electron-Transfer Relays to Glucose Oxidase and.
D-Amino-Acid Oxidase, Journal of the American Chemical Society, vol. 110, No. 8, 1988, pp. 2615-2620.
Degani, Y., et al., "Electrical Communication Between Redox Centers of Glucose Oxidase and Electrodes via Electrostatically and Covalently Bound Redox Polymers", Journal of the American Chemical Society, vol. 111, 1989, pp. 2357-2358.
Denisevich, P., et al., "Unidirectional Current Flow and Charge State Trapping at Redox Polymer Interfaces on Bilayer Electrodes: Principles, Experimental Demonstration, and Theory", Journal of the American Chemical Society, vol. 103, 1981, pp. 4727-4737.
Dicks, J. M., et al., "Ferrocene Modified Polypyrrole with Immobilised Glucose Oxidase and its Application in Amperometric Glucose Microbiosensors", Annales de Biologie Clinique, vol. 47, 1989, pp. 607-619.
Diem, P., et al., "Clinical Performance of a Continuous Viscometric Affinity Sensor for Glucose", Diabetes Technology & Therapeutics, vol. 6, 2004, pp. 790-799.
Ellis, C. D., et al., "Selectivity and Directed Charge Transfer through an Electroactive Metallopolymer Film", Journal of the American Chemical Society, vol. 103, No. 25, 1981, pp. 7480-7483.
Engstrom, R. C., "Electrochemical Pretreatment of Glassy Carbon Electrodes", Analytical Chemistry, vol. 54, No. 13, 1982, pp. 2310-2314.
Engstrom, R. C., et al., "Characterization of Electrochemically Pretreated Glassy Carbon Electrodes", Analytical Chemistry. vol. 56 No. 2, 1984, pp. 136-141.
Feldman, B., et al., "A Continuous Glucose Sensor Based on Wired Enzyme' Technology ¬Results from a 3-Day Trial in Patients with Type 1 Diabetes", Diabetes Technology & Therapeutics, vol. 5, No. 5, 2003, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
Feldman, B., et al., "Electron Transfer Kinetics at Redox Polymer/Solution Interfaces Using Microelectrodes and Twin Electrode Thin Layer Cells", Journal of ElectroAnalytical Chemistry, vol. 194, 1985, pp. 63-81.
Fischer, H., et al., "Intramolecular Electron Transfer Medicated by 4,41-Bypyridine and Related Bridging Groups", Journal of the American Chemical Society, vol. 98, No. 18, 1976, pp. 5512-5517.
Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," Analytical Biochemistry, vol. 204, 1992, pp. 305-310.
Foulds, N. C., et al., "Enzyme Entrapment in Electrically Conducting Polymers: Immobilisation of Glucose Oxidase in Polypyrrole and its Application in Amperometric Glucose Sensors", Journal of the Chemical Society, Faraday Transactions 1, vol. 82, 1986, pp. 1259-1264.
Foulds, N. C., et al., "Immobilization of Glucose Oxidase in Ferrocene-Modified Pyrrole Polymers", Analytical Chemistry, vol. 60, No. 22, 1988, pp. 2473-2478.
Frew, J. E., et al., "Electron-Transfer Biosensors", Philosophical Transactions of The Royal Society of London, vol. 316, 1987, pp. 95-106.
Garg, S., et al., "Improvement in Glycemic Excursions with a Transcutaneous, Real-Time Continuous Glucose Sensor", Diabetes Care, vol. 29, No. 1, 2006, pp. 44-50.
Godsland, I. F., et al., "Maximizing the Success Rate of Minimal Model Insulin Sensitivity Measurement in Humans: The Importance of Basal Glucose Levels," Clinical Science, vol. 101, 2001, pp. 1-9.
Gorton, L., et al., "Selective Detection in Flow Analysis Based on the Combination of Immobilized Enzymes and Chemically Modified Electrodes", Analytica Chimica Acta, vol. 250, 1991, pp. 203-248.
Graham, N. B., "Poly(ethylene oxide) and Related Hydrogels," Hydrogels in Medicine and Pharmacy, vol. II: Polymers, Chapter 4, 1987, pp. 95-113.
Gregg, B. A., et al., "Cross-Linked Redox Gels Containing Glucose Oxidase for Amperometric Bionsensor Applications", Analytical Chemistry, vol. 62, No. 3, 1990, pp. 258-263.
Gregg, B. A., et al., "Redox Polymer Films Containing Enzymes. 1. A Redox-Conducting Epoxy Cement: Synthesis, Characterization, and Electrocatalytic Oxidation of Hydroquinone", Journal of Physical Chemistry, vol. 95, No. 15, 1991, 5970-5975.
Hale, P. D., et al., "A New Class of Amperometric Biosensor Incorporating a Polymeric Electron-Transfer Mediator", Journal of the American Chemical Society, vol. 111, No. 9, 1989, pp. 3482-3484.
Hamilton, "Hamilton Needle Gauge Index", www.hamiltoncompany.com.
Harrison, D. J., et al., "Characterization of Perfluorosulfonic Acid Polymer Coated Enzyme Electrodes and a Miniatureized Integrated Potentiostat for Glucose Analysis in Whole Blood", Analytical Chemistry, vol. 60, No. 19, 1988, pp. 2002-2007.
Hawkridge, F. M., et al., "Indirect Coulometric Titration of Biological Electron Transport Components", Analytical Chemistry, vol. 45, No. 7, 1973, pp. 1021-1027.
Heller, A., "Electrical Connection Enzyme Redox Centers to Electrodes", Journal of Physical Chemistry, vol. 96, No. 9, 1990, pp. 3579-3587.
Heller, A., "Electrical Wiring of Redox Enzymes", Accounts of Chemical Research vol. 23, No. 5, 1990, 128-134.
Heller, A., et al., "Amperometric Biosensors Based on Three-Dimensional Hydrogel-Forming Epoxy Networks", Sensors and Actuators B, vol. 13-14, 1993, pp. 180-183.
Ianniello, R. M., et al., "Differential Pulse Voltammetric Study of Direct Electron Transfer in Glucose Oxidase Chemically Modified Graphite Electrodes", Analytical Chemistry, vol. 54, No. 7, 1982, pp. 1098-1101.
Ianniello, R. M., et al., "Immobilized Enzyme Chemically Modified Electrode as an Amperometric Sensor", Analytical Chemistry, vol. 53, No. 13, 1981, pp. 2090-2095.

(56) References Cited

OTHER PUBLICATIONS

Ikeda, T., et al., "Glucose Oxidase-Immobilized Benzoquinone-Carbon Paste Electrode as a Glucose Sensor", Agricultural and Biological Chemistry, vol. 49, No. 2, 1985, pp. 541-543.
Ikeda, T., et al., "Kinetics of Outer-Sphere Electron Transfers Between Metal Complexes in Solutions and Polymeric Films on Modified Electrodes", Journal of the American Chemical Society, vol. 103, No. 25, 1981, pp. 7422-7425.
Isermann, R., "Supervision, Fault-Detection and Fault-Diagnosis Methods—An Introduction", Control Engineering Practice, vol. 5, No. 5, 1997, pp. 639-652.
Isermann, R., et al., "Trends in the Application of Model-Based Fault Detection and Diagnosis of Technical Processes", Control Engineering Practice, vol. 5, No. 5, 1997, pp. 709-719.
Johnson, J. M., et al., "Potential-Dependent Enzymatic Activity in an Enzyme Thin-Layer Cell", Analytical Chemistry, vol. 54, No. 8, 1982, pp. 1377-1383.
Johnson, K. W., "Reproducible Electrodeposition of Biomolecules for the Fabrication of Miniature Electroenzymatic Biosensors", Sensors and Actuators B, vol. 5, 1991, pp. 85-89.
Johnson, K. W., et al., "In vivo Evaluation of an Electroenzymatic Glucose Sensor Implanted in Subcutaneous Tissue", Biosensors & Bioelectronics, vol. 7, 1992, pp. 709-714.
Johnson, P. C., "Peripheral Circulation", John Wiley & Sons, 1978, p. 198.
Jonsson, G., et al., "An Amperometric Glucose Sensor Made by Modification of a Graphite Electrode Surface With Immobilized Glucose Oxidase and Adsorbed Mediator", Biosensors, vol. 1, 1985, pp. 355-368.
Josowicz, M., et al., "Electrochemical Pretreatment of Thin Film Platinum Electrodes", Journal of the Electrochemical Society, vol. 135 No. 1, 1988, pp. 112-115.
Jungheim, K., et al., "How Rapid Does Glucose Concentration Change in Daily Life of Patients with Type 1 Diabetes?", 2002, p. 250.
Jungheim, K., et al., "Risky Delay of Hypoglycemia Detection by Glucose Monitoring at the Arm", Diabetes Care, vol. 24, No. 7, 2001, pp. 1303-1304.
Kaplan, S. M., "Wiley Electrical and Electronics Engineering Dictionary", IEEE Press, 2004, pp. 141, 142, 548, 549.
Katakis, I., et al., "Electrostatic Control of the Electron Transfer Enabling Binding of Recombinant Glucose Oxidase and Redox Polyelectrolytes", Journal of the American Chemical Society, vol. 116, No. 8, 1994, pp. 3617-3618.
Katakis, I., et al., "L-a-Glycerophosphate and L-Lactate Electrodes Based on the Electrochemical 'Wiring' of Oxidases", Analytical Chemistry, vol. 64, No. 9, 1992, pp. 1008-1013.
Kemp, G. J., "Theoretical Aspects of One-Point Calibration: Causes and Effects of Some Potential Errors, and Their Dependence on Concentration," Clinical Chemistry, vol. 30, No. 7, 1984, pp. 1163-1167.
Kenausis, G., et al.,—Wiring' of Glucose Oxidase and Lactate Oxidase Within a Hydrogel Made with Poly(vinyl pyridine) complexed with [Os(4,41-dimethoxy-2,2'- bipyridine)2C1]+i2+, Journal of the Chemical Society, Faraday Transactions, vol. 92, No. 20, 1996, pp. 4131-4136.
Kerner, W., et al., "The Function of a Hydrogen Peroxide-Detecting Electroenzymatic Glucose Electrode is Markedly Impaired in Human Subcutaneous Tissue and Plasma," Biosensors & Bioelectronics, vol. 8, 1993, pp. 473-482.
Kondepati, V., et al., "Recent Progress in Analytical Instrumentation for Glycemic Control in Diabetic and Critically Ill Patients", Analytical Bioanalytical Chemistry, vol. 388, 2007, pp. 545-563.
Korf, J., et al., "Monitoring of Glucose and Lactate Using Microdialysis: Applications in Neonates and Rat Brain," Developmental Neuroscience, vol. 15, 1993, pp. 240-246.
Koudelka, M., et al., "In-Vivo Behaviour of Hypodermically Implanted Microfabricated Glucose Sensors", Biosensors & Bioelectronics, vol. 6, 1991, pp. 31-36.
Kulys, J., et al., "Mediatorless Peroxidase Electrode and Preparation of Bienzyme Sensors", Bioelectrochemistry and Bioenergetics, vol. 24, 1990, pp. 305-311.
Lager, W., et al., "Implantable Electrocatalytic Glucose Sensor", Hormone Metabolic Research, vol. 26, 1994, pp. 526-530.
Laurell, T., "A Continuous Glucose Monitoring System Based on Microdialysis", Journal of Medical Engineering & Technology, vol. 16, No. 5, 1992, pp. 187-193.
Lindner, E., et al., "Flexible (Kapton-Based) Microsensor Arrays of High Stability for Cardiovascular Applications", Journal of the Chemical Society, Faraday Transactions, vol. 89, No. 2, 1993, pp. 361-367.
Lodwig, V., et al., "Continuous Glucose Monitoring with Glucose Sensors: Calibration and Assessment Criteria", Diabetes Technology & Therapeutics, vol. 5, No. 4, 2003, pp. 573-587.
Lortz, J., et al., "What is Bluetooth? We Explain The Newest Short-Range Connectivity Technology", Smart Computing Learning Series, Wireless Computing, vol. 8, Issue 5, 2002, pp. 72-74.
Maidan, R., et al., "Elimination of Electrooxidizable Interferant-Produced Currents in Amperometric Biosensors", Analytical Chemistry, vol. 64, No. 23, 1992, pp. 2889-2896.
Malin, S. F., et al., "Noninvasive Prediction of Glucose by Near-Infrared Diffuse Reflectance Spectoscopy", Clinical Chemistry, vol. 45, No. 9, 1999, pp. 1651-1658.
Marko-Varga, G., et al., "Enzyme-Based Biosensor as a Selective Detection Unit in Column Liquid Chromatography", Journal of Chromatography A, vol. 660, 1994, pp. 153-167.
Mastrototaro, J. J., et al., "An Electroenzymatic Glucose Sensor Fabricated on a Flexible Substrate", Sensors and Actuators B, vol. 5, 1991, pp. 139-144.
Mauras, N., et al., "Lack of Accuracy of Continuous Glucose Sensors in Healthy, Nondiabetic Children: Results of the Diabetes Research in Children Network (DirecNet) Accuracy Study," Journal of Pediatrics, 2004, pp. 770-775.
Mcgarraugh, G., et al., "Glucose Measurements Using Blood Extracted from the Forearm and the Finger", TheraSense, Inc., 2001, 16 Pages.
Mcgarraugh, G., et al., "Physiological Influences on Off-Finger Glucose Testing", Diabetes Technology & Therapeutics, vol. 3, No. 3, 2001, pp. 367-376.
Mckean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.
Mcneil, C. J., et al., "Thermostable Reduced Nicotinamide Adenine Dinucleotide Oxidase: Application to Amperometric Enzyme Assay", Analytical Chemistry, vol. 61, No. 1, 1989, pp. 25-29.
Miyawaki, 0., et al., "Electrochemical and Glucose Oxidase Coenzyme Activity of Flavin Adenine Dinucleotide Covalently Attached to Glassy Carbon at the Adenine Amino Group", Biochimica et Biophysica Acta, vol. 838, 1985, pp. 60-68.
Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, vol. 7, 1992, pp. 345-352.
Moatti-Sirat, D., et al., "Reduction of Acetaminophen Interference in Glucose Sensors by a Composite Nafion Membrane: Demonstration in Rats and Man", Diabetologia, vol. 37, 1994, pp. 610-616.
Moatti-Sirat, D., et al., "Towards Continuous Glucose Monitoring: In Vivo Evaluation of a Miniaturized Glucose Sensor Implanted for Several Days in Rat Subcutaneous Tissue", Diabetologia, vol. 35, 1992, pp. 224-330.
Mougiakakou, et al., "A Real Time Simulation Model of Glucose-Insulin Metabolism for Type 1 Diabetes Patients", Proceedings of the 2005 IEEE, 2005, pp. 298-301.
Nagy, G., et al., "A New Type of Enzyme Electrode: The Ascorbic Acid Eliminator Electrode", Life Sciences, vol. 31, No. 23, 1982, pp. 2611-2616.
Nakamura, S., et al., "Effect of Periodate Oxidation on the Structure and Properties of Glucose Oxidase", Biochimica et Biophysica Acta., vol. 445, 1976, pp. 294-308.

(56) References Cited

OTHER PUBLICATIONS

Narasimham, K., et al., "p-Benzoquinone Activation of Metal Oxide Electrodes for Attachment of Enzymes", Enzyme and Microbial Technology, vol. 7, 1985, pp. 283-286.
Ohara, T. J., "Osmium Bipyridyl Redox Polymers Used in Enzyme Electrodes", Platinum Metals Review, vol. 39, No. 2, 1995, pp. 54-62.
Ohara, T. J., et al.,—Wired' Enzyme Electrodes for Amperometric Determination of Glucose or Lactate in the Presence of Interfering Substances, Analytical Chemistry, vol. 66, No. 15, 1994, pp. 2451-2457.
Ohara, T. J., et al., "Glucose Electrodes Based on Cross-Linked [Os(bpy)2C1]+i2+ Complexed Poly(1-Vinylimidazole) Films", Analytical Chemistry, vol. 65, No. 23, 1993, pp. 3512-3517.
Olievier, C. N., et al., "In Vivo Measurement of Carbon Dioxide Tension with a Miniature Electrodes", Pflugers Archiv: European Journal of Physiology, vol. 373, 1978, pp. 269-272.
Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", Journal of ElectroAnalytical Chemistry, vol. 260, 1989, pp. 487-494.
Palleschi, G., et al., "A Study of Interferences in Glucose Measurements in Blood by Hydrogen Peroxide Based Glucose Probes", Analytical Biochemistry, vol. 159, 1986, pp. 114-121.
Pankratov, I., et al., "Sol-Gel Derived Renewable-Surface Biosensors", Journal of ElectroAnalytical Chemistry, vol. 393, 1995, pp. 35-41.
Parker, R., et al., "Robust Hoe Glucose Control in Diabetes Using a Physiological Model", AIChE Journal, vol. 46, No. 12, 2000, pp. 2537-2549.
Pathak, C., et al., "Rapid Photopolymerization of Immunoprotective Gels in Contact with Cells and Tissue", Journal of the American Chemical Society, vol. 114, No. 21, 1992, pp. 8311-8312.
Pickup, J., "Developing Glucose Sensors for In Vivo Use", Tibtech, vol. 11, 1993, pp. 285-291.
Pickup, J., et al., "Implantable Glucose Sensors: Choosing the Appropriate Sensing Strategy", Biosensors, vol. 3, 1987/88, pp. 335-346.
Pickup, J., et al., "In Vivo Molecular Sensing in Diabetes Mellitus: An Implantable Glucose Sensor with Direct Electron Transfer", Diabetologia, vol. 32, 1989, pp. 213-217.
Pickup, J., et al., "Potentially-Implantable, Amperometric Glucose Sensors with Mediated Electron Transfer: Improving the Operating Stability", Biosensors, vol. 4, 1989, pp. 109-119.
Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.
Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", Diabetolgia, vol. 36, 1993, pp. 658-663.
Poitout, V., et al., "Calibration in Dogs of a Subcutaneous Miniaturized Glucose Sensor Using a Glucose Meter for Blood Glucose Determination", Biosensors & Bioelectronics, vol. 7, 1992, pp. 587-592.
Poitout, V., et al., "In Vitro and In Vivo Evaluation in Dogs of a Miniaturized Glucose Sensor", ASAIO Transactions, vol. 37, No. 3, 1991, pp. M298-M300.
Pollak, A., et al., "Enzyme Immobilization by Condensation Copolymerization into Cross-Linked Polyacrylamide Gels", Journal of the American Chemical Society, vol. 102, No. 20, 1980, pp. 6324-6336.
Quinn, C. P., et al., "Kinetics of Glucose Delivery to Subcutaneous Tissue in Rats Measured with 0.3-mm Amperometric Microsensors", The American Physiological Society, 1995, E155-E161.
Reach, G., et al., "Can Continuous Glucose Monitoring Be Used for the Treatment of Diabetes?", Analytical Chemistry, vol. 64, No. 6, 1992, pp. 381-386.
Rebrin, K., et al., "Automated Feedback Control of Subcutaneous Glucose Concentration in Diabetic Dogs", Diabetologia, vol. 32, 1989, pp. 573-576.
Reusch, W., "Other Topics: Organometallic Chemistry: Organometallic Compounds: Main Group Organometallic Compounds," Virtual Textbook of Organic Chemistry, 1999, Rev. 2007, 25 pages.
Roe, J. N., et al., "Bloodless Glucose Measurements", Critical Review in Therapeutic Drug Carrier Systems, vol. 15, Issue 3, 1998, pp. 199-241.
Sacks (Ed), "Guidelines and Recommendations for Laboratory Analysis in the Diagnosis and Management of Diabetes Mellitus," The National Academy of Clinical Biochemistry Presents Laboratory Medicine Practice Guidelines, vol. 13, 2002, pp. 8-11, 21-23, 52-56, 63.
Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.
Sakakida, M., et al., "Ferrocene-Mediated Needle-Type Glucose Sensor Covered with Newly Designed Biocompatible Membrane", Sensors and Actuators B, vol. 13-14, 1993, pp. 319-322.
Salditt, P., "Trends in Medical Device Design and Manufacturing", SMTA News and Journal of Surface Mount Technology, vol. 17, 2004, pp. 19-24.
Salehi, C., et al., "A Telemetry-Instrumentation System for Long-Term Implantable Glucose and Oxygen Sensors", Analytical Letters, vol. 29, No. 13, 1996, pp. 2289-2308.
Samuels, G. J., et al., "An Electrode-Supported Oxidation Catalyst Based on Ruthenium (IV). pH 'Encapsulation' in a Polymer Film", Journal of the American Chemical Society, vol. 103, No. 2, 1981, pp. 307-312.
Sasso, S. V., et al., "Electropolymerized 1,2-Diaminobenzene as a Means to Prevent Interferences and Fouling and to Stabilize Immobilized Enzyme in Electrochemical Biosensors", Analytical Chemistry, vol. 62, No. 11, 1990, pp. 1111-1117.
Scheller, F. W., et al., "Second Generation Biosensors," Biosensors & Bioelectronics, vol. 6, 1991, pp. 245-253.
Scheller, F., et al., "Enzyme Electrodes and Their Application", Philosophical Transactions of The Royal Society of London B, vol. 316, 1987, pp. 85-94.
Schmehl, R. H., et al., "The Effect of Redox Site Concentration on the Rate of Mediated Oxidation of Solution Substrates by a Redox Copolymer Film", Journal of ElectroAnalytical Chemistry, vol. 152, 1983, pp. 97-109.
Schmidt, F. J., et al., "Calibration of a Wearable Glucose Sensor", The International Journal of Artificial Organs, vol. 15, No. 1, 1992, pp. 55-61.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.
Shichiri, M., et al., "Glycaemic Control in Pancreatectomized Dogs with a Wearable Artificial Endocrine Pancreas", Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.
Shichiri, M., et al., "Membrane Design for Extending the Long-Life of an Implantable Glucose Sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.
Shichiri, M., et al., "Wearable Artificial Endocrine Pancreas With Needle-Type Glucose Sensor", The Lancet, 1982, pp. 1129-1131.

(56) References Cited

OTHER PUBLICATIONS

Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.
Sittampalam, G., et al., "Surface-Modified Electrochemical Detector for Liquid Chromatography", Analytical Chemistry, vol. 55, No. 9, 1983, pp. 1608-1610.
Skoog, D. A., et al., "Evaluation of Analytical Data," Fundamentals of Analytical Chemistry, 1966, p. 55.
Soegijoko, S., et al., "External Artificial Pancreas: A New Control Unit Using Microprocessor", Hormone and Metabolic Research Supplement Series, vol. 12, 1982, pp. 165-169.
Sprules, S. D., et al., "Evaluation of a New Disposable Screen-Printed Sensor Strip for the Measurement of NADH and Its Modification to Produce a Lactate Biosensor Employing Microliter Volumes", Electroanalysis, vol. 8, No. 6, 1996, pp. 539-543.
Sternberg, F., et al., "Calibration Problems of Subcutaneous Glucosensors when Applied 'In-Situ' in Man", Hormone and Metabolic Research, vol. 26, 1994, pp. 523-526.
Sternberg, R., et al., "Covalent Enzyme Coupling on Cellulose Acetate Membranes for Glucose Sensor Development", Analytical Chemistry, vol. 60, No. 24, 1988, pp. 2781-2786.
Sternberg, R., et al., "Study and Development of Multilayer Needle-Type Enzyme-Based Glucose Microsensors", Biosensors, vol. 4, 1988, pp. 27-40.
Suekane, M., "Immobilization of Glucose Isomerase", Zettschrift fur Allgemeine Mikrobiologie, vol. 22, No. 8, 1982, pp. 565-576.
Tajima, S., et al., "Simultaneous Determination of Glucose and 1,5-Anydroglucitol", Chemical Abstracts, vol. 111, No. 25, 1989, p. 394.
Takamura, A., et al., "Drug release from Poly(vinyl alcohol) Gel Prepared by Freeze-Thaw Procedure", Journal of Controlled Release, vol. 20, 1992, pp. 21-27.
Tarasevich, M. R., "Bioelectrocatalysis", Comprehensive Treatise of Electrochemistry, vol. 10, 1985, pp. 231-295.
Tatsuma, T., et al., "Enzyme Monolayer—and Bilayer-Modified Tin Oxide Electrodes for the Determination of Hydrogen Peroxide and Glucose", Analytical Chemistry, vol. 61, No. 21, 1989, pp. 2352-2355.
Taylor, C., et al.,—Wiring' of Glucose Oxidase Within a Hydrogel Made with Polyvinyl Imidazole Complexed with [(Os-4,4'-dimethoxy-2,2'-bipyridine)C1r2+, Journal of ElectroAnalytical Chemistry, vol. 396, 1995, pp. 511-515.
Thompson, M., et al., "In Vivo Probes: Problems and Perspectives", Clinical Biochemistry, vol. 19, 1986, pp. 255-261.
Travenol Laboratories, Inc., An Introduction to "Eugly", Book 1, 1985, p. 1-22.
Trojanowicz, M., et al., "Enzyme Entrapped Polypyrrole Modified Electrode for Flow-Injection Determination of Glucose", Biosensors & Bioelectronics, vol. 5, 1990, pp. 149-156.
Tsalikian, E., et al., "Accuracy of the GlucoWatch G2® Biographer and the Continuous Glucose Monitoring System During Hypoglycemia: Experience of the Diabetes Research in Children Network", Diabetes Care, vol. 27, No. 3, 2004, pp. 722-726.
Turner, A., et al., "Diabetes Mellitus: Biosensors for Research and Management", Biosensors, vol. 1, 1985, pp. 85-115.
Turner, R. F., et al., "A Biocompatible Enzyme Electrode for Continuous in vivo Glucose Monitoring in Whole Blood", Sensors and Actuators B, vol. 1, 1990, pp. 561-564.
Tuzhi, P., et al., "Constant Potential Pretreatment of Carbon Fiber Electrodes for In Vivo Electrochemistry", Analytical Letters, vol. 24, No. 6, 1991, pp. 935-945.
U.S. Patent Reexamination Application No. 90/007,903, Request for Reexamination of U.S. Pat. No. 6,565,509 filed Jan. 25, 2006.
U.S. Patent Reexamination Application No. 90/007,910, Request for Reexamination of U.S. Pat. No. 6,175,752 filed Feb. 1, 2006.
U.S. Patent Reexamination Application No. 90/007,913, Request for Reexamination of U.S. Pat. No. 6,284,478 filed Feb. 1, 2006.
U.S. Patent Reexamination Application No. 90/007,914, Request for Reexamination of U.S. Pat. No. 6,329,161 filed Feb. 1, 2006.
U.S. Patent Reexamination Application No. 90/008,172, Request for Reexamination of U.S. Pat. No. 6,990,366 filed Aug. 16, 2006.
U.S. Patent Reexamination Application No. 90/008,173, Request for Reexamination of U.S. Pat. No. 6,134,461 filed Aug. 16, 2006.
U.S. Patent Reexamination Application No. 90/008,457, Request for Reexamination of U.S. Pat. No. 6,990,366 filed Jan. 23, 2007.
U.S. Patent Reexamination Application No. 90/008,665, Request for Reexamination of U.S. Pat. No. 6,284,478 filed May 25, 2007.
U.S. Patent Reexamination Application No. 90/008,713, Request for Reexamination of U.S. Pat. No. 6,329,161 filed Jul. 25, 2007.
Umana, M., "Protein-Modified Electrochemically Active Biomaterial Surface", U.S. Army Research Office Analytical and Chemical Sciences Research Triangle Institute, 1988, pp. 1-9.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.
Urban, G., et al., "Miniaturized Thin-Film Biosensors Using Covalently Immobilized Glucose Oxidase", Biosensors & Bioelectronics, vol. 6, 1991, pp. 555-562.
Velho, G., et al., "In Vitro and In Vivo Stability of Electrode Potentials in Needle-Type Glucose Sensors", Diabetes, vol. 38, No. 2, 1989, pp. 164-171.
Velho, G., et al., "Strategies for Calibrating a Subcutaneous Glucose Sensor", Biomedica Biochimica Acta, vol. 48, 1989, pp. 957-964.
Von Woedtke, T., et al., "In Situ Calibration of Implanted Electrochemical Glucose Sensors", Biomedica Biochimica Acta, vol. 48, 1989, pp. 943-952.
Vreeke, M. S., et al., "Hydrogen Peroxide Electrodes Based on Electrical Connection of Redox Centers of Various Peroxidases to Electrodes through a Three-Dimensional Electron-Relaying Polymer Network", Diagnostic Biosensors Polymers, Chapter 15, 1993, pp. 180-193.
Vreeke, M., et al., "Hydrogen Peroxide and 0-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", Analytical Chemistry, vol. 64, No. 24, 1992, pp. 3084-3090.
Wang, D. L., et al., "Miniaturized Flexible Amperometric Lactate Probe", Analytical Chemistry, vol. 65, No. 8, 1993, pp. 1069-1073.
Wang, J., et al., "Activation of Glassy Carbon Electrodes by Alternating Current Electrochemical Treatment", Analytica Chimica Acta, vol. 167, 1985, pp. 325-334.
Wang, J., et al., "Amperometric Biosensing of Organic Peroxides with Peroxidase-Modified Electrodes", Analytica Chimica Acta, vol. 254, 1991, pp. 81-88.
Wang, J., et al., "Screen-Printable Sol-Gel Enzyme-Containing Carbon Inks", Analytical Chemistry, vol. 68, No. 15, 1996, pp. 2705-2708.
Wang, J., et al., "Sol-Gel-Derived Metal-Dispersed Carbon Composite Amperometric Biosensors", Electroanalysis, vol. 9, No. 1, 1997, pp. 52-55.
Williams, D. L., et al., "Electrochemical-Enzymatic Analysis of Blood Glucose and Lactate", Analytical Chemistry, vol. 42, No. 1, 1970, pp. 118-121.
Wilson, G. S., et al., "Progress Toward the Development of an Implantable Sensor for Glucose", Clinical Chemistry, vol. 38, No. 9, 1992, pp. 1613-1617.
Yabuki, S., et al., "Electro-Conductive Enzyme Membrane", Journal of the Chemical Society, Chemical Communications, 1989, pp. 945-946.
Yang, C., et al., "A Comparison of Physical Properties and Fuel Cell Performance of Nation and Zirconium Phosphate/Nafion Composite Membranes," Journal of Membrane Science, vol. 237, 2004, pp. 145-161.
Yang, L., et al., "Determination of Oxidase Enzyme Substrates Using Cross-Flow Thin-Layer Amperometry", Electroanalysis, vol. 8, No. 8-9, 1996, pp. 716-721.
Yao, S. J., et al., "The Interference of Ascorbate and Urea in Low-Potential Electrochemical Glucose Sensing", Proceedings of

(56) References Cited

OTHER PUBLICATIONS the Twelfth Annual International Conference of the IEEE Engineering in Medicine and Biology Society, vol. 12, Part 2, 1990, pp. 487-489.
Yao, T., "A Chemically-Modified Enzyme Membrane Electrode as an Amperometric Glucose Sensor", Analytica Chimica Acta, vol. 148, 1983, pp. 27-33.
Ye, L., et al., "High Current Density 'Wired' Quinoprotein Glucose Dehydrogenase Electrode", Analytical Chemistry, vol. 65, No. 3, 1993, pp. 238-241.
Yildiz, A., et al., "Evaluation of an Improved Thin-Layer Electrode", Analytical Chemistry, vol. 40, No. 7, 1968, pp. 1018-1024.
Zamzow, K., et al., "New Wearable Continuous Blood Glucose Monitor (BGM) and Artificial Pancreas (AP)", Diabetes, vol. 39, 1990, pp. 5A-20.
Zhang, Y., et al., "Application of Cell Culture Toxicity Tests to the Development of Implantable Biosensors", Biosensors & Bioelectronics, vol. 6, 1991, pp. 653-661.
Zhang, Y., et al., "Elimination of the Acetaminophen Interference in an Implantable Glucose Sensor", Analytical Chemistry, vol. 66, No. 7, 1994, pp. 1183-1188.
European Patent Application No. 06839637.3, Extended European Search Report mailed Sep. 3, 2010.
European Patent Application No. 06839637.3, Intention to Grant a European Patent mailed Aug. 14, 2012.
PCT Application No. PCT/US2006/060394, International Preliminary Report on Patentability and Written Opinion of the International Searching Authority mailed May 15, 2008.
PCT Application No. PCT/US2006/060394, International Search Report and Written Opinion of the International Searching Authority mailed Oct. 31, 2006.
U.S. Appl. No. 12/959,323, Office Action mailed Oct. 5, 2012.
Abstract for Japanese Patent Publication JP-55-010581 published Jan. 25, 1980.
Abstract for Japanese Patent Publication JP-55-010583 published Jan. 25, 1980.
Abstract for Japanese Patent Publication JP-55-010584 published Jan. 25, 1980.
International Preliminary Report on Patentability and Written Opinion of the International Searching Authority for PCT Application No. PCT/US2006/060394 filed Oct. 31, 2006 to Abbott Diabetes Care, Inc., et al. mailed May 15, 2008.
Choudhary, et al., Insulin Pump Therapy With Automated Insulin Suspension in Response to Hypoglycemia, Reduction in nocturnal hypoglycemia in those at greatest risk, Diabetes Care, vol. 34, pp. 2023-2025 (2011).
Congress.gov, About the Congressional Record, Feb. 22, 2022, 3 pages.
Declaration of Thomas Edward Foster of Taylor Wessing LLP, Hill House, 1 Little New St. London EC4A 3TR ("Taylor Wessing"), signed on Jan. 30, 2024, 160 pages.
FDA Premarket Approval (PMA) for Seven Plus Continuous Glucose Monitoring System, Notice Date: Jun. 28, 2007, 3 pages.
Federal Register, vol. 76, No. 120, Jun. 22, 2011, pp. 36542-36543.
Hon, Urging FDA to Act Promptly to Approve Artificial Pancreas Technologies, Congressional Record (Bound Edition), vol. 157 (2011), Part 13, 3 pages.
Kowalski, Can We Really Close the Loop and How Soon? Accelerating the Availability of an Artificial Pancreas: A Roadmap to Better Diabetes Outcomes, Diabetes Technology & Therapeutics, vol. 11, pp. S-113-S-119 (2009).
Letter from Department of Health & Human Services to Mr. Andy Balo, Dexcom, Inc. re. P050012/S001, STS-7 Continuous Glucose Monitoring System, dated May 31, 2007, 7 pages.
Pickup, et al., Semi-Closed-Loop Insulin Delivery Systems: Early Experience with Low-Glucose Insulin Suspend Pumps, Diabetes Technology & Therapeutics, vol. 13, No. 7, pp. 695-698 (2011).
PMA Final Decisions Rendered for May 2007, FDA U.S. Food and Drug Administration, 21 pages.
STS-7 Continuous Glucose Monitoring System—P050012/S001, Approved May 31, 2007, FDA U.S. Food and Drug Administration, 1 page.
"DexCom's 7-Day STS Continuous Glucose Monitoring System", Jun. 1, 2007 https://newatlas.com/dexcoms-7-day-sts-continuous-glucose-monitoring-system/7376/ 1 page.
Exhibit CP-3, Expert Report of Dr. Cesar C. Palerm, Sep. 20, 2022: In Vivo Glucose Sensing, Chemical Analysis, A Series of Monographs on Analytical Chemistry and Its Applications, vol. 174, Wiley (2010).
Exhibit CP-4, Expert Report of Dr. Cesar C. Palerm, Sep. 20, 2022: Animas® Vibe™, the First Integrated Offering from Animas Corporation and Dexcom, Inc., Receives European CE Mark Approval (2011).
Exhibit CP-6, Second Expert Report of Dr. Cesar C. Palerm, Oct. 21, 2022: Bailey, et al., Reduction in Hemoglobin A1c with Real-Time Continuous Glucose Monitoring: Results from a 12-Week Observational Study, Diabetes Technology & Therapeutics, vol. 9, No. 3, pp. 203-210 (2007).
Exhibit CP-8, Second Expert Report of Dr. Cesar C. Palerm, Oct. 21, 2022: Garg, et al., Relationship of Fasting and Hourly Blood Glucose Levels to $HbA_{1c}$ Values, Diabetes Care, vol. 29, No. 12, pp. 2644-2649 (2006).
Exhibit CP-9, Second Expert Report of Dr. Cesar C. Palerm, Oct. 21, 2022: Welcome to Your FreeStyle Libre System, In-Service Guide, Abbott (2017).
Exhibit CP-10, Second Expert Report of Dr. Cesar C. Palerm, Oct. 21, 2022: Standards of Medical Care in Diabetes-2009, American Diabetes Association, Diabetes Care, vol. 32, Supplement 1, pp. S13-S61 (2009).
Exhibit No. 23, to the Expert Report of Professor Nick Oliver, Sep. 20, 2022: CGMS® System Gold™ Continuous Glucose Monitoring Overview, Medtronic MiniMed (2004).
Exhibit No. 20, to the Expert Report of Professor Nick Oliver, Sep. 20, 2022: Continuous Glucose Sensors: Continuing Questions about Clinical Accuracy, J Diabetes Sci Technol vol. 1, Issue 5, pp. 669-675 (2007).
Exhibit No. 19, to the Expert Report of Professor Nick Oliver, Sep. 20, 2022: Glucose Concentrations of Less Than 3.0 mmol/L (54 mg/dL) Should Be Reported in Clinical Trials: A Joint Position Statement of the American Diabetes Association and the European Association for the Study of Diabetes, Diabetes Care, vol. 40, pp. 155-157 (2017).
Exhibit No. 18, to the Expert Report of Professor Nick Oliver, Sep. 20, 2022: Aleppo, et al., Replace-BG: A Randomized Trial Comparing Continuous Glucose Monitoring With and Without Routine Blood Glucose Monitoring in Adults With Well-Controlled Type 1 Diabetes, Diabetes Care, vol. 40, pp. 538-545 (2017).
Exhibit No. 17, to the Expert Report of Professor Nick Oliver, Sep. 20, 2022: Diabetes (type 1), NIHR (2011).
Exhibit No. 16, to the Expert Report of Professor Nick Oliver, Sep. 20, 2022: Pickup, et al., Glycaemic control in type 1 diabetes during real time continuous glucose monitoring compared with self monitoring of blood glucose: meta-analysis of randomised controlled trials using individual patient data, BMJ (2011).
Exhibit No. 15, to the Expert Report of Professor Nick Oliver, Sep. 20, 2022: Oxford Textbook of Endocrinology and Diabetes (2011).
Exhibit No. 14, to the Expert Report of Professor Nick Oliver, Sep. 20, 2022: Type 1 diabetes: diagnosis and management of type 1 diabetes in children, young people and adults, Clinical Guideline 15, NHS, National Institute for Clinical Excellence (2004).
Exhibit No. 13, to the Expert Report of Professor Nick Oliver, Sep. 20, 2022: Training in flexible, intensive, insulin management to enable dietary freedom in people with type 1 diabetes: dose adjustment for normal eating (DAFNE) randomised controlled trial, BMJ, vol. 325 (2002).
Exhibit No. 12, to the Expert Report of Professor Nick Oliver, Sep. 20, 2022: Modern Standards and Service Models, Diabetes, National Service Framework for Diabetes: Standards, Department of Health (2000).
Exhibit No. 11, to the Expert Report of Professor Nick Oliver, Sep. 20, 2022: The Effect of Intensive Treatment of Diabetes on the Development and Progression of Long-Term Complications in

(56) References Cited

OTHER PUBLICATIONS

Insulin-Dependent Diabetes Mellitus, The New England Journal of Medicine, vol. 329, No. 14 (1993).
Exhibit No. 10, to the Expert Report of Professor Nick Oliver, Sep. 20, 2022: Type 1 Diabetes Research Roadmap, Identifying the strengths and weaknesses, gaps and opportunities of UK type 1 diabetes research; clearing a path to the cure, JDRF Improving Lives. Curing Type 1 Diabetes. Join US in finding the cure for type 1 diabetes (2013).
Exhibit No. 9, to the Expert Report of Professor Nick Oliver, Sep. 20, 2022: Guideline on clinical investigation of medicinal products in the treatment or prevention of diabetes mellitus, European Medicines Agency, Science Medicines Health (2012).
Exhibit No. 8, to the Expert Report of Professor Nick Oliver, Sep. 20, 2022: Oxford Textbook of Endocrinology and Diabetes (2011).
Exhibit No. 7, to the Expert Report of Professor Nick Oliver, Sep. 20, 2022: Cryer, Preventing hypoglycaemia: what is the appropriate glucose alert value?, Diabetologia, vol. 52, pp. 35-37 (2009).
Exhibit No. 6, to the Expert Report of Professor Nick Oliver, Sep. 20, 2022: Frier, Defining hypoglycaemia: what level has clinical relevance?, Diabetologia, vol. 52, pp. 31-34 (2009).
Exhibit No. 5, to the Expert Report of Professor Nick Oliver, Sep. 20, 2022: Swinnen, et al., Changing the glucose cut-off values that define hypoglycaemia has a major effect on reported frequencies of hypoglycaemia, Diabetologia, vol. 52, pp. 38-41 (2009).
Exhibit No. 4, to the Expert Report of Professor Nick Oliver, Sep. 20, 2022: Amiel, et al., Review Article, Hypoglycaemia in Type 2 diabetes, Diabetic Medicine, vol. 25, pp. 245-254 (2008).
Exhibit No. 3, to the Expert Report of Professor Nick Oliver, Sep. 20, 2022: Defining and Reporting Hypoglycemia in Diabetes, Diabetes Care, vol. 28, No. 5, pp. 1245-1249 (2005).
Exhibit No. 2, to the Expert Report of Professor Nick Oliver, Sep. 20, 2022: Committee for Proprietary Medicinal Products (CPMP), Note for Guidance on Clinical Investigation of Medicinal Products in the Treatment of Diabetes Mellitus, EMEA, The European Agency for the Evaluation of Medicinal Products (2002).
Exhibit No. 28, to the Expert Report of Professor Nick Oliver, Sep. 20, 2022: FreeStyle Navigator II, Continuous Glucose Monitoring System, User's Manual, Abbott (2011-2013).
Exhibit No. 27, to the Expert Report of Professor Nick Oliver, Sep. 20, 2022: FreeStyle Navigator, Continuous Glucose Monitoring System, User Guide, Abbott (2008, 2010).
Exhibit No. 26, to the Expert Report of Professor Nick Oliver, Sep. 20, 2022: CGMS® iPro™ Continuous Glucose Recorder, User Guide, Medtronic MiniMed (2007).
Exhibit No. 25, to the Expert Report of Professor Nick Oliver, Sep. 20, 2022: Guardian® REAL-Time, Continuous Glucose Monitoring System, User Guide, Medtronic MiniMed (2006).
Exhibit No. 24, to the Expert Report of Professor Nick Oliver, Sep. 20, 2022: GlucoWatch G2, Automatic Glucose Biographer and Auto Sensors (2002).
Exhibit No. 20, to the Expert Report of Professor Nick Oliver, Sep. 20, 2022: Continuous Glucose Sensors: Continuing Questions about Clinical Accuracy, Journal of Diabetes Science and Technology, vol. 1, Issue 5, pp. 669-675 (2007).
Exhibit No. 29, to the Expert Report of Professor Nick Oliver, Sep. 20, 2022: Dexcom G4, Continuous Glucose Monitoring System, User's Guide (2013).
Exhibit No. 31, to the Expert Report of Professor Nick Oliver, Sep. 20, 2022: Revised Specification for EP625.
Exhibit No. 32, to the Expert Report of Professor Nick Oliver, Sep. 20, 2022: Puhr, et al., Real-World Hypoglycemia Avoidance with a Predictive Low Glucose Alert Does Not Depend on Frequent Screen Views, Journal of Diabetes Science and Technology, vol. 14(1), pp. 83-86 (2020).
Exhibit No. 33, to the Expert Report of Professor Nick Oliver, Sep. 20, 2022: Rilstone, et al., The impact of CGM with a predictive hypoglycaemia alert function on hypoglycaemia in physical activity for people with type 1 diabetes: PACE study (2022).
Exhibit No. 34, to the Expert Report of Professor Nick Oliver, Sep. 20, 2022: FreeStyle Libre 2, Flash Glucose Monitoring System, User's Manual, Abbott (2019-2021).
Exhibit No. 35, to the Expert Report of Professor Nick Oliver, Sep. 20, 2022: FreeStyle Libre 3, Continuous Glucose Monitoring System, User's Manual, Abbott (2022).
Exhibit No. 30, to the Expert Report of Professor Nick Oliver, Sep. 20, 2022: Revised Specification for US 2007/208244A1.
Exhibit No. 22, to the Expert Report of Professor Nick Oliver, Sep. 20, 2022: Innovation Milestones, et al.
Exhibit No. 21, to the Expert Report of Professor Nick Oliver, Sep. 20, 2022: DeVries, Glucose Sensing Issues for the Artificial Pancreas, Journal of Diabetes Science and Technology, vol. 2, Issue 4, pp. 732-734 (2008).
Exhibit No. 37, to the Second Expert Report of Professor Nick Oliver, Oct. 21, 2022: Oliver, et al., Review Article, Glucose sensors, a review of current and emerging technology, Diabetic Medicine, vol. 26, pp. 197-210 (2009).
Approval letter from Department of Health and Human Services re. P050012/S001, STS-7 Continuous Glucose Monitoring System, dated May 31, 2007, 7 pages.
Declaration of Thomas Foster of Taylor Wessing LLP, Hill House, 1 Little New St. London EC4A3TR ("Taylor Wessing"), signed on Jan. 30, 2024 (160 pages).
PMA Final Decisions Rendered for May 2007, The Wayback Machine, U.S. Food and Drug Administration, 21 pages.
Premarket Approval (PMA) on Seven Plus Continuous Glucose Monitoring System, Notice date: Jun. 28, 2007, 3 pages.
STS-7 Continuous Glucose Monitoring System—P050012/S001, Approved May 31, 2007, The Wayback Machine, U.S. Food and Drug Administration, 1 page.
About Dexcom—Continuous Glucose Monitoring Company, 12 pages (2021).
Alva, S., et al., Accuracy of a 14-Day Factory-Calibrated Continuous Glucose Monitoring System With Advanced Algorithm in Pediatric and Adult Population With Diabetes, Journal of Diabetes Science and Technology, vol. 16(I), pp. 70-77 (2022).
Campbell, F. M., et al., Outcomes of using flash glucose monitoring technology by children and young people with type 1 diabetes in a single arm study, Pediatric Diabetes, pp. 1294-1301 (2018).
Deshmukh, H., et al., Effect of Flash Glucose Monitoring on Glycemic Control, Hypoglycemia, Diabetes-Related Distress, and Resource Utilization in the Association of British Clinical Diabetologists (ABCD) Nationwide Audit, Diabetes Care, 8 pages (2020).
General report of the German Diabetes Society on the state of diabetic patients and treatment methods for the year 2021, 15 pages (with English summary).
Haak, T., et al., Use of Flash Glucose-Sensing Technology for 12 months as a Replacement for Blood Glucose Monitoring in Insulin-treated Type 2 Diabetes, Diabetes Ther, 14 pages (2017).
Letter from Department of Health & Human Services, Food and Drug Administration, to Andy Balo, DexCom, Inc. re. P050012/S001, STS-7 Continuous Glucose Monitoring System dated May 31, 2007, 95 pages.
Roussel, R., et al., Important Drop in Rate of Acute Diabetes Complications in People With Type 1 or Type 2 Diabetes After Initiation of Flash Glucose Monitoring in France: The RELIEF Study, 5 pages, American Diabetes Association, Diabetes Care (2021).
STS®-Seven Continuous Glucose Monitoring System User's Guide, 74 pages (2007).
Summary of Safety and Effectiveness Data, STS®-7 Continuous Glucose Monitoring System, DexCom, Inc., Date of Approval: May 31, 2007, 14 pages.

* cited by examiner

METHOD AND SYSTEM FOR PROVIDING BASAL PROFILE MODIFICATION IN ANALYTE MONITORING AND MANAGEMENT SYSTEMS

RELATED APPLICATION

The present application is a continuation of U.S. patent application Ser. No. 16/177,811 filed Nov. 1, 2018, which is a continuation of U.S. patent application Ser. No. 15/880,692 filed Jan. 26, 2018, which is a continuation of U.S. patent application Ser. No. 15/613,713 filed Jun. 5, 2017, which is a continuation of U.S. patent application Ser. No. 15/071,610 filed Mar. 16, 2016, now U.S. Pat. No. 9,669,162, which is a continuation of U.S. patent application Ser. No. 14/081,737 filed Nov. 15, 2013, now U.S. Pat. No. 9,323,898, which is a continuation of U.S. patent application Ser. No. 12/833,975 filed Jul. 10, 2010, now U.S. Pat. No. 8,585,591, which is a continuation of U.S. patent application Ser. No. 11/267,724 filed Nov. 4, 2005, now U.S. Pat. No. 7,766,829, entitled "Method and System for Providing Basal Profile Modification in Analyte Monitoring and Management Systems", the disclosures of each of which are incorporated herein by reference for all purposes.

BACKGROUND

The present invention relates to analyte monitoring systems and health management systems. More specifically, the present invention relates to method and system for providing basal profile modification in analyte monitoring systems to improve insulin therapy in diabetic patients.

In data communication systems such as continuous, semi-continuous or discrete analyte monitoring systems for insulin therapy, analyte levels of a patient are monitored and/or measured, and the measured analyte levels are used for treatment. For example, real time values of measured analyte levels of a patient would allow for a more robust and accurate diabetes treatment. Moreover, a profile of a series of measured analyte levels of a diabetic patient can provide valuable information regarding the fluctuations and variations of the analyte levels in a diabetic patient. In turn, this type of information would be invaluable in establishing a suitable insulin therapy regimen.

Many diabetic patients that use an infusion device such as an infusion pump generally have preset or pre-established basal profiles which are programmed or stored into the infusion device by the patient's physician or the patient herself Indeed, based on several factors such as insulin sensitivity, the patient's physiology and other variable factors that affect the patient's analyte levels, the physician may tailor the basal profiles of the patient to be programmed into the infusion device such that the patient's analyte level is maintained within an acceptable range, and thus the patient is not going to experience hyperglycemia or hypoglycemia.

While physicians attempt to best determine the most suitable basal profiles for each diabetic patient using the infusion device, it is often difficult to attain the most suitable profiles to ensure the safe operating range of the infusion device while providing the patient with the most suitable level of insulin at all times when the patient is wearing and operating the infusion device.

Often, diabetics who use infusion pumps run basal profiles to maintain a steady level of insulin and also, supplement with additional boluses administered typically with the same infusion pumps. Various devices exist that enable the determination of the appropriate bolus to supplement the basal profiles. For example, prior to the ingestion of a large quantity of carbohydrates, the patient is able to calculate a carbohydrate bolus and administer the same with the infusion pump so that the intake of the carbohydrates does not adversely impact the patient's physiology. While bolus supplements are useful and critical to a well managed insulin therapy regimen, it does not address the underlying concern related to the basal profiles that the infusion devices are programmed to administer.

In view of the foregoing, it would be desirable to have a method and system for providing basal profile modification for diabetic patients so as to comprehend each patient's unique physiology as well as response to insulin intake. More specifically, it would be desirable to modify basal profiles such that as the use of the infusion device progresses, the patient's basal profiles may be tailored to be more suitable for that patient.

SUMMARY OF THE INVENTION

In accordance with the various embodiments of the present invention, there is provided a method and system for analyte monitoring and management configured to monitor the levels of a patient's analyte over a predetermined period of time, and based on the monitored analyte levels, determine one or more patterns in the analyte levels for the given period of time, and to provide a recommendation for modification to the basal profiles under which a medication delivery system such as an infusion pump is operating.

For example, in one embodiment, the analyte monitoring and management system of the present invention will be configured to monitor the analyte levels of a patient over a predetermined time period (for example, 1 day, 3 days, or 7 days), and during which, the patient is using an infusion device such as an insulin pump administering insulin based on a predetermined one or more basal profiles. Upon conclusion of the analyte level monitoring during the predetermined time period, the collected data are analyzed and, considered in conjunction with the underlying basal profiles under which the patient was infusing insulin during that same predetermined time period, used to determine a suitable modification to the basal profiles, if any, to improve the insulin therapy of the patient.

In this manner, a robust health management system may be provided which may be configured in one embodiment to monitor the analyte levels of a patient over a period of time and to recommend or suggest a modification to the existing or current basal profiles based on the collected and analyzed analyte levels taken in conjunction with the underlying basal profiles under which the infusion device was running during the time period of analyte level monitoring. Within the scope of the present invention, the monitored time period may vary depending upon the patient's need, the underlying basal profiles, the condition of the patient and the like, such that the patient may alter or modify the running basal profiles prior to its completion based on the monitored and analyzed analyte levels so as to provide a more effective insulin therapy.

DETAILED DESCRIPTION

Figure 1:
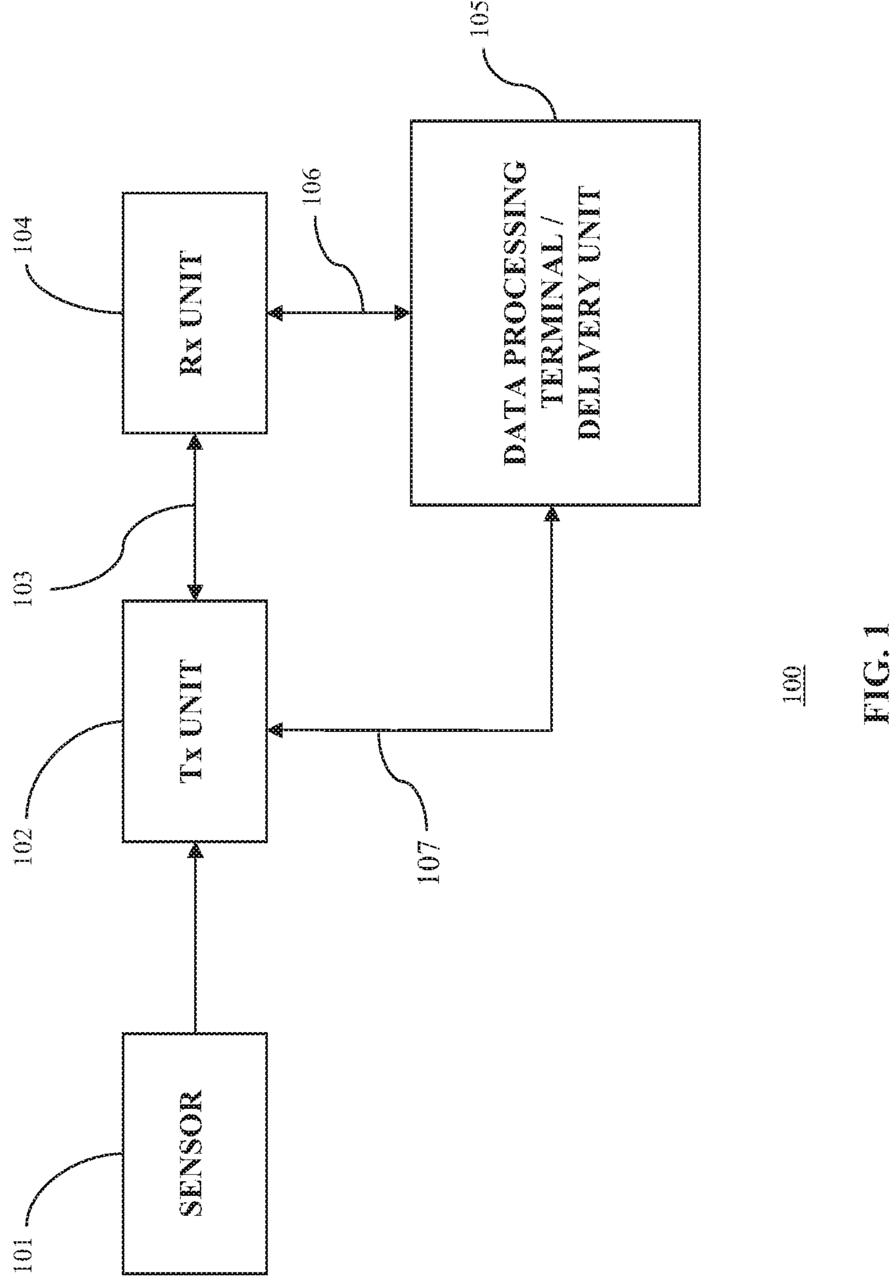
FIG. 1 illustrates a block diagram of a data monitoring and management system for practicing one embodiment of the present invention.

FIG. 1 illustrates a data monitoring and management system such as, for example, an analyte (e.g., glucose) monitoring and management system 100 in accordance with one embodiment of the present invention. The subject invention is further described primarily with respect to an analyte monitoring and management system for convenience and such description is in no way intended to limit the scope of the invention. It is to be understood that the analyte monitoring system may be configured to monitor a variety of analytes, e.g., lactate, and the like.

Indeed, analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The analyte monitoring and management system 100 includes a sensor 101, a transmitter unit 102 coupled to the sensor 101, and a receiver unit 104 which is configured to communicate with the transmitter unit 102 via a communication link 103. The receiver unit 104 may be further configured to transmit data to a data processing terminal 105 for evaluating the data received by the receiver unit 104 via communication link 106 which may optionally be configured for bi-directional communication. Moreover, the data processing terminal in one embodiment may be configured to receive data directly from the transmitter unit 102 via a communication link 107 which may optionally be configured for bi-directional communication.

Only one sensor 101, transmitter unit 102, receiver unit 104, and data processing terminal 105 are shown in the embodiment of the analyte monitoring and management system 100 illustrated in FIG. 1. However, it will be appreciated by one of ordinary skill in the art that the analyte monitoring and management system 100 may include one or more sensor 101, transmitter unit 102, receiver unit 104, and data processing terminal 105, where each receiver unit 104 is uniquely synchronized with a respective transmitter unit 102. Moreover, within the scope of the present invention, the sensor 101 may include a subcutaneous analyte sensor, a transcutaneous analyte sensor, an implantable analyte sensor, or a noninvasive analyte sensor such as a transdermal patch or an optical sensor (for example, infrared sensor).

Moreover, within the scope of the present invention, the analyte monitoring system 100 may be a continuous monitoring system, or semi-continuous, or a discrete monitoring system. Additionally, within the scope of the present invention, the sensor 101 may include a subcutaneous analyte sensor or an implantable analyte sensor which is configured to be substantially wholly implanted in a patient.

In one embodiment of the present invention, the sensor 101 is physically positioned in or on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is mounted on the sensor 101 so that both devices are positioned on the user's body. The transmitter unit 102 performs data processing such as filtering and encoding on data signals, each of which corresponds to a monitored analyte level of the user, for transmission to the receiver unit 104 via the communication link 103.

In one embodiment, the analyte monitoring system 100 is configured as a one-way RF communication path from the transmitter unit 102 to the receiver unit 104. In such embodiment, the transmitter unit 102 transmits the sampled data signals received from the sensor 101 without acknowledgement from the receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the receiver unit 104.

Additionally, in one aspect, the receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the receiver unit 104 is a data processing section which is configured to process the data signals received from the transmitter unit 102 such as by performing data decoding, error detection and correction, data clock generation, and data bit recovery.

In operation, upon completing the power-on procedure, the receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the receiver unit 104 is configured to begin receiving from the transmitter unit 102 data signals corresponding to the user's detected analyte level. More specifically, the receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 in one embodiment may be configured to include a medication delivery unit such as an infusion device including, for example, an insulin pump, and which may be operatively coupled to the receiver unit 104. In such an embodiment, the medication delivery unit 105 may be configured to administer a predetermined or calculated insulin dosage based on the information received from the receiver unit 104. For example, as discussed in further detail below, the medication delivery unit 105 in one embodiment may be configured to deliver insulin based on pre-programmed basal profiles to diabetic patients, as well as to determine and/or administer one or more suitable bolus levels (e.g., carbohydrate bolus, and correction bolus).

Referring again to FIG. 1, the receiver unit 104 may include a personal computer, a portable computer such as a laptop or a handheld device (e.g., personal digital assistants (PDAs)), and the like, each of which may be configured for data communication with the receiver via a wired or a wireless connection. Additionally, the receiver unit 104 may further be connected to a data network (not shown) for storing, retrieving and updating data corresponding to the monitored analyte levels of the patient.

Furthermore, in one embodiment of the present invention, the receiver unit 104 or the data processing terminal 105, or both the receiver unit 104 and the data processing terminal 105 may be configured to incorporate a glucose strip meter so as to be configured to include, for example, a test strip port for receiving a glucose test strip. In this embodiment of the present invention, the receiver unit 104 and the data processing terminal 105 may be configured to perform analysis upon the sample from the glucose test strip so as to determine the glucose level from the test strip. One example of such strip meter is Freestyle® glucose meters commercially available from the assignee of the present invention, Abbott Diabetes Care Inc. of Alameda Calif.

Furthermore, within the scope of the present invention, the data processing terminal 105 may include an infusion device such as an insulin infusion pump or the like, which may be configured to administer insulin to patients, and which may be configured to communicate with the receiver unit 104 for receiving, among others, the measured glucose level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the receiver unit 104 and the data processing terminal 105 may each be configured for bi-directional wireless communication such that each of the transmitter unit 102, the receiver unit 104 and the data processing terminal 105 may be configured to communicate (that is, transmit data to and receive data from) with each other via the wireless communication link 103. More specifically, the data processing terminal 105 may in one embodiment be configured to receive data directly from the transmitter unit 102 via the communication link 106, where the communication link 106, as described above, may be configured for bi-directional communication. In this embodiment, the data processing terminal 105 which may include an insulin pump, may be configured to receive the analyte signals from the transmitter unit 102, and thus, incorporate the functions of the receiver unit 104 including data processing for managing the patient's insulin therapy and analyte monitoring.

In one embodiment, the communication link 103 may include one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

Figure 2:
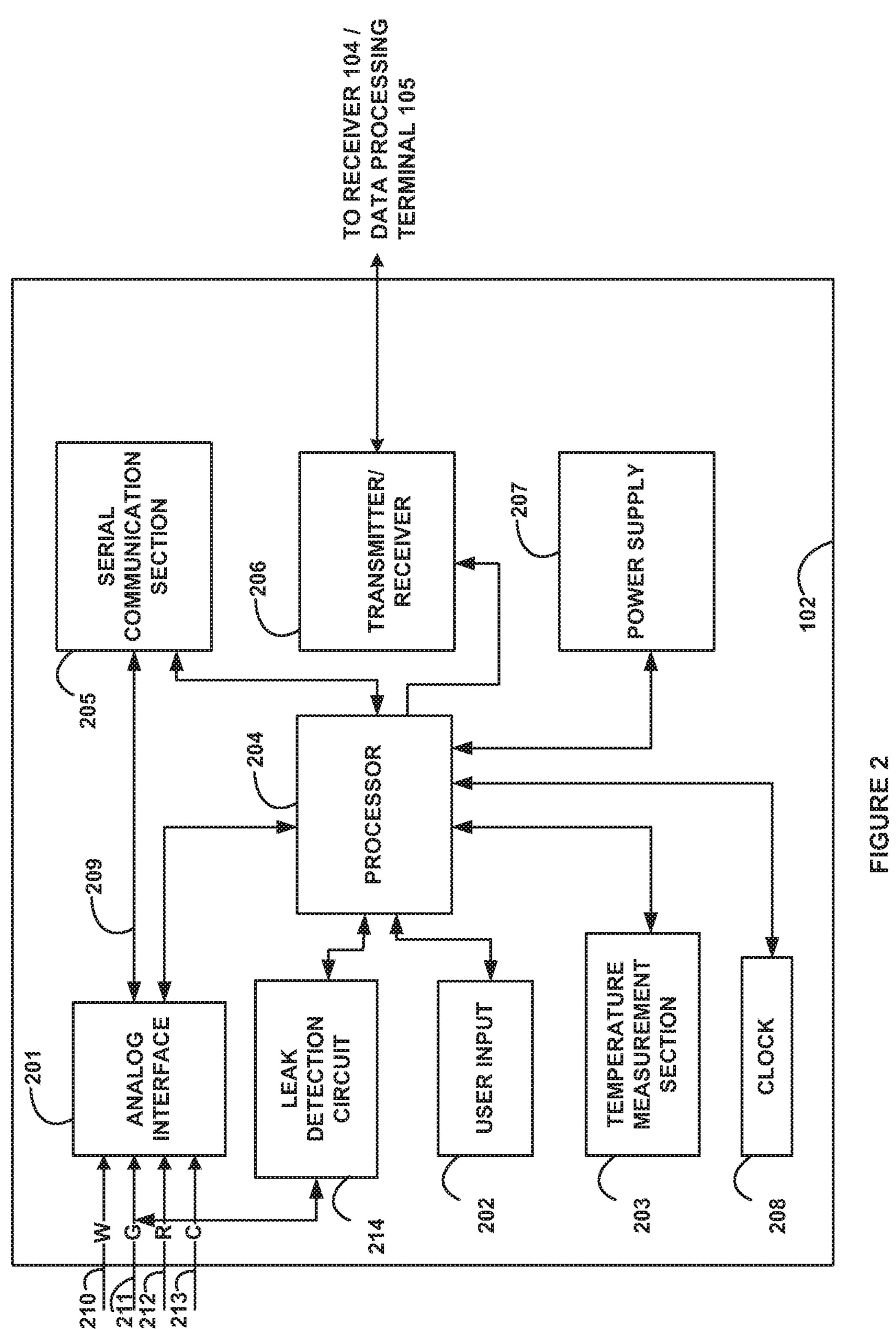
FIG. 2 is a block diagram of the transmitter unit of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter unit 102 in one embodiment includes an analog interface 201 configured to communicate with the sensor 101 (FIG. 1), a user input 202, and a temperature measurement section 203, each of which is operatively coupled to a transmitter processor 204 such as a central processing unit (CPU). As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the transmitter unit 102 for connection to the sensor 101 (FIG. 1). In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched.

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

In one embodiment, a unidirectional input path is established from the sensor 101 (FIG. 1) and/or manufacturing and testing equipment to the analog interface 201 of the transmitter unit 102, while a unidirectional output is established from the output of the RF transmitter 206 of the transmitter unit 102 for transmission to the receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor 101. The stored information may be retrieved and processed for transmission to the receiver unit 104 under the control of the transmitter processor 204. Furthermore, the power supply 207 may include a commercially available battery.

The transmitter unit 102 is also configured such that the power supply section 207 is capable of providing power to the transmitter for a minimum of about three months of continuous operation after having been stored for about eighteen months in a low-power (non-operating) mode. In one embodiment, this may be achieved by the transmitter processor 204 operating in low power modes in the non-operating state, for example, drawing no more than approximately 1 μA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present invention, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the temperature measurement section 203 of the transmitter unit 102 is configured to monitor the temperature of the skin near the sensor insertion site. The temperature reading is used to adjust the analyte readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the receiver unit 104.

Referring yet again to FIG. 2, also shown is a leak detection circuit 214 coupled to the guard contact (G) 211 and the processor 204 in the transmitter unit 102 of the data monitoring and management system 100. The leak detection circuit 214 in accordance with one embodiment of the present invention may be configured to detect leakage current in the sensor 101 to determine whether the measured sensor data is corrupt or whether the measured data from the sensor 101 is accurate.

Additional detailed description of the continuous analyte monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application, and the disclosures of each of which are incorporated herein by reference for all purposes.

Figure 3:
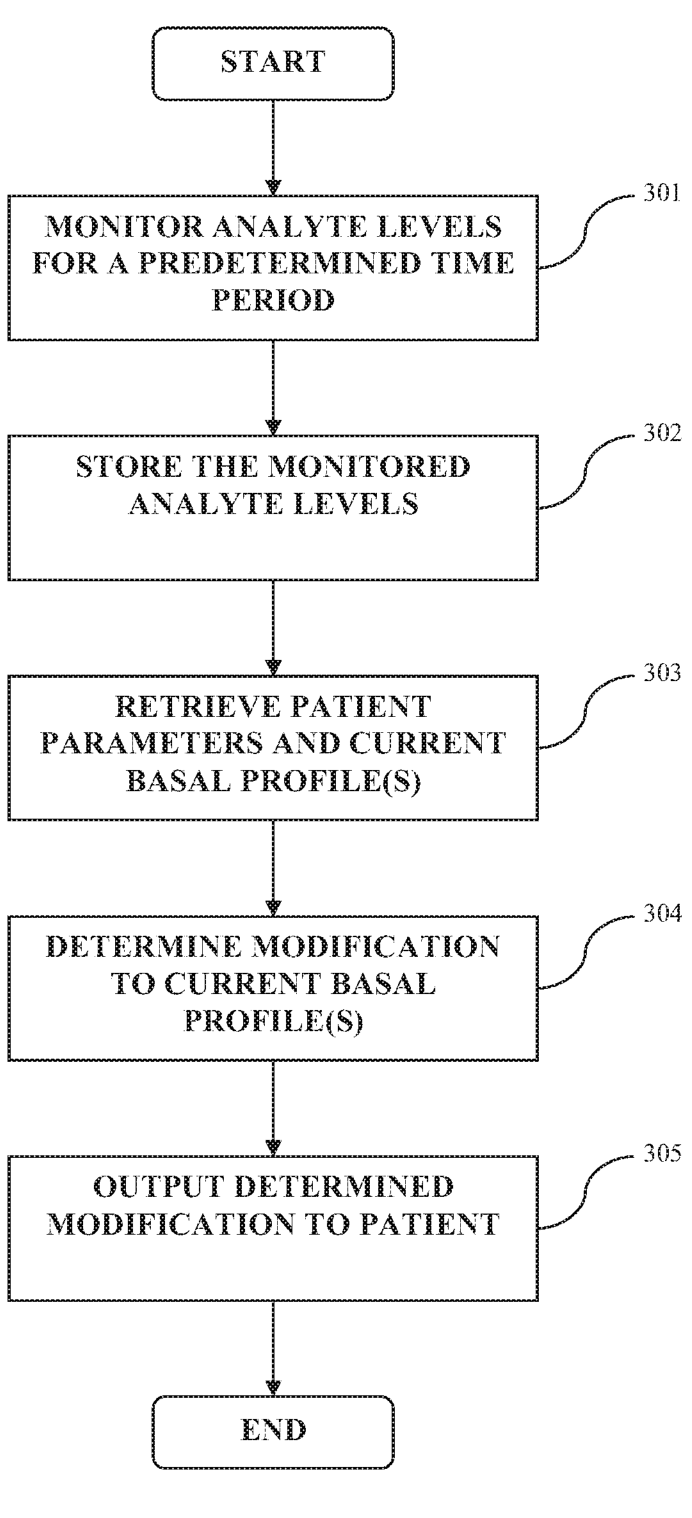
FIG. 3 is a flowchart illustrating the process for monitoring analyte levels and determining modification to a current basal profile in accordance with one embodiment of the present invention.

FIG. 3 is a flowchart illustrating the process for monitoring analyte levels and determining modification to a current basal profile in accordance with one embodiment of the present invention. Referring to FIG. 3, at step 301, the analyte levels such as the patient's analyte level is monitored for a predetermined period of time, and at step 302, the monitored analyte levels are stored in a data storage unit (for example, in one or more memory devices of the receiver unit 104 and/or the data processing terminal 105 (FIG. 1)). Thereafter, at step 303, patient specific parameters are retrieved from the data processing terminal 105 and/or the receiver unit 104, as well as the current basal profile(s) which the patient is implementing to operate the infusion device for insulin delivery during the time period of the analyte monitoring discussed above.

In one embodiment, patient specific parameters may include the type of insulin currently being infused into the patient, the patient's insulin sensitivity, insulin resistance level, level of insulin on board, the specific time period of the analyte monitoring, including the activities performed by the patient during that time period, or any other factors and variables that may have an impact upon the effectiveness of insulin therapy for the patient.

Referring to FIG. 3, after retrieving the patient specific parameters and the current basal profile(s) that the patient is implementing in the infusion device at step 303, at step 304, the monitored analyte levels are retrieved and, based on one or more patterns from the analyte levels monitored and factoring in the current basal profile(s), a recommendation or modification to the current basal profile(s) is determined. Thereafter, at step 305 the recommendation or modification to the current basal profile(s) determined at step 304 is provided to the patient visually on a display or audibly, or a combination of visual and audio output, such that the patient may be able to decide whether the modification to the current basal profile(s) is appropriate or suitable to the patient.

While the modification to the basal profile(s) is discussed above as output to the patient, within the scope of the present invention, the basal profile modification determined in accordance with one embodiment of the present invention may be provided to a health care provider so as to determine suitability of the modification to the current basal profile in view of the monitored analyte levels. Furthermore, in an alternate embodiment, the determined modification to the current basal profile may be provided to both the patient and the healthcare provider so that the patient is able to make an informed decision as to whether the recommended modification to the current basal profile is suitable for the patient in improving insulin therapy to better manage diabetes.

Within the scope of the present invention, the modification to the current basal profile may include several factors that are considered including, for example, the current basal profile as a function of the time period during which insulin infusion takes place and analyte levels are monitored, the level of the analyte monitored as a function of time, patient specific parameters discussed above including, for example, patient's activities during the monitored time period, patient's diet, insulin sensitivity, level of insulin on board, and the insulin type, and the frequency of bolus dosing during the time period of the analyte level monitoring (for example, the number of correction bolus dosing, and/or carbohydrate dosing).

In this manner, in one embodiment of the present invention, the modification to the current basal profile(s) may be achieved for one or more specific goals for the patient's diabetes management, including for example, elimination of extreme glucose excursions, automating or semi-automating routine or regular bolus dosing, and adjustment to the mean glucose value.

For example, to effectively eliminate extreme glucose excursions, the modification to the current basal profiles may be configured to provide recommendation to modify to reduce extreme levels, so that unless the monitored glucose level exceeds a predetermined threshold level (e.g., 200 mg/dL), modification to the current basal profile is not recommended. In the case of automating regular bolus dosing, based on the monitored analyte levels, a regular correction bolus dosing during the current basal profile implementation may be converted into a modification to the current basal profile so that the patient may effectively be rid of the need to implement routine correction type bolus dosing. Additionally, with the collected data from the continuously monitored analyte levels, the current basal profile may be modified to adjust the mean target glucose value even in the case where extreme excursions of glucose levels do not occur.

Within the scope of the present invention, the current basal profile modification may be performed at different times during the time that the patient is using an infusion device. For example, the patient may perform the current basal profile modification procedure discussed above on a daily basis if, for example, glucose excursions are anticipated on a regular basis. Alternatively, the current basal profile modification procedure may be performed each time a bolus is administered.

Moreover, within the scope of the present invention, when a pattern of glucose excursions is detected over several days (for example, 48 or 72 hours), the analyte monitoring and management system 100 (FIG. 1) may be configured to continue analyte level monitoring to determine whether a pattern exists in the frequency and/or level of the glucose excursions. In such a case, it is possible to modify the current basal profile modification procedure to correct for such patterns in the monitored analyte levels such that the modification to the current basal profile may address such excursions.

In a further embodiment, the loop gain setting may be configured to determine the appropriate level of modification to the current basal profiles for a given glucose excursion pattern detected based on the monitored analyte levels. While several iterations may be necessary for low loop gain to reach the optimal modification level of the current basal profile, a conservative and less aggressive modification may be recommended in such cases. For medium loop gain, when critically controlled, the determined recommendation for modification to the current basal profile may be reached based on one iteration, but with the potential for an increased risk for overshoot and thereby resulting in over-compensation. Notwithstanding, the loop gain setting may be trained into the analyte monitoring and management system 100 so that by starting with a low loop gain and then learning the loop responses to reach the optimal loop gain, the desired modification to the current basal profile may be determined and provided to the patient.

Figure 4A:
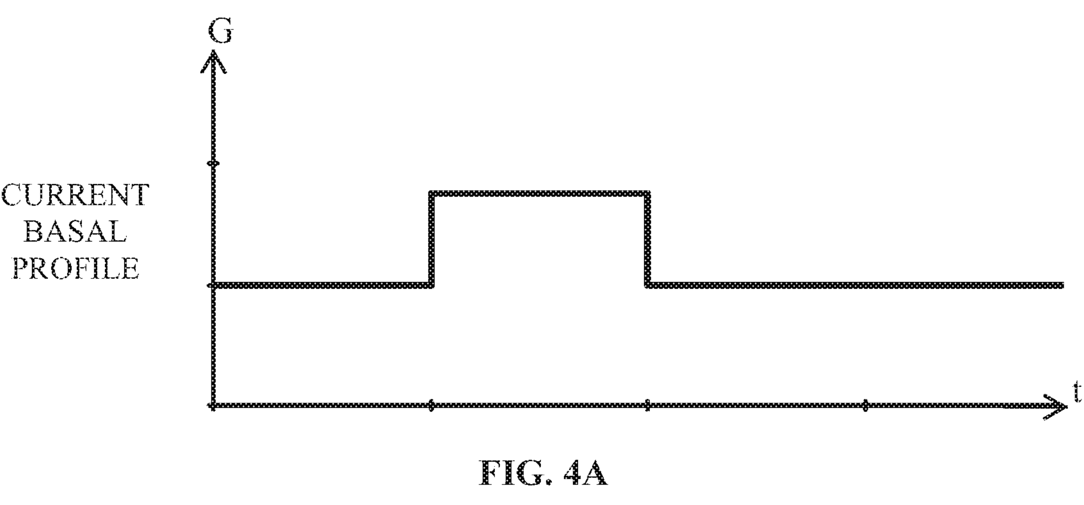
FIGS. 4A-4C illustrate a current basal profile, a monitored analyte level profile, and a modified basal profile recommendation respectively, in accordance with one embodiment of the present invention.
Figure 4B:
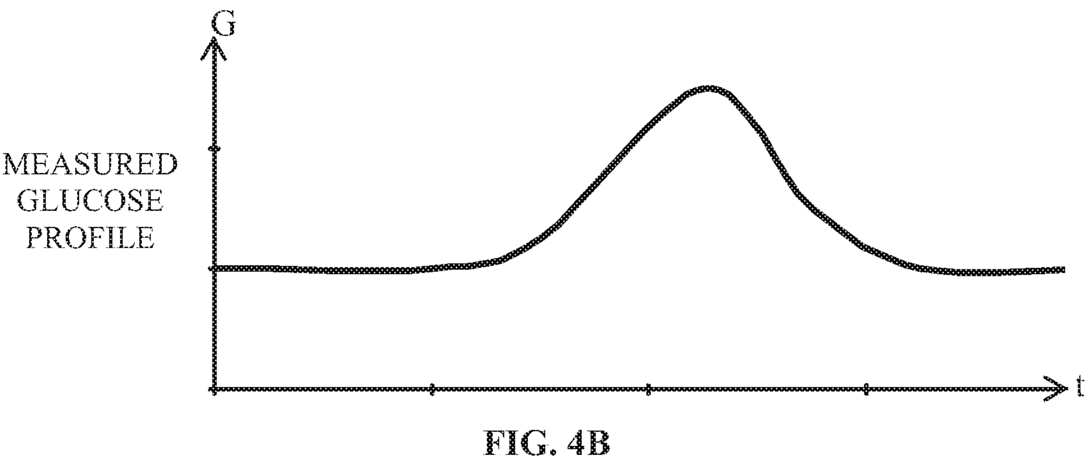
Figure 4C:
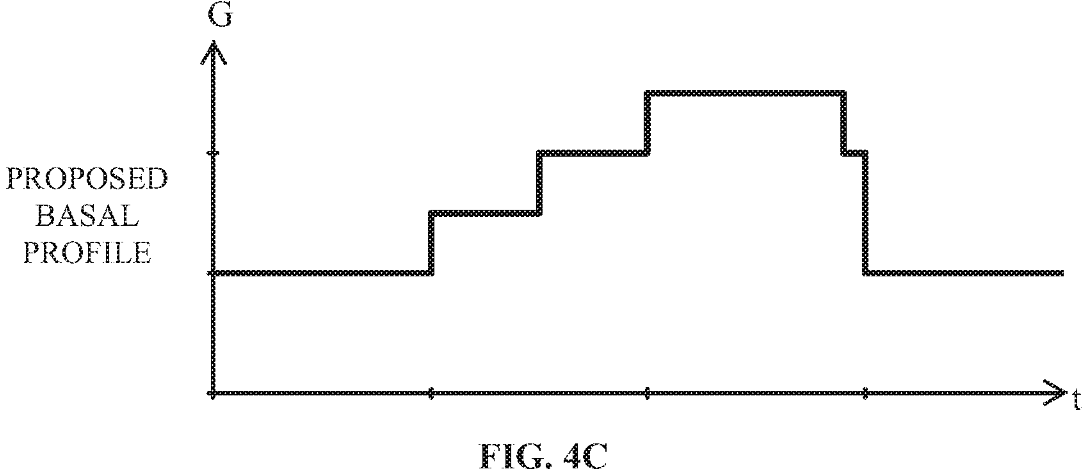

FIGS. 4A-4C illustrate a current basal profile, a monitored analyte level profile, and a modified basal profile recommendation respectively, in accordance with one embodiment of the present invention. Referring to FIG. 4A, a profile of the glucose level as a function of time is shown for a current basal profile programmed into the infusion device of the patient. FIG. 4B illustrates a profile of the glucose levels as a function of time for the same time period during which the basal profile shown in FIG. 4A is administered to the patient. Finally, FIG. 4C illustrates a profile of glucose level as a function of time which factors in the patient parameters including the monitored glucose levels of the patient, to provide a modification to the current basal profile so as to improve the patient's insulin therapy.

Indeed, in one embodiment of the present invention, it can be seen that the analyte level monitoring and detecting patterns in the monitored analyte levels during the time period that the patient is using an infusion device such as an insulin pump running a pre-programmed basal profile, provides contemporaneous patient response of the infused insulin based on the current basal profile, and thus, it is possible to improve the insulin therapy.

By way of an example, in the case that the patient desired to eliminate or substantially reduce the occurrences of high glucose extremes or excursions, it is determined whether there is a consistent pattern of high glucose levels versus time of day of such occurrence based on the monitored glucose levels. An example of such monitored levels is shown in the Table 1 below:

TABLE 1

| High Glucose Excursions | | | | | |
|---|---|---|---|---|---|
| | 00:00 | 00:30 | 01:00 | 01:30 | 23:30 |
| Day 1 (0-24 hr) | | | 1 | 1 | |
| Day 2 (24-48 hr) | 1 | | 1 | 1 | |
| Day 3 (48-72 hr) | 1 | 1 | 1 | | |
| Sum | 2 | 1 | 3 | 2 | 0 |

where over a 72 hour period post calibration of the sensor 101 (FIG. 1), the monitored data is reviewed to determine if the monitored glucose level exceeds a predetermined threshold level. Each occurrence of when the glucose level exceeds a predetermined threshold level is shown with a "1" in Table 1 above.

For each column shown in Table 1 where the sum of the data entry equals "3", and the sum of the adjacent columns is equal to or greater than "1", the analyte monitoring and management system 100 in one embodiment may be configured to recommend an increase to the current basal profile for that time slot or period during the 72 hour period.

More specifically, using a conventional bolus calculation mechanism, a correction bolus may be determined based on the detection of the high glucose level. Thereafter, rather than implementing the calculated correction bolus, the modification to the current basal profile may be determined based on the following relationship:

$$\text{Modification}=K^{*}\text{Calculated Correction Bolus/30 minutes} \quad (1)$$

where K is a loop gain value determined by the patient's health care provider, and is typically less than 1 for over dampened control, and further, where the 30 minutes is a scaling factor for the Modification determination.

After the calculation, the determined Modification from the equation (1) above is provided to the patient to either accept and implement, storage for further analysis or modification, or reject.

In one embodiment, the Modification determination based on relationship described in the equation (1) above may include glucose rate or higher derivative information, or alternatively, may also include an integral factor. In a further embodiment, the determination may also factor in the glucose profile variation. Other potentially relevant factors also include the physiological dynamics and/or sensor/monitor dynamics, as well as the patient's insulin infusions, caloric intake, exercise, etc.

As another example, in the case where correction bolus dosing may be replaced with modification to the current basal profiles based on the monitored analyte levels, a consistent pattern in the monitored analyte levels of bolus delivery versus time of day is determined. Table 2 below shows one example of such pattern:

TABLE 2

| Bolus Replacement | | | | | |
|---|---|---|---|---|---|
| | 00:00 | 00:30 | 01:00 | 01:30 | 23:30 |
| Day 1 (0-24 hr) | | | 1 | 1 | |
| Day 2 (24-48 hr) | 1 | | 1 | 1 | |
| Day 3 (48-72 hr) | 1 | 1 | 1 | | |
| Sum | 2 | 1 | 3 | 2 | 0 |

Referring to Table 2 and in conjunction with equation (1) discussed above, the administration of bolus doses is reviewed and if, for example, there were three bolus deliveries (each shown in Table 2 with a "1" entry) within 30 minutes of the same time of day period, then an increase in the insulin level for same time period may be proposed to the current basal profile using equation (1) to determine the level of modification to the current basal profile.

In the case of addressing the occurrence of low extremes of glucose levels, similar determinations as above may be performed given the monitored analyte levels for the desired time period and data reviewed for detection of patterns in the monitored analyte levels associated with the occurrences of low extremes. For example, Table 3 below provides data for a three day period illustrating patterns associated with the occurrences of low extremes.

TABLE 3

| Low Extremes Pattern | | | | | |
|---|---|---|---|---|---|
| | 00:00 | 00:30 | 01:00 | 01:30 | 23:30 |
| Day 1 (0-24 hr) | | | 1 | 1 | |
| Day 2 (24-48 hr) | 1 | | 1 | 1 | |
| Day 3 (48-72 hr) | 1 | 1 | 1 | | |
| Sum | 2 | 1 | 3 | 2 | 0 |

where the "1" entry in a particular column illustrates the occurrence of the measured glucose level that is below a predetermined low threshold level.

Again, in conjunction with equation (1) above, a modification to the current basal profile may be determined and provided to the patient. More specifically, where over a 72 hour period post calibration of the sensor 101 (FIG. 1), the monitored data is reviewed to determine if the monitored glucose level falls below the predetermined low threshold level, each such is shown with a "1" in Table 3 above.

For each column shown in Table 3 where the sum of the data entry equals "3", and the sum of the adjacent columns is equal to or greater than "1", the analyte monitoring and management system 100 in one embodiment may be configured to recommend a modification to the current basal profile for that time slot or period during the 72 hour period based on the relationship set forth in equation (1). The user or patient may then be provided with the modification to the current basal profile which may be accepted for implementation, stored for further analysis or modification, or rejected by the patient.

In the case of reducing the mean glucose level using the analyte monitoring and management system 100 in one embodiment of the present invention, again, consistent patterns in the monitored analyte levels over a predetermined time period is analyzed and detected as a function of time of day of the analyte level monitoring. Table 4 below shows an example of such pattern:

TABLE 4

| Mean Glucose Level | | | | | |
|---|---|---|---|---|---|
| | 00:00 | 00:30 | 01:00 | 01:30 | 23:30 |
| Day 1 (0-24 hr) | | | 1 | 1 | |
| Day 2 (24-48 hr) | 1 | | 1 | 1 | |
| Day 3 (48-72 hr) | 1 | 1 | 1 | | |
| Sum | 2 | 1 | 3 | 2 | 0 |

where, an entry of a "1" in Table 4 above illustrates a detected glucose level of greater than a predetermined level (e.g., 120) during the three day period based on the data from the sensor 101 (FIG. 1).

Again, similar to the determinations above, if the sum of any column in Table 4 is equal to three, and the sum of the adjacent columns is greater than or equal to one, then a decrease in the current basal profile for that particular time slot is recommended based on the relationship set forth above in equation (1).

In a further embodiment, a 24 hour profile may be determined based on time-of-day averages over a predetermined number of days. The correction factor may then be based on maintaining the time-of-day averages within a predetermined target range value. Within the scope of the present invention, the various approaches and implementations for correction calculation and/or basal profile modification recommendation may be combined or implemented individually, depending upon the patient's physiology and the criteria for drug therapy such as insulin therapy.

In accordance with the various embodiments of the present invention, additional or alternative approaches to the determination of the modification to the basal profile may include, for example, (1) modifying the basal rate by a constant value, (2) changing the basal rate by a constant percentage of the current basal profile rate, (3) changing the basal rate in proportion to the magnitude of the error, or (4) changing the basal rate in proportion to the magnitude of the error, compensating for the loop gain factor based on the affects of the previous basal rate modifications/adjustments. Each of these approaches within the scope of the present invention is described in further detail below.

In the first embodiment described above, the basal rate is configured for modification by a constant amount. For example, the modification is described by the following equation (2):

$$\text{Modification}=\text{sign}(\text{measured}-\text{target})*U \quad (2)$$

where U is a constant value in insulin units, and is applied to the difference between the target glucose and measured glucose levels.

Moreover, the "sign(measured−target)" relationship holds the following:

if(measured−target)=0, then 0
  else if (measured−target)>0, then +1
  else if (measured−target)<0, then −1

For example, in the equation (2) above, the constant value U may be 0.1 units of insulin/hour. This may be a configurable value. Indeed, for the case where U is 0.1 units, if the measured glucose level is 140, while the target glucose level is 100, then the Modification to the basal rate would result in +1*0.1 equaling 0.1 units/hour.

In this manner, in one embodiment, a simple and effective basal rate modification approach is provided and which does not require knowledge of the patient's physiology, is simple to implement, and does not provide resolution issues. On the other hand, for safe values of the constant factor U, several iterations or corrections may be needed to reach the desired results.

In another embodiment, the basal rate may be modified by a constant percentage of the current rate. In this case, the following equation (3) holds:

$$\text{Modification}=\text{sign}(\text{measured}-\text{target})*K*U \quad (3)$$

where K=constant percentage, 0<=K<=1, and U=current basal rate(in units of insulin).

For example, where the constant percentage K is 0.1 and with the current basal rate U of 2.0 units/hour, and for example, the measured and target glucose levels at 140 and 100, respectively, the basal rate Modification in accordance with the equation (3) equals +1*0.1*2.0=0.2 units/hour. In this manner, in one embodiment, a simple and effective way to implement basal rate modification is provided, and which does not require the knowledge of the user's physiology. For safe values of the constant percentage K, several iterations may be needed to reach the desired level of basal rate modification, and resolution issues may potentially arise.

In a further embodiment of the present invention, the modification to the basal rate may be determined by changing the basal rate proportionally to the magnitude of the error. In this case, the following equation (4) holds:

$$\text{Modification}=(\text{measured}-\text{target})*K*P \quad (4)$$

where K is the loop gain factor, and for example, K<1 for dampened control, K=1 for critical control, K>1 for over control, and further, where P is the patient's physiological response to insulin (insulin sensitivity).

For example, in the case where the loop gain factor K is 0.75, the patient's insulin sensitivity P is 0.02 units/mg/dL, and where the measured and target glucose levels are 140 and 100, respectively, the Modification to the basal rate in accordance to equation (4) is determined to be (140−100)*0.75*0.02=0.6 units/hour. This approach requires prior determination of the patient's insulin sensitivity, and may likely require less iterations or corrective routines to reach the desired level of basal rate modification for effective treatment.

In still a further embodiment, the modification to the basal rate may be determined by changing the basal rate proportionally to the magnitude of error, and further making adjustment to the loop gain factor based on the results of the prior basal rate adjustments. For example, the following equation (5) holds:

$$\text{with } K=f(\text{affect of last adjustment})$$

$$\text{Modification}=(\text{measured}-\text{target})*K*P \quad (5)$$

where K is loop gain factor, and P is the patient's physiology response to insulin (insulin sensitivity).

For example, if the loop gain factor is initially 0.75, then the determined basal rate modification is the same as in the embodiment described above in conjunction with equation (4). In the next iteration, with the measured glucose level still higher than the target level, the loop gain factor is increased. In this case, for example, with measured glucose level of 110 where the target level is 100, the new loop gain factor K is determined to be ((first delta)/(first change))*old K=(40/30)*0.75=1.00.

Having determined the new loop gain factor K, the basal rate modification is determined by equation (5) as (110−100)*1.00*0.02=0.2 units/hour. It is to be noted that if the loop gain factor K did not change between the two iterations described above, then the basal rate modification in the second iteration may be relatively smaller, and it can be seen that the adjustment to the loop gain factor allows faster settling to the final value. For example, using equation (5) above, the basal rate modification is determined as:

$$\text{Modification}=(110-100)*0.75*0.02=0.15 \text{ units/hour}$$

In this manner, in one embodiment of the present invention, the basal rate modification may be configured to self adjust to the patient's physiology such that it may be more tolerant of inaccurate input values.

In this manner, the various embodiments of the present invention provides a mechanism for diabetic patients to compare the actual glucose levels during a predetermined time period and to use that information in addition to the actual basal profile to recommend a new or modified basal profile to the patient. The patient will have the option to accept the recommendation, to accept the recommendation with the modification, or alternatively to decline the proposed modified basal profile so as to select the most appropriate basal profile for the patient.

Moreover, contrasting with real time closed loop insulin therapy where the insulin infusion is modified at a rate (i.e., minutes) much faster than the physiological response times, one embodiment of the present invention is characterized by a) corrections to basal profiles that are made over periods (i.e., days) which are much longer than physiological response times, and b) corrections based on repeating diurnal glucose patterns. In this manner, in one embodiment, the present invention is configured to identify the patient's glucose levels retrospectively over a predetermined period of time (for example, over a 24 hour period) to determine any recommended modification to the existing basal profiles. In this manner, the recommended modification to the basal profiles will be a function of the actual measured glucose values of the patient under the existing basal profiles.

In the manner described above, in accordance with the various embodiments of the present invention, the patient and the doctor or educator may work together to adjust the insulin profile to the patient's activities. This will require experience and some trial and error as well. An automated basal profile correction in accordance with the embodiments of the present invention may monitor and gather much more information and may incorporate the knowledge of the physician/educator within the modification algorithm. Indeed, different objectives can be identified and the modification algorithms developed to achieve the objectives.

Accordingly, a method in one embodiment includes monitoring an analyte level of a patient, retrieving a predetermined parameter, and determining a modification to a drug therapy profile based on the monitored analyte level and the predetermined parameter.

The analyte includes glucose, and the drug infusion rate may include a basal profile.

Further, the predetermined parameter may include one or more of an insulin sensitivity, a drug infusion rate, and a drug infusion time period, a time period corresponding to the monitored analyte level, a time of day associated with the monitored analyte level, or a loop gain factor.

Moreover, the monitoring step may include determining the analyte level of the patient at a predetermined time interval including one of 5 minutes, 30 minutes, 1 hour, or 2 hours.

The method in one embodiment may further include the step of outputting the modification to the drug therapy profile to the patient.

Also, the method may additionally include the step of implementing the modification to the drug therapy profile.

In a further aspect, the drug therapy profile may include an insulin infusion profile.

A system in yet another embodiment of the present invention includes an analyte monitoring unit, and a processing unit operatively coupled to the analyte monitoring unit, the processing unit configured to receive a plurality of monitored analyte levels of a patient, and to determine a modification to a drug therapy profile based on the received plurality of monitored analyte levels.

The analyte monitoring unit in one embodiment may include a sensor provided in fluid contact with an analyte of a patient.

Further, the sensor may include a subcutaneous analyte sensor, a transcutaneous analyte sensor, and a transdermal patch sensor.

Moreover, the processing unit may be operatively coupled to an infusion device.

In a further aspect, the processing unit may include an insulin pump.

Moreover, in still another aspect, the processing unit may be configured to determine the modification based on a pattern in the monitored analyte level, where the pattern may be determined based on the plurality of monitored analyte levels for a predetermined time period, and further, where the predetermined time period may include one of a 12 hour period, or 24 hour period.

The system in yet another embodiment may include a display unit operatively coupled to the processing unit for displaying the determined modification.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method for diabetes management, the method comprising:

receiving glucose data corresponding to a glucose level of a user from a glucose monitor comprising a transcutaneous glucose sensor;

retrieving, by one or more processors in communication with the glucose monitor, patient specific parameters comprising one or more of exercise, caloric intake or insulin sensitivity;

detecting, by the one or more processors, a pattern of glucose excursions in which the received glucose levels exceed a predetermined glucose level threshold;

determining, by the one or more processors, a glucose metric based on the received glucose levels;

determining, by the one or more processors, a modification to an insulin therapy profile when the pattern of glucose excursions is detected, wherein the modification is determined based on a gain factor and a difference between the glucose metric and a target glucose metric;

outputting, by the one or more processors, the modification to the insulin therapy profile to a medication delivery unit; and implementing the modification via the medication delivery unit.

2. The method of claim 1, wherein the insulin therapy profile is an insulin infusion profile.

3. The method of claim 1, wherein the insulin therapy profile is a basal delivery profile.

4. The method of claim 1, wherein the modification is outputted to at least one of a device of a patient or a device of a healthcare provider.

5. The method of claim 4, wherein the modification is outputted at least one of visually or audibly.

6. The method of claim 1, wherein the received glucose levels exceed the predetermined glucose level threshold when the received glucose levels rise above a high glucose level threshold.

7. The method of claim 1, wherein the received glucose levels exceed the predetermined glucose level threshold when the received glucose levels fall below a low glucose level threshold.

8. The method of claim 1, wherein the received glucose levels exceed the predetermined glucose level threshold when a mean glucose level is greater than a predetermined level.

9. The method of claim 1, further comprising determining the pattern of glucose excursions when the glucose excursion occurs at a same time of day over a plurality of days.

10. The method of claim 1, wherein detecting the pattern of glucose excursions comprises determining that a number of glucose excursions in a time of day period meets or exceeds a minimum number of glucose excursions over a predetermined number of days.

11. The method of claim 1, wherein the modification is further determined based on the patient specific parameter, wherein the patient specific parameter is an insulin sensitivity.

12. A system for diabetes management comprising:

a glucose monitoring unit comprising a transcutaneous glucose sensor; and one or more processors operatively coupled to the glucose monitoring unit and configured to:

receive glucose data corresponding to a glucose level of a user from the glucose monitoring unit;

retrieve patient specific parameters comprising one or more of exercise, caloric intake or insulin sensitivity;

detect a pattern of glucose excursions in which the received glucose levels exceed a predetermined glucose level threshold;

determine a glucose metric based on the received glucose levels;

determine a modification to an insulin therapy profile when the pattern of glucose excursions is detected, wherein the modification is determined based on a gain factor and a difference between the glucose metric and a target glucose metric;

provide the modification to the insulin therapy profile to a medication delivery unit; and implement the modification via the medication delivery unit.

13. The system of claim 12, wherein the insulin therapy profile is an insulin infusion profile.

14. The system of claim 12, wherein the insulin therapy profile is a basal delivery profile.

15. The system of claim 12, wherein the modification is outputted to at least one of a device of a patient or a device of a healthcare provider.

16. The system of claim 15, wherein the modification is outputted at least one of visually or audibly.

17. The system of claim 12, wherein the received glucose levels exceed the predetermined glucose level threshold when the received glucose levels rise above a high glucose level threshold.

18. The system of claim 12, wherein the received glucose levels exceed the predetermined glucose level threshold when the received glucose levels fall below a low glucose level threshold.

19. The system of claim 12, wherein the pattern of glucose excursions comprises a number of glucose excursions in a time of day period meeting or exceeding a minimum number of glucose excursions over a predetermined number of days.

20. The system of claim 12, wherein the modification is further determined based on the patient specific parameter, wherein the patient specific parameter is an insulin sensitivity.

* * * * *